US006359124B1

(12) United States Patent
Ecker et al.

(10) Patent No.: US 6,359,124 B1
(45) Date of Patent: *Mar. 19, 2002

(54) ANTISENSE INHIBITION OF RAS GENE WITH CHIMERIC AND ALTERNATING OLIGONUCLEOTIDES

(75) Inventors: David J. Ecker, Leucadia; Phillip Dan Cook, Escondido; Brett P. Monia, La Costa; Susan M. Freier, San Diego; Yogesh S. Sanghvi, Encinitas, all of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/248,386

(22) Filed: Feb. 12, 1999

Related U.S. Application Data

(60) Division of application No. 08/848,840, filed on Apr. 30, 1997, now Pat. No. 5,965,722, which is a continuation-in-part of application No. 07/411,734, filed on Sep. 25, 1989, now Pat. No. 4,945,741.

(51) Int. Cl.[7] .................. C07H 21/02; C07H 21/04; C07H 19/16; C12Q 1/68; A01N 43/04
(52) U.S. Cl. .................. 536/23.1; 435/6; 536/24.5; 536/27.21; 536/28.4; 536/28.5; 514/44
(58) Field of Search ............... 536/23.1, 24.5, 536/27.21, 28.4, 28.5; 435/6; 514/44

(56) References Cited

U.S. PATENT DOCUMENTS

| 3,687,808 A | 8/1972 | Merigan et al. ............ 295/28 |
| 4,511,713 A | 4/1985 | Miller et al. |
| 4,689,320 A | 8/1987 | Kaji ........................ 514/44 |

(List continued on next page.)

FOREIGN PATENT DOCUMENTS

| CA | 2017369 | 11/1990 |
| DE | 3915462 A1 | 6/1990 |
| DE | 41 10 085 | 10/1992 |
| DE | 41 10085 A1 | 10/1992 |
| EP | 87307595 | 8/1987 |
| EP | 0 260 032 A2 | 3/1988 |
| EP | 0 269 574 A2 | 6/1988 |
| EP | 0287313 | 10/1988 |
| EP | 365 627 B1 | 3/1989 |
| EP | 89303700 | 4/1989 |
| EP | 0 339 330 | 11/1989 |
| EP | 0 339 842 A2 | 11/1989 |

(List continued on next page.)

OTHER PUBLICATIONS

Sanghvi, Y. S. et al., "Concept, Discovery and Development of MMI Linkage: Story of a Novel Linkage for Antisense Constructs," *Nucleosides & Nucleotides*, 1997, 16(7–9), 907–916.

(List continued on next page.)

*Primary Examiner*—Jeffrey Fredman
*Assistant Examiner*—Arun Chakrabarti
(74) *Attorney, Agent, or Firm*—Woodcock Washburn LLP

(57) ABSTRACT

Compositions and methods are provided for the modulation of expression of the human ras gene in both the normal and activated forms. Oligonucleotides are provided that have methylene(methylimino) linkages alternating with phosphorothioate or phosphodiester linkages. Further oligonucleotides are provide that have a first region having a methylene (methylimino) linkage alternating with a phosphorothioate or phosphodiester linkage and a second region having phosphorothioate linkages. Such oligonucleotides can be used for diagnostics as well as for research purposes including methods for diagnosis, detection and treatment of conditions arising from the activation of the H-ras gene.

8 Claims, 30 Drawing Sheets

U.S. PATENT DOCUMENTS

| | | | |
|---|---|---|---|
| 4,707,440 A | 11/1987 | Stavrianopoulos | 536/25.3 |
| 4,867,187 A | 9/1989 | Duck | 435/6 |
| 4,871,838 A | 10/1989 | Bos et al. | 536/27 |
| 4,876,335 A | 10/1989 | Yamane et al. | 536/27 |
| 4,908,307 A | 3/1990 | Rodland et al. | 435/6 |
| 4,965,350 A | 10/1990 | Inoue et al. | 536/28 |
| 5,013,830 A | 5/1991 | Ohtsuka et al. | 536/27 |
| 5,034,506 A | 7/1991 | Summerton et al. | 528/391 |
| 5,085,983 A | 2/1992 | Scanlon | 435/6 |
| 5,087,617 A | 2/1992 | Smith | 514/44 |
| 5,134,066 A | 7/1992 | Rogers et al. | 435/6 |
| 5,138,045 A | 8/1992 | Cook et al. | 536/27 |
| 5,149,797 A | 9/1992 | Pederson et al. | 536/27 |
| 5,212,295 A | 5/1993 | Cook | 536/26.7 |
| 5,214,134 A | 5/1993 | Weis et al. | 536/25.3 |
| 5,220,007 A | 6/1993 | Pederson et al. | 536/23.1 |
| 5,223,618 A | 6/1993 | Cook et al. | 544/276 |
| 5,256,775 A | 10/1993 | Froehler | 536/25.6 |
| 5,359,044 A | 10/1994 | Cook et al. | 536/23.1 |
| 5,366,878 A | 11/1994 | Pederson et al. | 435/91.3 |
| 5,378,825 A | 1/1995 | Cook et al. | 536/25.34 |
| 5,386,023 A | 1/1995 | Sanghvi et al. | 536/25.3 |
| 5,403,711 A | 4/1995 | Walder et al. | 435/6 |
| 5,466,786 A | 11/1995 | Buhr et al. | 536/26.26 |
| 5,541,307 A | 7/1996 | Cook et al. | 536/23.1 |
| 5,578,718 A | 11/1996 | Cook et al. | 536/27.21 |
| 5,582,986 A | 12/1996 | Monia et al. | 435/6 |
| 5,618,704 A | 4/1997 | Sanghvi et al. | 435/91.5 |
| 5,623,070 A | 4/1997 | Cook et al. | 536/27.6 |
| 5,658,731 A | 8/1997 | Sproat et al. | 435/6 |
| 5,965,722 A | * 10/1999 | Ecker et al. | 536/23.1 |

FOREIGN PATENT DOCUMENTS

| | | | |
|---|---|---|---|
| EP | 0378518 | 7/1990 | |
| EP | 0 381 335 | 8/1990 | |
| EP | 0417999 | 3/1991 | |
| EP | 260032 | 1/1994 | |
| JP | 3-240795 | 10/1991 | |
| WO | WO 88/07544 | 10/1988 | |
| WO | WO 89/05358 | 6/1989 | |
| WO | WO 89/11486 | 11/1989 | |
| WO | WO 89/12060 | 12/1989 | |
| WO | WO 90/08156 | 7/1990 | |
| WO | WO 90/15065 | 12/1990 | |
| WO | WO 90/15814 | 12/1990 | |
| WO | WO 91/06556 | 5/1991 | |
| WO | WO 91/10671 | 7/1991 | |
| WO | WO 91/12323 | 8/1991 | |
| WO | WO 91/15499 | 10/1991 | |
| WO | WO 92/02258 | 2/1992 | |
| WO | WO 92/02534 | 2/1992 | |
| WO | WO 92/03568 | 3/1992 | |
| WO | WO 92/05186 | 4/1992 | |
| WO | WO 92/07065 | 4/1992 | |
| WO | WO 92/15680 | 9/1992 | |
| WO | WO 92/20822 | 11/1992 | |
| WO | WO 92/22651 | 12/1992 | |
| WO | WO 93/08296 | * 4/1993 | 514/44 |
| WO | WO 93/18052 | 9/1993 | |
| WO | WO 94/02498 | 2/1994 | |

OTHER PUBLICATIONS

Inoue, H., et al., "Synthesis and hybridization studies on two complementary nona(2'–O–methyl)ribonucleotides, "*Nucl. Acids Res.*, 1987, 15, 6131–6148.

Barton, D. et al., "Steroselectivity in radical reactions of 2'–deoxynucleosides. A synthesis of an isostere of 3'–azido–3'–deoxythymidine–5'–monophosphate (AZT–5' monophosphate)", *Tetrahedron Letters*, 1989, 30(37), 4969–4972.

Cormier et al., "Synthesis of hexanucleotide analogues containing diisopropylsilyl internucleotide linkages", *Nucleic Acids Research*, 1988, 16, 4583–4594.

Curran, D. P., "Radical Addition Reactions", in "Comprehensive Organic Synthesis", Trost, B. M. and Fleming, I. (Eds.), vol. 4., p. 715–823 Pergamon Press, Oxford (1991).

Fikes, L. et al., "Presassociating α–Nucleophiles", *J. Am. Chem. Soc.,* 1992, 114, 1493–1495.

Goodchild, J. et al., "Conjugates of Oligonucleotides and Modified Oligonucleotides: A Review of Their Synthesis and Properties", *Bioconjugate Chemistry*, 1990, 1(3), 165–187.

Halford and Jones, "Synthetic Analogues of Polynucleotides", *Nature,* 1968, 217, 638–640.

Jenkins, S. R. and Walton, E., "[52] 9–(2–methyl–β–D–ribofuranosyl)adenine (2'–methyladenosine)" in *Synthetic Procedures in Nucleic Acid Chemistry,* Zorbach and Tipson (eds.), vol. 1, pp. 149–153, Wiley & Sons, Undated.

Kirshenbaum, M. R. et al., "Novel oligonucleotide analogues with a sulfur–based linkage", *The Fifth San Diego Conference on Nucleic Acids: New Frontiers, American Association for Clinical Chemistry,* Nov. 14–15, 1990, Poster 28.

Motawia, M. and Pederson, "A New Route to 2',3'–Dideoxycytidine", *Liebigs Ann. Chem.* 1990, 599–602.

Sproat, B. S. et al., "2'–O–Methyloligoribonucleotides: Synthesis and Applications", in *Oligonucleotides and Analogues—A Practical Approach,* Eckstein, F. (ed.), Oxford University Press, Oxford, 1991, pp. 49–86.

Zon and Stec, "Phosphorothioate Oligonucleotides", *Oligonucleotides and Analogs: A Practical Approach,* F. Eckstein (ed.), IRL Press, Chapter 4, 87–108 (1991).

Debart, F. et al., "Intermolecular Radical C–C Bond Formation: Synthesis of a Novel Dinculeoside Linker for Non–Anionic Antisense Oligonuclesides", *Tetra. Lett.,* 1992, 33(19), 2645–2648.

Etzold, G. et al., "The Extension of the Sugar Chain of Thymidine: A New Route to 5'–Deoxyhexose Nucleosides", *Chemical Communications* 1968, p. 422.

Goodchild, J., "Inhibition of Gene Expression by Oligonucleotides", in "Oligonucleotides", CRC Press, USA, 1989, pp. 53–78.

Heinemann, U. et al., "Effect of a Single 3'–methylene Phosphonate Linkage on the Conformation of an A–DNA Octamer Double Helix", *Nucleic Acids Res.,* 1991, 19(3), 427–433.

Kondo, K. et al., "Synthesis of 5'(e')–O–amino Nucleosides", *Nucleic Acids Research Symposium Series,* No. 16, 1985, 93–96.

Koole, L. et al., "Enhanced Stability of a Watson & Crick DNA Duplex Structure by Methylation of the Phosphate Groups in One Strand", *Proceedings of the Koninklijke Nederlandse Akademie van Wetenschappen,* 1987, 90(1), 41–46.

Montgomery, J. and Thomas, "Nucleosides Containing Chemically Reactive Groups. 2. Chloromethylketo Derivatives of Pyrimidine Nucleosides", *Nucleic Acids Research Symposium Series No. 9,* 1981, 95–97.

Montgomery, J. et al., "Potential Inhibitors of Nucleotide Biosynthesis. 2. Halomethyl Ketone Derivatives of Pyrimidine Nucleosides", *J. Med. Chem.*, 1984, 27, 680–684.

Morr, M. et al., "Building Blocks for the Chemical Synthesis of DNA Containing C(3')–CH$_2$–P Bonds", *Chemical Synthesis in Molecular Biology*, GBF (Gesellschaft fuer Biotechnologische Forschung Braunschweig–Stoeckheim), Bloecker et al. (eds.), 1987, vol. 8, pp. 107–113.

Rawson, T. et al., "The Synthesis of 5'–Homo–2'–Deoxycytidine", *Nucleosides & Nucleotides*, 1990, 9(1), 89–96.

Secrist III, J. et al., "5'–C'–Chain–Extended Adenosine Derivatives Related to Sinefungin. SYnthesis and Biological Activity", *Nucleosides & Nucleotides*, 1990, 9(4), 619–627.

Vasseur, J. et al., "Oligonucleosides: Synthesis of a Novel Methylhydroxylamine–Linked Nucleoside Dimer and Its Incorporation Into Antisense Sequences", *J. Am. Chem. Soc.*, 1992, 114, 4006–4007.

Gait, M. J., ed., "Oligonucleotide Synthesis", A Practical Approach (IRL Press, 1984).

Cohen, J. S., ed., Oligonucleotides: Antisense Inhibitors of Gene Expression, (CRC Press, Inc., Boca Raton, FL), 1989.

Cosstick, et al., "Synthesis and properties of Dithymidine Phosphate Analogues Containing 3'–Thiothymidine", *Nucleic Acids Res.*, 1990, 18, 829.

Fleet, et al., "Methyl 5–0–Tert –Butyldiphenylsilyl–2–Deoxy–αβ–D–Threo–Pentofuranoside as a Divergent Intermediate for the Synthesis of 3'–Substituted –2', 3'–Dideoxynucleosides: Synthesis of 3'–Azido–3'–Deoxythymidine, 3'–Deoxy–3'–Flurothymidine and 3'–Cyano–3'–Deoxythymidine", *Tetrahedron*, 1988, 44, 625–636.

Gura, "Antisense has Growing Pains", *Science*, 1995, 270, 575–577.

Barton, et al., A "One–Pot" Synthesis of Sulfenamides, *J. Org. Chem.*, 1991, 56:6702.

Horwitz, et al., "Nucleosides. V. The Monomesylates of 1–(2'–Deoxy–β–D–Lyxofuranosyl) Thymine", *J. Org. Chem.*, 1964, 29, 2076.

Jones, et al., "Synthesis of Carbocyclic Nucleosides: Preparation of (–)–5'–Homoaristeromycin and Analogues", J. Chem. Soc. Perkins Trans., 1988, 1:2927.

Bankston, et al., "A Short Synthesis of 5'–O–Trityl–Protected threo–and erythro–3'–Cyano–3'–deoxythymidine Epimers", *J. Het. Chem.*, 1992, 29, 1405–1407.

Beaucage, et al., "Advances in the Synthesis of Oligonucleotides by the Phosphoramidite Approach", *Tetrahedron*, 1992, 48, 2223–2311.

Fiandor, et al., "Synthesis of 3'–deoxy–3'–(2–propynyl) thymidine and 3'–cyanomethyl–3'–deoxythmidine, analogs of AZT", *Tetrahedron Letts.*, 1990, 33, 597–600.

Hata, et al., *J. Chem. Soc., Perkin I*, 1980, 306.

Hillgartner, et al., "Bis(trimethylzinn)benzpinakolat,seine reversible radialische Dissoziation und Reaktionen", *Liebigs Ann. Chem.*, 1975, 586–599.

Hronowski, et al., "Synthesis of New Carbocyclic Analogues of 3'–Azido–and 3'–Amino–2', 3'–dideoxynucleosides", *J. Chem. Soc., Chem. Commun.*, 1990, 1547–1548.

Koster, et al., "Dialkyl Aluminum Chloride", *Tetrahedron Letts.*, 1982, 23, 2641–2644.

Lim, et al., Book of Abstracts, 203 ACS National Meeting, San Francisco, CA, Apr. 5–10, 1992, of the procedure of Hill, et al., *J. Chem. Soc.*, 1964, 3709.

Moffatt, et al., "The Synthesis of 6'–Deoxyhomonuceoside–6'–phosphonic Acids", *J. Am. Chem. Soc.*, 1968, 90, 5337–5338.

Nicolaou, et al., "Carbocyclic Thromboxane A$_{2^1}$", *J. Am. Chem. Soc.*, 1980, 102, 1404–1409.

Shaw, et al., "Modified deoxyoligonucleotides stable to exonuclease degradation in serum", *Nucleic Acids Res.*, 1991, 19, 747–750.

Poopeiko, et al., "A Simple Method for Azido Group Reduction", *Syn. Lett.*, 1991, 342.

Secrist, et al., Abstract 21, Synthesis and Biological Activity of 4'–Thionucleosides, Program & Abstracts, Tenth International Roundtable, Nucleosides, Nucleotides and their Biological Applications, Park City, Utah, Sep. 16–20, 1992.

Wu, et al., New Synthesis of 2'–3'–Dideoxy–3'C–Cyano–2'–Substituted Thymidines by Michael Additional Reac–tions, *Tett. Letts.*, 1989, 45, 855–862.

Parkes, et al., "A Short Synthesis of 3'–Cyano–3'–Deoxythymidine", *Tetrahedron Letts.*, 1988, 29, 2995–2996.

Verheyden, et al., Halo Sugar Nucleosides. II., *J. Org. Chem.*, 1970, 35, 2868–2877.

Yang, et al., "Construction of Glycosidic N–O Linkages in Oligosaccharides", *J. Am. Chem. Soc.*, 1991, 113, 4715–4716.

Miller, et al., "Effects of a Trinucleotide Ethyl Phosphotriester G$^m$p(Et)G$^m$p(Et)U, on Mammalian Cells in Culture", *Biochemistry*, 1981, 20, 1874–1880.

Coull, et al., *Tetrahedron Letts.*, 1987, 28, 745–748.

van der Krol, A. R. et al., "Modulation of Eukaryotic Gene Expression by Complementary RNA or DNA Sequences", *Bio Techniques*, 1988, 6, 958–976.

Matteucci, "Deoxyoligonucleotide Analogs Based on Formacetal Linkages", *Tetrahedron Letts.*, 1991, 31, 2385–2388.

Quaedflieg, et al., *Recl. Rev. Chim. Pays–Bas*, 1991, 110, 435–436.

Miller, *Biotechnology*, 1991, 9, 358–362.

Nicolaou, et al., *J. Am. Chem. Soc.*, 1983, 105, 2430–2434.

Huang, et al., "Building Blocks for Oligonucleotide Analogues with Dimethylene Sulfide, Sulfoxide and Sulfone Groups Replacing Phosphodiester Linkages", *J. Org. Chem.*, 1991, 56, 3869–3882.

Stirchak, E. P. and Summerton, J. E., "Uncharged Stereoregular Nucleic Acid Analogues", *J. Org. Chem.*, 1987, 52, 4202–4206.

Mertes and Coats, "Synthesis of Carbonate Analogs of Dinucleosides. 3'–Thymidinyl 5'–Thymidinyl Carbonate, 3'–Thymidinyl 5'–(5–Fluoro–2'–deoxyuridinyl) Carbonate, and 3'–Thymidinyl 5'–(Fluoro–2'–deoxyuridinyl) 5'–thymidinyl Carbonate", *J. Med. Chem.*, 1969, 12, 154–157.

Matteucci, et al., "Deoxynucleosides Bearing Neutral Analogues of Phosphodiester Linkages Recognize Duplex DNA via Triple–Helix Formation", *J. Am. Chem. Soc.*, 1991, 113, 7767–7768.

Tittensor, J. R., *J. Chem. Soc.* (C), 1971, 2656–2662.

Veeneman, G. A., et al., *Tetrahedron*, 1991, 47, 1547–1562.

Schneider, K. C. and Benner, S. A., *Tetrahedron Letts.*, 1990, 31, 335–338.

Trainor, et al., "The Design and synthesis of Fluorescence–Tagged Dideoxynucleotides for Automated DNA Sequencing", *Third Chemical Congress of North America, Organic Chemistry,* 1988, Canada, Jun. 5–10, 1988, Abstract No. ORGN 317.

Gait, M.J., et al., *J. Am. Chem. Soc. Perkin I,* 1974, 1684.

Veeneman, G. A., et al., "Synthesis of Oligodeoxynucleotides Containing Thymidines Linked Via an Internucleosidic–(3'–5')–Methylene Bond" *Recueil des Trav. Chim.,* 1990, 109, 449–451.

Camarasa, et al., "Aldol Reaction of Nucleoside 5'–Carboxaldehydes with Acetone–Synthesis of 5'–C–Chain Extended Thymidine Derivatives" *Nucleosides and Nucleotides,* 1990, 9, 533.

Wilson, D. B., "Cellular Transport Mechanisms", *Ann. Re. Biochem.,* 1978, 47, 933–965.

Miller, P. S., et al., "Effects of a trinucleotide ethyl phosphotriester G^m p(Et)G^m p(Et)U, on mammalian cells in culture", *Biochemistry,* 1977, 16, 1988–1996.

Marcus–Sekura, C. H., et al., "Comparative Inhibition of chloramphenicol Acetyltransferase Gene Expression by Antisense Oigonucleotide Analogues having Alkyl Phosphotriester, Methylphosphonate and Phosphorothioate Linkages", *Nuc. Acids Res.,* 1987, 15, 5749–5763.

Loke, S. K., et al., "Delivery of c–myc Antisense Phosphorothioate Oligodeoxynucleotides to Hematopoietic Cells in Culture by Liposome Fusion: Specific Reduction in c–myc Protein Expression Correlates with Inhibition of Cell Growth and DNA Synthesis", *Top. Microbiol. Immunol.,* 1988, 141, 282–289.

Mazur, et al., "Isosteres of Natural Phosphates. 11. Synthesis of a Phosphonic Acid Analogue of an Oligonucleotide", *Tetrahedron,* 1984, 40, 3949–3956.

Neumeyer, J. L., et al., *J. Org. Chem.,* 1973, 38, 2291.

Matsuda, A., et al., "Synthesis and Biological Activities of 3'–Deoxy–3'–Isocyano,–Isothiocyano, and– Isoselenocyano–Thymidines", *Nucleosides & Nucleotides,* 1990, 9, 587.

Magid, et al., "Reductive Amination of Aldehydes and Ketones by Using Sodium Triacetoxyborohydride", *Tett. Letts.,* 1990, 31, 5595.

Kappler, et al., Nucleic Acid Chemistry, Part 4, L. B. Townsend and R. S. Tipton, Eds., Wiley–Interscience Publications, 1991, 240.

Bodenteich, M., et al., "Synthesis if Enantiomerically Pure Carbocyclic 3'–Azido–2',3'–Dideoxythymidine, A Potential Anti–Aids Drug", *Tetrahedron Letts.,* 1987, 28, 5311.

Nair, V. & Buenger, G. S., "Regiospecific 5'–Silylation of Nucleosides", *Org. Pre. Procedures Int.,* 1990, 22, 57–61.

Motawai, M. S., et al., "A New Route to 2',3'–Dideoxycytidine", *Liebigs Ann. Chem.,* 1990, 599–602.

Baud, et al., "Improved Procedure for the Regiospecific Synthesis of 2'–Deoxyribonucleosides", *Tetrahedron Letts.,* 1990, 31, 4437–4440.

Verheyden, J.P.H. and Moffatt, J. G., "Halo Sugar Nucleosides. I. Iodination of the Primary Hydroxyl Groups of Nucleosides with Methyltriphenoxyphosphonium Iodide", *J. Org. Chem.,* 1970, 35, 2119.

Hanamoto, et al., "$SmI_2$–Promoted Ketyl Addition to O–Benzyl Formaldoxime. A New Aminomethylation", *Tett. Letts.,* 1991, 32, 3555.

Tseng and Brown, Eds., *Gene Therapy,* vol. 1, 1994, pp. 65–71.

Mirabelli, Ed., *Anti–Cancer Drug Design,* 1991, 6, 647–661.

Uhlmann, et al., *Chem. Revs.,* 1990, 90, 544–584.

Miller, et al., "Oligonucleotide Inhibitors of Gene Expression in Living Cells: New Opportunities in Drug Design", *Annual Reports in Med. Chem.,* 1988, 23, 295–304.

Agrawal, et al., "Oligodeoxynucleoside Phosphoramidates and Phosphorothioates as Inhibitors of Human Immunodeficiency Virus", *Proc. Natl. Acad. Sci. USA,* 1988, 85, 7079–7083.

Petersen, et al., "Chemical Synthesis of Dimer Ribonucleotides Containing Internucleotidic Phosphoradithioate Linkages", 1990, 31, 911–914.

Miller, et al., "A new approach to chemotherapy based on molecular biology and nucleic acid chemistry: Matagen (masking tape for gene expression)", *Anti–Cancer Drug Design,* 1987, 117–128.

Cohen, "Oligodeoxynucleotides", published 1989 by CRC Press, Inc., Boca Raton, FL, pp. 1–255.

Brill, et al., "Synthesis of Deoxydinucleotide Phosphorodithioates", *J. Am. Chem. Soc.,* 1991, 113, 3972–3980.

Kawasaki, et al., "Synthesis and Biophysical Studies of 2'–dR1B0–2'–F Modified Oligonucleotides", Jan. 13, 1991, *Conference on Nucleic Acid Therapeutics,* Clearwater, FL, pp. 1–9.

Bertelsen, et al., *Bio Technol.,* 1995, 13, 127–131.

Grimm, et al., *FASEB J,* 1992, 6(5), A1644, abstract 4098.

Khurshid, et al., *FEBS Letters,* 1972, 28, 1–25.

Kielanowska, et al., *Nucleic Acids Res.,* 1976, 3(3), 817.

Kusmierek, et al., *ACTA, Biiochimica Polonica,* 1973, 20(4), 365.

Pike, et al., *J. Org. Chem.,* 1974, 39(25), 3674.

Ransford, et al., J. Carbohydrates—Nucleosides—Nucleotides, 1974, 1(3), 275.

Rottman, et al., *Biochemistry,* 1974, 13, 2762.

Tazawa, et al., *Biochemistry,* 1972, 11, 4931.

Chavis, et al., "Synthesis of 2',3'–Differentiated Ribonucleosides via Glycosylation Reactions with 2'–O–Me or 2'–O–TBDMS Ribofuranose Derivatives, I. Pyrimidine Series", J. Org. Chem., 1982, 47, 202–206.

Divakar, et al., "Reaction Between 2,2'–Anhydro–1–β–D–arabinofuranosyluracil and Thiolate Ions", *J. Chem. Soc., Perkin Trans. I,* 1982, 1625–1628.

Singer and Kusnierek, "Alkylation of Ribose in RNA Reacted with Ethylnitrosourea at Neutrality", *Biochemistry,* 15, 1976, 5053–5057.

Wagner, et al., "Preparation and Synthetic Utility of Some Organotin Derivatives of Nucleosides", *J. Org. Chem.,* 39, 1974, 24–30.

Egholm, et al., "Peptide Nucleic Acids (PNA). Oligonucleotide Analogues with an Achiral Peptide Backbone", *J. Am. Chem. Soc.,* 1992, 114, 1895–1897.

Giannis, et al., "Fragmentation and Wittig Olefination of Glucosamine Derivatives–A Simple Route to Open Chain Amino Sugars and Chiral Glyerols", *Tetrahedron,* 44, 1988, 7177–7180.

Greene, et al., *Protective Groups in Organic Synthesis,* John Wiley & Sons, Inc., 1991, pp. 175–223.

Hart, et al, "Bis(trimethylstannyl)benzopinocolate–Mediated Intermolecular Free–Radical Carbon–Carbon Bond Forming Reactions: A New One–Carbon Homologation", J. Am. Chem. Soc., 1988, 110, 1631–1633.

Hyrup, et al., "Modification of the Binding Affinity of Peptide Nucleic Acids (PNA). PNA with Extended Backbones consisting of 2–Aminoethyl–β–alanine or 3–Aminopropylglycine Units", *J. Chem. Soc. Chem. Comm.*, 1993, 518–519.

Inouye, et al., "Selective Coloration of Spiro Pyridopyrans for Guanosine Derivatives", J. Am. Chem. Soc., 1992, 114, 778–780.

Lin, et al., "Synthesis and Biological Activity of Several Amino Analogues of Thymidine", *J. Med. Chem.*, 1978, 109–112.

Ma, et al., "Design and synthesis of RNA miniduplexes via a synthetic linker approach. 2. Generation of covalently closed, double–standed cyclic HIV-1 TAR TNA analogs with high Tat–binding affinity", *Nucleic Acids Res.*, 1993, 21, 2585–2589.

Pauling, "Molecular Architecture and Biological Reactions", *Chem. Eng. News*, 1946, 24, 1375–1377.

Perkins, et al., "Accelerated Displacement of Duplex DNA Strands by a Synthetic Circular Oligodeoxynucleotide", *J. Chem. Soc. Chem. Comm.*, 1993, 215–216.

Prakash, et al., "Molecular Recognition by Circular Oligonucleotides. Strong Binding of Single–stranded DNA and RNA", *J. Chem. Soc. Chem. Commun.*, 1161–1163 1991.

Rebek, Jr., "Molecular Recognition and Biophysical Organic Chemistry", *Ace. Chem. Res.*, 1990, 23, 399–404.

Rentzeperis, et al., "Contribution of Loops and Nicks to the Formation of DNA Dumbbells: Melting Behavior and Ligand Binding", *Biochemistry*, 1993, 32, 2564–2572.

Sanghvi, et al., "Synthesis and Structure of Methylene (dimethylhydrazo) Linked Thymidine Dimer and Their Utility as Antisense Oligonucleotides", *Collect Czech. Chem. Commun.*, 1993, 58, 158–162.

Trapani, et al., "N–1–Alkenyl-N, S–Diacylk–2–Aminobenzenethiols (Enamides) by Ring–Opening of 2,3–Dihydro–1,3–benzothiazoles with Aliphatic Carboxylic Anhydrides", *Synthesis*, 84, 1988.

Trost, et al., ed., Comprehensive Organic Synthesis, vol. 4, pp. 758–776, 1991.

Tuladhar, et al., "A Synthetic Route to Poly–N,N'–Dimethylethylenediamines", *Tet. Letts.*, 1992, 33, 2203–2206.

Yamamoto, et al., "One–Step Synthesis of 5'–Azido–nucleosides", 1980, *J. Chem. Soc. Perkin I*, 306–310.

Zuckermann, et al., "Efficient Method for the Preparation of Peptoids [Oligo(N–substituted glycines)] by submonomer Solid–phase Synthesis", *J. Am. Chem. Soc.*, 1992, 114, 10646–10647.

Greenberg, M. E., *Current Protocols in Molecular Biology*, F. M. Ausubel, et al., eds., 1993, John Wiley & Sons, NY.

Jones, R. A., "Preparation of Protected Deoxyribonucleotides", *Oligonucleotide Synthesis—A Practical Approach*, 1991, IRL Press, Washington, D.C.

Dagle, et al., "Physical properties of oligonucleotides containing phosphoramidate–modified internucleoside linkages", *Nuc. Acids. Res.*, 1991, 19, 1805–1810.

Dagle, et al., "Targeted degradation of mRNA in Xenopus oocytes and embryos directed by modified oligonucleotides: studies of An2 and cyclin in embyrogenesis", *Nuc. Acids. Res.*, 1990, 18, 4751–4757.

Dagle, et al., "Pathways of Degradation and Mechanism of Action of Antisense Oligonucleotides in *Xenopus laevis* Embyros", *Antisense Res. Dev.*, 1991, 1, 11–20.

Saison–Behmoraras, et al., "Short modified antisense oligonucleotides directed against Ha–ras point mutation induce selective cleavage of the mRNA and inhibit T24 cells proliferation", *EMBO J.*, 1991, 10, 1111–1118.

Inoue, et al., "Synthesis and hybridization studies on two complementary nona (2'–O–methyl)ribonucleotides", *Nucleic Acids Res.*, 1987, 15, 6131–6148.

Inoue, et al., "Synthesis and properties of novel nucleic acid probes", Nucleic Acids Res., Symposium Series, 1985, 16, 165–168.

Monia, et al., "Evaluation of 2'–Modified Oligonucleotides Containing 2'–Deoxy Gaps as Antisense Inhibitors of Gene Expression", *J. Bio. Chem.*, 1993, 208(19), 14514–14522.

Kawasaki, et al., Uniformly Modified 2'–Deoxy–2'–fluoro Phosphorothioate Oligonucleotides as Nuclease–Resistant Antisense Compounds with High Affinity and Specificity for RNA Targets, *J. Med. Chem.*, 1993, 36, 831–ISIS–841.

Block, et al., *Gene*, 1988, 72, 349–360.

Ikehara, et al., *Nucl. Acids Res.*, 1977, 4(12), 4249–4260.

Berkowitz, et al., *J. Med. Chem.*, 1973, 16(2), 813–814.

Augustyns, et al., "Influence of the Incorporation of (S)–9–(3,4–dihydroxy–butyl)Adenine on the Enzymatic Stability and Base–Pairing Properties of Oligodeoxynucleotides", *Nucl. Acids Research*, 1991, 19, 2587–2593.

Borthwick, et al., Synthesis of Chiral Carbocylic Nucleosides, *Tetrahedron*, 1992, 48, 571–623.

Eder, P. S. and Walder, J. A., "Ribonuclease H from K562 Human Erythroleukemia Cells", *J. Biol. Chem.*, 1991, 266(10), 6472–6479.

Gagnor, et al., "α–DNA VI: Comparative Study of α–and mRNA and in Cell Free Translation Inhibition", *Nucleic Acids Research*, 1987, 15, 10419–10436.

Kierzek, et al., "Association of 2'–5' Oligoribonucleotides", *Nucleic Acids Res.*, 1992, 20, 1685–1690.

Matteucci, M., "Hybridization Properties of a Deoxyoligonucleotide Containing Four Formacetal Linkages", *Nucleosides & Nucleotides*, 1991, 10, 231–234.

Miller, et al., "Synthesis of oligo–2'–deoxyribonucleoside methylphosphonates", Chapter 6, p. 137, *Oligonucleotides and Analogs*, A Practical Approach, , Eckstein, F., Ed., The Practical Approach Series, IRL Press, New York, 1991.

Perbost, et al., "Sugar Modified Oligonucleotides 1. Carbo–Oligodeoxynucleotides as Potential Antisense Agents", *Biochem. and Biophys. Res. Comm.*, 1989, 165, 742–747.

Sagi, et al., "Biochemical Properties of Oligo(+)–Carbocyclic–Thymidylates] and Their Complexes", *Nucleic Acids Res.*, 1990, 18, 2133–2140.

Schneider, et al., "Oligonucleotides Containing Flexible Nucleiside Analogues", *J. Am. Chem. Soc.*, 1990, 112, 453–455.

Stawinski, J., et al., Tenth International Roundtable : Nucleosides, Nucleoties and Their Biological Evaluation, Sep., 1992, Abstracts of Papers, Abstract 80.

Szemzo, et al., "First Synthesis of Carbocyclic Oligothymidylates", Tetrahedron Letters, 1990, 31, 1463–1466.

Agris, et al., "Inhibition of Vesicular Stomatitis Virus protein Synthesis and Infection by Sequence–Specific Oligodeoxyribonucleoside Methylphosphonates", *Biochemistry*, 1986, 25(20), 6268–6275.

Atkinson and Smith, "Solid–Phase Synthesis of Oligodeoxyribonucleotides by the Phosphite–triester Method", Oligonucleotide Synthesis, a Practical Approach, Chapter 3, pp. 35–81.

Biggadike, et al., "Short Convergent Route to Homochiral Carbocyclic 2'-Deoxynucleosides and Carbocyclic Ribonucleosides", *J. Chem. Soc., Chem. Commun.*, 1987, 1083–1084.

Brill, et al., "Synthesis of Oligodeoxynucleoside Phosphorodithioates via Thioamidites", *J. Am. Chem. Soc.*, 1989, 111, 2321–2322.

Castle and Seese, "Imidaza[4,5–d]pyridazines I. Synthesis of 4,7–Disubstituted Derivatives", *J. Org. Chem.*, 1958, 23, 1534–1538.

Cazenave, et al., "Enzymatic Amplification of Translation Inhibition of Rabbit β–globin mRNA Mediated by Anti–Messenger Oligodeoxynucleotides Covalently Linked to Intercalating Agents", *Nucl. Acids Res.*, 1987, 15(12), 4717–4736.

Constant, et al., "Heterodimeric Molecules Including Nucleic Acid Bases and 9–Aminoacridine. Spectroscopic Studies, Conformations and Interactions with DNA", *Biochemistry*, 1988, 27, 3997–4003.

Dreyer and Dervan, "Sequence–Specific Cleavage of Single–Stranded DNA: Oligodeoxynucleotide—EDTA–Fe(II)", Proc. Natl. Acad. Sci. USA, 1985, 82, 968–972.

Freskos, J. N., "Synthesis of 2'–Deoxypyrimidine Nucleosides Via Copper (I) Iodide Catalysis", Nucleosides & Nucleotides, 1989, 8(5&6), 1075–1076.

Jarvi, et al., "Synthesis and Biological Evaluation of Dideoxunucleosides Containing a Difluoromethylene Unit", Nucleosides & Nucleotides, 1989, 8(5&6), 1111–1114.

Jayaraman, et al., "Selective Inhibition of *Escherichia Coli* Protein Synthesis and Growth By nonionic Oligonucleotides Complementary to the 3' End of 16S rRNA ", *Proc. Natl. Acad. Sci.*, 1981, 78(3), 1537–1541.

Beaton, et al., "Synthesis of oligonucleotide phosphorodithioates", *Oligonucleotides and Analogs, A Practical Approach*, 1991, Chapter 5, IRL Press, New York, Eckstein, F., Ed., 109–135.

Jones, et al., "4–Substituted Nucleosides. 5. Hydroxymethylation of Nucleoside 5'-Aldehydes", *J. Org. Chem.*, 1979, 44(8), 1309–1317.

Kazimeirczuk et al., "Synthesis of 2'–Deoxytubercidin, 2'–Deoxyadenosine, and Related 2'–Deoxynucleosides via a Novel Direct Stereospecific Sodium Salt Glycosylation Procedure", *J. Am. Chem. Soc.*, 1984, 106, 6379–6382.

Le Doan et al., "Sequence–Targeted Chemical Modifications of Nucleic Acids by Complimentary Oligonucleotides Covalently Linked to Porphyrins", *Nucl. Acids Res.*, 1987, 15(21), 8643–8659.

Letsinger et al., "Effects of Pendant Groups at Phosphorus on Binding Properties of d–ApA Analogs", *Nucl. Acids Res.*, 1986, 14(8), 3487–3499.

Matsukura et al., "Phosphorothioate Analogs of Oligodeoxynucleotides: Inhibitors of Replication and Cytopathic Effects of Human Immunodeficiency Virus", *Proc. Natl. Acad. Sci.*, 1987, 84, 7706–7710.

Meyer et al., "Efficienct, Specific Cross–Linking and Cleavage of DNA by Stable, Synthetic Complementary Oligodeoxynucleotides", *J. Am. Chem.Soc.*, 1989, 111, 8517–8519.

Miller et al., "Biochemical and Biological of Nonionic Nucleic Acid Methylphosphonates", *Biochemistry*, 1981, 20, 1874–1880.

Miller et al., "Nonionic Nucleic Acid Analogs. Synthesis and Characterization of Dideoxyribonucleoside Methylphosponates", *Biochemistry*, 1979, 18, 5134–5142.

Miller et al., "Synthesis and Properties of Adenine and Thymine Nucleoside Alkyl Phosphortriesters, the Neurtral Analogs of Dinucleoside Monophosphates", *J. Am. Chem. Soc.*, 1971, 93, 6657–6664.

Outten, R. A., "Synthetic 1–Methoxybenxo[d]naphtho[1, 2–b]pyran–6–one C–Glycosides", *J. Org. Chem.*, 1987, 52, 5064–5066.

Revankar et al., "Synthesis and antiviral/Antitumor Activities of Certain 3–Deazaguanine Nucleosides and Nucleotides", *J. Med. Chem.*, 1984, 27, 1389–1396.

Robins, M. J. et al., "Nucleic Acid Related Compounds. 42. A General Procedure for the Efficient Deoxygenation of Secondary Alcohols. Regiospecific and Stereoselective Conversion of Ribonucleosides to 2'–Deoxynucleosides", *J. Am. Chem. Soc.*, 1983, 105, 4059–4065.

Roelen et al., "Synthesis of Nucleic Acid Methylphosphonthioates", *Nucl. Acids. Res.*, 1988, 16, 7633–7645.

Ruby, S. W. et al., "An Early Hierarchic Role of U1 Small Nuclear Ribonucleoprotein in Spliceosome Assembly", *Science*, 1988, 242, 1028–1035.

Sigman, D. S. et al., "Nuclease Activity of 1,10–Phenanthroline–Copper Ion", *Acc. Chem. Res.*, 1986, 19, 180–186.

Smith, C. C. et al., "Antiviral effect of an oligo(nucleoside methylphosphonate) complementary to the splice junction of herpes simplex virus type 1 immdiate early re–mRNAs 4 and 5", *Proc. Natl. Acad. Sci.*, 1986, 83, 2787–2791.

Stein, C. A. et al., "Physiochemical proterties of phosphorothioate oligodeoxynucleotides", *Nucl. Acids Res.*, 1988, 16, 3209–3221.

Suciu, N. et al., "Synthesis of 9–(2, 5dideoxy–β–D–glycero–pent–3–enofuranosyl) adenine", *Carbohydrate Res.*, 1975, 44, 112–115.

Tidd, et al., "Evaluation of N–ras oncogene anti–sense, sense and nonsense sequence methylphosphonate oligonucleotide analogues", *Anti–Cancer Drug Design*, 1988, 3, 117–127.

Walder, R. et al., "Role of RNase H in hybrid–arrested translation by antisense oligonucleotides", *Proc. Natl. Acad. Sci.*, 1988, 85, 5011–5015.

Yeung, A. T. et al., "Photoreactivities and Thermal Properties of Psoralen Cross–Links", *Biochemistry*, 1988, 27, 3204–3210.

Zon, G., "Synthesis of Backbone–Modified DNA analogues for Biological Applications", *J. Protein Chem.*, 1987, 6, 131–145.

Monia, B. P. et al., "Selective Inhibition of Mutant Ha–ras mRNA Expression by Antisense Oligonucleotides", *J. Biol. Chem.*, 1992, 267, 19954–19962.

Daaka et al., *Oncogene Res.*, 1990, 5, 267–275.

Bos et al., *Mutation Res.*, 1988, 195, 255–271.

Feramisco, et al., "Transient reversion of ras oncogene–induced cell transformation by antibodies specific for amino acid 12 of ras protein", *Nature*, 1985, 314, 639–642.

Holt, et al., "An Oligomer Complementary to c–myc mRNA Inhibits Proliferation of HL–60 Promyelocytic Cells and Induces Differentiation", *Mol Cell. Biol.*, 1988, 8, 963–973.

Anfossi, et al., "An Oligomer complementary to c–myb–encoded mRNA inhibits proliferation of human myeloid leukemia cells lines", *Proc. Natl. Acad. Sci.*, 1989, 86, 3379–3383.

Wickstrom, et al., "Human promyelocytic leukemia HL–60 cell proliferation and c–myc protein expression are inhibited by an antisense pentadecadeoxynucleotide targeted against c–myc mRNA", *Proc. Natl. Acad. Sci.,* 1988, 85, 1028–1032.

Chang, et al., "Comparative inhibition of ras p21 protein synthesis with phosphorus–modified antisense oligonucleotides", *Anticancer Drug Design,* 1989, 4, 221–232.

Puglisi and Tinoco, [22] Absorbance Melting Curves of RNA, *Meth. In Enzym.,* 1989, 180, 304–325.

Petersheim, et al., "Base–Stacking and Base–Pairing Contributions to Helix Stability: thermodynamics of Double Helix formation with CCGG, CCGGp, CCGGAp, ACCGGp, CCGGUp, and ACCGGUp", *Biochem.,* 1983, 22, 256–263.

Borer, et al., "Stability of Ribonucleic acid Double–stranded Helices", *J. Mol. Biol.,* 1974, 86, 843–853.

Kingston, R. E., *Current Protocols in Molecular Biology,* 1990, F. M. Ausubel, et al., et al., Eds., John Wiley and Sons, NY.

Stein et al., *Science,* 1993, 261, 1004–1012.

Agrawal, S., et al., "Site–specific excision from RNA H and mixed–phosphate–backbone oligodeoxynucleotides", *Proc. Natl. Acad. Sci. USA,* 1990, 87, 1401–1405.

Dignam, et al., "Accurate transcription initiation by RNA polymerase II in a soluble extract from isolated mammalian nuclei", *Nuc. Acids Res.,* 1983, 5, 1475–1489.

Lima et al., "Implication of RNA Structure on Antisense Oligonucleotide Hybridization Kinetics", *Biochemistry,* 1992, 31, 12055–12061.

Wu, T. et al., "Prevention of Chain Cleavage in the Chemical Synthesis of 2'–silyated Oligonucleotides", *Nucl. Acids Res.,* 1989, 17, 3501–3517.

Capon, et al., "Complete nucleotide sequences of the T24 human bladder carcinoma oncogene and its normal homologue", *Nature,* 1983, 302, 33–37.

Chang, et al., "Antisense inhibition of ras p21 expression that is sensitive to a point mutation", *Biochemistry,* 1991, 30, 8283–8286.

Chartier–Harlin, et al., "Early–onset Alzheimer's disease caused by mutations at codon 717 of the β–amyloid precursor protein gene", *Nature,* 1991, 353, 844–846.

Furdon, et al., "RNase H cleavage of RNA hybridized to oligonucleotides containing methylphosphonate, phosphorothioate and phosphodiester bonds", *Nucleic Acids Research,* 1989, 17, 9193–9204.

Giles, et al., "Enhanced RNase H activity with methylphosphonodiester/phosphodiester chimeric antisense oligodeoxynucleotides", *Anti–Cancer Drug Design,* 1992, 7, 37–48.

Goate, et al., "Segregation of a missense mutation in the amyloid precursor protein gene with familial Alzheimer's disease", *Nature,* 1991, 349, 704–706.

Hall and Brown, "Human N–ras: cDNA cloning and gene structure", *Nucleic Acids Res.,* 1985, 13, 5255–5268.

Hayase, et al., "Secondary Structure in Formylmethionine tRNA Influences the Site–Directed Cleavage of Ribonuclease H Using Chimeric 2'–O–Methyl Oligodeoxyribonucleotides", *Biochemistry,* 1990, 29, 8793–8797.

Kahn, et al., "The c–ras Gene and Human Cancer (Review)", *Anticancer Res.,* 1987, 7, 639–652.

Murrel, et al., "A mutation in the Amyloid Precursor Protein Associated with Hereditary Alzheimer's Disease", *Science,* 1991, 254, 97–99.

Inoue, H. et al., "Sequence–dependent hydrolysis of RNA using Modified oligonucleotide splints and RNase H", *FEBS Letts.,* 1987, 215, 327–330.

Owen, et al., "Transcriptional activation of a conserved sequence element by ras requires a nuclear factor distinct from c–fos or c–jun", *Proc. Natl. Acad. Sci.,* 1990, 87, 3866–3870.

Nielsen, P. E. et al., "Sequence–Selective Recognition of DNA by Strand Displacement with a Thymine–Substituted Polyamide", *Science,* 1991, 254, 1497–1500.

Potts, et al., "Epithelial–mesenchymal transformation of embryonic cardiac endothelial cells is inhibited by a modified antisense oligodeoxynucleotide to transforming growth factor β3", *Proc. Natl. Acad. Sci. USA,* 1991, 88, 1516–1520.

Quartin, et al., "Number and distribution of methylphosphonate linkages of oligodeoxynucleotides affect exo–and endonuclease sensitivity and ability to form Rnase substrates", *Nucleic Acids Research,* 1989, 17, 7253–7262.

Reddy, et al., "A point mutation is responsible for the acquisition of transforming properties by the T24 human bladder carcinoma oncogene", *Nature,* 1982, 300, 149–152.

Schmidt, et al., "The use of oligonucleotide probes containing 2'–deoxy–2'–fluoronucleosides for regiospecific cleavage of RNA by RNase H from *Escherichia coli*", *Biochim. Biophys. Acta.,* 1992, 1130, 41–46.

Tabin, et al., "Mechanism of activation of a human oncogene", *Nature,* 1982, 300, 143–148.

Taparowsky, et al., "Activation of the T24 bladder carcinoma transforming gene is linked to a single amino acid change", *Nature,* 1982, 300, 762–765.

Stull, R.A. et al., "Antigene, Ribozyme and Aptamer Nucleic Acid Drugs: Progress and Prospects", *Pharmac. Res,* 1995, 12, 465–482.

Christofferson et al., "Ribozymes as human therapeutic agents", *J. Med. Chem.,* 1995, 38(12), 2023–2037.

San et al., "Safety and short term toxicity of a novel cationic lipid formulation for Human Gene therapy", *Hum. Gene. Therapy,* 1993, 4, 781–788.

Bhat et al., "A Simple and Convenient Method for the Selective N–Acylations of Cytosine Nucleosides", *Nucleosides & Nucleotides,* 1989, 8, 179–183.

Gaffney, B. L. et al., "A New Strategy for the Protection of Deoxyguanosine During Oligonucleotide Synthesis", *Tetrahedron Letts.,* 1982, 23, 2257–2260.

Graham, M. J. et al., "Tritium labeling of antisense oligonucleotides by exchange with tritiated water", *Nucl. Acids Res.,* 1993, 21, 3737–3743.

Reese et al., "4–(1,2,4–Triazol–1–yl)– and 4–(3–Nitro 1,2, 4–triazol–1–yl)–1–(β–D–2,3,5–tri–O–acetylarabinofuranosyl)pyrimidin–2 (1H)–ones. Valuable Intermediates in the Synthesis of Derivatives of 1–(β–D–Arabinofuranosyl) cytosine (Ara–C)", *J. Chem. Soc. Perkin Trans. I,* 1982, 1171–1176.

Sambrook, J. et al., "Labeling of Synthetic oligonucleotides by Phosphorylation with Bacteriophage T4 Polynucleotide Kinase", *Molecular Cloning: A Laboratory Manual,* 1989, Cold Spring Harbor Laboratory Press, 11.31–11.32.

Schwartz, O. et al., "A microtransfection method using the luciferase–encoding reporter gene for the assay of human immunodeficiency virus LTR promoter activity", *Gene,* 1990, 88, 197–205.

Seela et al., "Palindromic Octa– and Dodecanoucleotides Containing the 2' Deoxytubercidin: Syntheisis, Hairpin Formation, and Recognition by the Endodeoxyribonuclease", *Biochemistry*, 1987, 26, 2233–2238.

Stein, C.A. et al., "Oligodeoxynucleotides as Inhibitors of Gene Expression: A Review", *Cancer Res.*, 1988, 48, 2659–2668.

Arnott, S. et al., "Optimised Parameters for A–DNA and B–DNA", *Biochem. & Biophys. Res. Comm.*, 1972, 47, 1504–1510.

Beaucage, S. L. et al., "Deoxynucleoside Phosphoramidites–A New Class of Key Intermediates for Deoxypolynucleotide Synthesis", *Tetrahedron Letts.*, 1981, 22, 1859–1862.

Beaucage, S. L. et al., "3H–1,2–Benzodithiole–3–one 1,1–Dioxide as Improved Sulfurizing Reagent in the Solid Phase Synthesis of Oligodeoxyribonucleoside Phosphorothiates", *J. Am. Chem. Soc.*, 1990, 112, 1253–1254.

Butke, G. et al., "Facile Synthesis of 2'–Amino–2'–Deoxynucleoside from the Corresponding Arabino Derivative", *Nucleic Acid Chemistry,* Townsend, L. B. et al., eds., 1986, John Wiley & Sons, New York, 149–152.

Chen, Q.Y. et al., "Studies on Fluoroalkylation and Fluoroalkoxylation. Part 33. Direct Trifluoromethylation of Aryl Halides with Fluorosulphonyldiflyoromethyl Iodide in the Presence of Copper: an Electron Transfer Induced Process", *J. Chem. Soc. Perkin Trans. I,* 1989, 2385–2387.

Chladek et al., "Facile Synthesis of 2'–Amino–2'–Deoxyadenosine", *J. carbohydrates, Nucleosides & Nucleotides,* 1980, 7, 63–75.

Eckstein et al., "Polynucleotides Containing 2'–Chloro2'–eoxyribose", *Biochemistry,* 1972, 11, 4336–4344.

Fox et al., Nucleosides. XVIII. Synthesis of 2'–Fluorothymidine, 2'–Fluorodeoxyuridine, nd other 2'–Halogeno–2'–Deoxy Nucleosides, *J. Org. Chem.,* 1964, 29, 558–564.

Guschlbauer, W. et al., "Nucleoside conformation is determined by the electronegativity of the sugar substituent", *Nucl. Acids Res.,* 1980, 8, 1421–1433.

Hansske, F. et al., "2' and 3'–Ketonucleosides and their Arabino and Xylo Reduction Products", *Tetrahedron,* 1984, 40, 125–135.

De las Heras et al., "3'–C–Cyano–3'–Deoxythymidine", *Tetrahedron Letts.,* 1988, 29, 941–944.

Hertel, L. W. et al., "Synthesis of 2'–Deoxy–2,2–difluoro––D–ribose and 2'–Deoxy–2,2–difluoro–D–ribofuranosyl Nucleosides", *J. Org. Chem.,* 1988, 53, 2406–2409.

Ikehara, M. et al., "Polynucleotides. LVI. Synthesis and properties of poly(2'–deoxy–2'–fluroadenylic acid)", *Nucl. Acids Res.,* 1978, 5, 3315–3325.

Ikehara, M., "Purine 8–Cyclonucleosides", *Accts. Chem. Res.,* 1969, 2, 47–53.

Ikehara, M. et al., "Purine Cyclonucleosides–26 A Versatile Method for the Synthesis of Purine O–Cyclo–Nucleosides", *Tetrahedron,* 1975, 31, 1369–1372.

Ikehara, M. et al., "Studies of Nucleosides–and Nucleotides—LXXIV", *Tetrahedron,* 1978, 34, 1133–1138.

Ikehara, M. et al., "Studies of Nucleosides–and Nucleotides—LXXXII. Cyclonucleosides. (39). Synthesis and Properties of 2'–Halogeno–2'–deoxyadenosines", *Chem. Pharm. Bull.,* 1978, 26, 2449–2453.

Ikehara, M. et al., "Studies of Nucleosides–and Nucleotides—LXXXIX. Purine Cyclonucleosides. (43). Synthesis and Properties of 2'–Halogeno–2'–deoxyguanosines", *Chem. Pharm. Bull.,* 1981, 29, 3281–3285.

Ikehara, M. et al., "Improved Synthesis of 2'–fluoro2'–deoxyadenosine and Synthesis and Carbon–13 NMR Spectrum of its 3',5'–cyclic Phosphate Derivatives", *Nucleosides & Nucleotides,* 1983, 2, 373–385.

Ikehara, M. et al., "A Linear Relationship Between Electronegativity of 2'–Substituents and Conformation of Adenine Nucleosides", *Tetrahedron Letts.,* 1979, 42, 4073–4076.

Ikehara, M. et al., "Recognition by restriction endonclease EcoR1 of deoxyoctanucleotides containing modified sugar moieties", *Eur. J. Biochem.,* 1984, 139, 447–450.

Imazawa, M. et al., "Nucleosides–and Nucleotides. XII. Synthesis and Properties of 2'–Deoxy–2'–mercaptouridine and Its Derrivatives", *Chem. Pharm. Bull.,* 1975, 23, 604–610.

Jones, G. H. et al., "Transient protection: Efficient one–flask synthesis of protected deoxynucleosides", *J. Am. Chem. Soc.,* 1982, 104, 1316–1319.

Koole, L. H. et al., "Enhanced stability of a Watson & crick DNA duplex structure by methylation of the phosphate groups in one strand", *Chemistry Proceedings B,* 1987, 90, 41–46.

Markiewicz et al., "Simultaneous Protection of 3'– and 5'–Hydroxyl Groups of Nucleosides", *Nucleic Acid Chemistry,* 1981, L. B. Townsend et al., Ed.s, Part 3, J. Wiley and Sons, NY, 222–231.

Ogilvie et al., "Solution and solid phase chemical synthesis of arabinocucleotides", *Can. J. Chem.,* 1989, 831–839.

Caruthers, M. H., "Synthesis of Oligonucleotides and Oligonucleotide Analogues", *Oligonucleotides: Antisense Inhibitors of Gene Expression,* 1989, Chapter 1, Cohen, J. S. (Ed.), CRC Press, Boca Raton, FL, 7–24.

Ranganathan, R., "Modification of the 2'–Position of Purine Nucleosides: Syntheisi of 2'–α–Substituted–2'–deoxyadenosine Analogs", *Tetrahedron Letts.,* 1977, 15, 1291–1294.

Rao, T. S. et al., "A Novel One–step Procedure for the Conversion of Thymidine into 2,3'–Anhydrothymidine", *J. Chem. Soc. Chem. Commun.,* 1989, 997–998.

Robins, M. J. et al., "Nucleic acid related compounds. 41. Restricted furanose conformations of 3',5'–O–(1,1,3,3–tetraisopropyldisilox–1,3–diyl) nucleosides provide a convenient evaluation of anomeric configuration", *Can. J. Chem.,* 1983, 61, 1911–1920.

Shibahara, S. et al., "Inhibition of human immunodeficiency virus (HIV–1) replication by synthetic oligo–RNA derivatives", *Nucl. Acids Res.,* 1989, 17, 239–252.

Sproat, B. S. et al., "Highly efficient chemical synthesis of 2'–O–methyloligoribonucleotides and tetrabiotinylated derrivatives; novel proobes that are resistant to degradation by RNA or DNA specific nucleases", *Nucl. Acids Res.,* 1989, 17, 3373–3386.

Sproat, B. S. et al., "New synthetic routes to protected purine 2–O–methylriboside–3'–O–phosphoramidites using a novel alkylation procedure", *Nucl. Acids Res.,* 1990, 18, 41–49.

Divakar, K. J. et al., "Approaches to the Synthesis of 2'–Thio Anologues of Pyrimidine Ribosides", *J. Chem. Soc. Perkins Trans.,* 1990, 1, 969–974.

Ryan, K. J. et al., "Synthesis of 2–Thio–D–ribose and 2'–Thioadenosine Derivatives", *J. Org. Chem.*, 1971, 36, 2646–2657.

Stufkins et al., Dynamic Jan–Teller Effect in the Excited States of $SeCl_6^{2-}$, $TeCl_6^{2-}$, and $TeBr_6^{2-}$, *Recueil des Travaux Chemiques des Pays–Bas*, 1970, 89, 1185–1201.

Zon, G., "Oligonucleotide Analogues as Potential Chemotherapeutic Agents", *Pharm. Res.*, 1988, 5, 539–547.

Walder, "Antisense DNA and RNA: progress and prospects", *Genes & Dev.*, 1988, 2, 502–504.

Marcus–Sekura, C. J., "Techniques for Using Antisense Oligodeosyribonucleotides to Study Gene Expression", *Analyt. Biochem.*, 1988, 172, 289–295.

Agarwal et al., "Synthesis and Enzymatic Properties of Deoxyriboologonucleotides Containing Methyl and Phenylphosphonate Linkages", *Nucl. Acids Res.*, 1979, 6, 3009–3024.

Miller, P. S. et al., "Nonionic Nucleic Acid Analogues. Synthesis and Characterization of Dideoxyribonucleoside Methylphosphonates", *Biochem.*, 1979, 18, 5134–5143.

Jäger, A. et al., "Oligonucleotide N–Alkylphosphoramidates: Synthesis and Binding to Polynucleotides", *Biochem.*, 1988, 27, 7237–7246.

Knorre, D. G. et al., "Complemetary–Addressed (Sequence–Specific) Modification of Nucleic Acids", 1985, 32, 291–321.

Weissberger, A., Ed., "Imidazole and its Derivatives", *The Chemistry of Heterocyclic Compounds*, 1953, Interscience Publishers, Inc., New York, 447.

Jones, G. H. et al., "4'–Substituted Nucleosides. 5. Hydroxymethylation of Nucleoside 5'–Aldehydes", *J. Org. Chem.*, 1979, 44,1309–1317.

Robins, M. J. et al., "Synthesis of 2'–Deoxytubercidin, 2'–deoxyadenosine, and Related 2'–Deoxynucleosides via Novel Direct Stereospecific Sodium Salt Glycosylation Procedure", *J. Am. Chem. Soc.*, 1984, 106, 6379–6382.

Ikehara, M. et al., "Studies of Nucleosides and Nucleotides—LXXXVII. Purine Cyclonucleosides. XLII. Synthesis of 2'–deoxy–2'–fluorofunaosine", *Chem. Pharm. Bull.*, 1981, 29, 1034–1038.

Bhat, et al., "Synthesis of Novel Nucleic Acid Mimics via the Stereoselective Intermolecular Radical Coupling of 3'–Iodo Nucleosides and Formadoximes", *J. Org. Chem.*, 1996, 61, 8186–8199.

Brown, et al., "Modulation of ras Expression of Anti–sense, Nonionic Deoxyoligonucleotide Analogs", *Oncogene Research*, 1989, 4, 243–252.

Georges, et al., "Prevention of Orthotopic Human Lung Cancer Growth by Intratracheal Instillation of a Retroviral Antisense K–ras Construct", *Cancer Research*, 1993, 53, 1743–1746.

Martin, et al., "Ein neuer Zugang zu 2'–O–Alkylribonucleosiden und eigenschaften deren Oligonucleotide", *Helvetica Chimica Acta*, 1995, 78, 486–504.

McGrath, et al., "Structure and organization of the human Ki–ras proto–oncogene and a related processed pseudogene", *Nature*, 1983, 304, 501–506.

Mukhopadhyay, et al., "Specific Inhibition of K–ras Expression and Tumorigenicity of Lung Cancer Cells by Antisense RNA", *Cancer Research*, 1991, 51, 1744–1748.

Inoue, et al., "Sequence–dependent hybrolysis of RNA using modified oligonucleotide splints and Rnase H",*FEBS Lett.*, 1987, 215, 327–330.

Perbost, et al., "Synthesis of 5'–O–Amino–2'–deoxypyrimidine and Purine Nucleosides: Building–Blocks for Antisense Oligonucleosides", *J. Org. Chem.*, 1995, 60, 5150–5156.

Musicki and Widlanski, "Synthesis of Nucleoside Sulfonates and Sulfones", *Tetrahedron Letters*, 1991, 32, 1267–1270.

Ogilvie and Cormier, "Synthesis of a thymidine Dinucleotide Analogue Containing an Internucleotide Silyl Linkage", *Tetrahedron Letters*, 1985, 26, 4159–4162.

Tronchet, J. M. J., et al., "Blocked Disaccharide Analogs Bearing an Oxyimino Interglycosidic Bridge", *J. Carbohydrate Chem.*, 1991, 10(4), 723–728.

Mungall, W. S. and Kaiser, J. K., "Carbamate Analogues of Oligonucleotides", *J. Org. Chem.*, 1977, 42, 703–706.

Stirchak, E. P. et al., "Uncharged stereoregular nucleic acid analogs: 2. Morpholino nucleoside oligomers with carbamate internucleoside linkages", *Nucleic Acids Res.*, 1989, 17, 6129–6134.

Kirschenbaum, et al., Novel Oligonucleotide Analogues with Sulfur–Based Linkage, The Fifth San Diego Conference on Nucleic Acids: New Frontiers, Poster Abstract 28, Nov. 16–19, 1990; Abstract CD210.

Shum, et al., Third chemical Congress of North America, Organic Chemistry, 1988, Synthesis of 3',5'–Bis(Deoxythymidylyl) Difluoromethylphosphonate, Canada, Jun. 5–10, 1988, Abstract No. 319.

Kawai, et al., Third Chemical Congress of North America, Organic Chemistry, 1988, Single–Stranded DNA & RNA Binding: Backbone–Modified Polynucleotide Analogues, Canada, Jun. 5–10, 1988, Abstract No. ORGN 318.

Musicki, B. And Widlanski, T. S., "Synthesis of Carbohydrate sulfonates and Sulfonate Esters",*J. Org. Chem.*, 1987, 55, 4231–4233.

Huang, Z, et al., "Non–ionic Antisense Oligonucleotides Containing Sulfide and Sulfone Linkages in Place of Phosphodiester Groups in Natural Oligonucleotides", *J. Of Cellular Biochemistry, Abstracts, 20th Annual Meeting*, 1991, CD209.

\* cited by examiner ggcccugaggagcgAUGacggaauuaagcugguggugggget gccgUcggugugggcaagagugcgcug

| OLIGO | LENGTH | TARGET | IC50 (uM) | SELECTIVITY |
|---|---|---|---|---|
| 2502 | 20 | AUG | 0.75 | NONE |
| 2503 | 20 | AUG | 0.05 | NONE |
| 2563 | 5 | POINT | NOT ACTIVE | --- |
| 2564 | 7 | POINT | NOT ACTIVE | --- |
| 2565 | 9 | POINT | NOT ACTIVE | --- |
| 2567 | 11 | POINT | NOT ACTIVE | --- |
| 2568 | 13 | POINT | NOT ACTIVE | --- |
| 2569 | 15 | POINT | NOT ACTIVE | --- |
| 2570 | 17 | POINT | 0.10 | 2-3x |
| 2571 | 19 | POINT | 0.25 | NONE |
| 2566 | 21 | POINT | 0.25 | NONE |
| 2560 | 23 | POINT | 0.75 | NONE |
| 2561 | 25 | POINT | 1.00 | NONE |

*Fig. 4a*

| ISIS 2503 | TCCGTCATCGCTCCTCAGGG | Positive control, P=S |
| ISIS 13177 | TTAGTAATAGCCCCACATGG | Scrambled control, P=S |
| ISIS 14896 | TCCGTCATCGCTCCTCAGGG | MMI(1+1), P=S |
| ISIS 14898 | TCCGTCATCGCTCCTCAGGG | MMI(2+2), P=S |
| ISIS 14890 | TCCGTCATCGCTCCTCAGGG | MMI(3+3), P=S |
| ISIS 14897 | TCCGTCATCGCTCCTCAGGG | MMI(2+2), P=O |
| ISIS 14899 | TCCGTCATCGCTCCTCAGGG | MMI(3+3), P=O |

P=S =phosphorothioate; P=O =phosphodiester

```
ISIS  2503     TCCGTCATCGCTCCTCAGGG     P=S
ISIS 13177     TTAGTAATAGCCCCACATGG     Scrambled control, P=S
ISIS 13920     TCCGTCATCGCTCCTCAGGG     MOE, P=S
ISIS 14896     TCCGTCATCGCTCCTCAGGG     MMI(1+1), P=S
ISIS 14898     TCCGTCATCGCTCCTCAGGG     MMI(2+2), P=S
```
P=S =phosphorothioate; MOE =methoxy ethyl;

SEQUENCE LISTING

<160> NUMBER OF SEQ ID NOS: 33

<210> SEQ ID NO: 1
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 1
cttatattcc gtcatcgctc                                                    20

<210> SEQ ID NO: 2
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 2
tccgtcatcg ctcctcaggg                                                    20

<210> SEQ ID NO: 3
<211> LENGTH: 17
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 3
ccacaccgac ggcgccc                                                       17

<210> SEQ ID NO: 4
<211> LENGTH: 19
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 4
cccacaccga cggcgccca                                                     19

<210> SEQ ID NO: 5
<211> LENGTH: 21
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 5
gcccacaccg acggcgccca c                                                  21

<210> SEQ ID NO: 6
<211> LENGTH: 23
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 6
tgcccacacc gacggcgccc acc                                    23

<210> SEQ ID NO: 7
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 7
tattccgtca tcgctcctca                                        20

<210> SEQ ID NO: 8
<211> LENGTH: 5
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 8 cgacg                                                         5

<210> SEQ ID NO: 9
<211> LENGTH: 7
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 9 ccgacgg                                                       7

<210> SEQ ID NO: 10
<211> LENGTH: 9
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 10 accgacggc                                                     9

<210> SEQ ID NO: 11
<211> LENGTH: 11
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 11
caccgacggc g                                                 11

<210> SEQ ID NO: 12
<211> LENGTH: 13
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 12
acaccgacgg cgc                                                      13

<210> SEQ ID NO: 13
<211> LENGTH: 15
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 13
cacaccgacg gcgcc                                                    15

<210> SEQ ID NO: 14
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 14
ccacaccgac ggcgcc                                                   16

<210> SEQ ID NO: 15
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 15
cacaccgacg gcgccc                                                   16

<210> SEQ ID NO: 16
<211> LENGTH: 18
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 16
cccacaccga cggcgccc                                                 18

<210> SEQ ID NO: 17
<211> LENGTH: 18
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 17
ccacaccgac ggcgccca                                                 18

<210> SEQ ID NO: 18
<211> LENGTH: 25
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 18
ttgcccacac cgacggcgcc cacca                                         25

```
<210> SEQ ID NO: 19
<211> LENGTH: 17
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 19
ccacaccgcc ggcgccc                                                    17

<210> SEQ ID NO: 20
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 20
ctgcctccgc cgccgcggcc                                                 20

<210> SEQ ID NO: 21
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 21
cagtgcctgc gccgcgctcg                                                 20

<210> SEQ ID NO: 22
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 22
aggcctctct cccgcacctg                                                 20

<210> SEQ ID NO: 23
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 23
ttcagtcatt ttcagcaggc                                                 20

<210> SEQ ID NO: 24
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 24
ttatattcag tcattttcag                                                 20
```

```
<210> SEQ ID NO: 25
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 25
caagtttata ttcagtcatt                                                     20

<210> SEQ ID NO: 26
<211> LENGTH: 21
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 26
gcctacgcca ccagctccaa c                                                   21

<210> SEQ ID NO: 27
<211> LENGTH: 17
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 27
ctacgccacc agctcca                                                        17

<210> SEQ ID NO: 28
<211> LENGTH: 21
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 28
gtactcctct tgacctgctg t                                                   21

<210> SEQ ID NO: 29
<211> LENGTH: 21
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 29
cctgtaggaa tcctctattg t                                                   21

<210> SEQ ID NO: 30
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 30
ggtaatgcta aaacaaatgc                                                     20
```

```
<210> SEQ ID NO: 31
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 31
ggaatactgg cacttcgagg                                                    20

<210> SEQ ID NO: 32
<211> LENGTH: 15
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 32
tacgccaaca gctcc                                                         15

<210> SEQ ID NO: 33
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 33
ttttcagcag gcctctctcc                                                    20
```

ANTISENSE INHIBITION OF RAS GENE WITH CHIMERIC AND ALTERNATING OLIGONUCLEOTIDES

RELATED APPLICATIONS

This application is a Div of Ser. No. 08/848,840, filed Apr. 30, 1997, now U.S. Pat. No. 5,965,722, which is a continuation-in-part of U.S. patent application Ser. No. 07/411,734, filed Sep. 25, 1989 now U.S. Pat. No. 4,945, 741. PCT Application PCT/US93/09346, filed Oct. 1, 1993; U.S. patent application Ser. No. 07/715,196, filed Jun. 14, 1991, now abandon; U.S. patent application Ser. No.: 07/958,134, filed Oct. 5, 1992, now abandon; U.S. patent application Ser. No. 292,086, filed Jul. 19, 1994, that issued as U.S. Pat. No. 5,582,986; U.S. patent application Ser. No.: 08/007,996, filed Jan. 21, 1993, now abandon; U.S. patent application Ser. No. 297,248, filed Jul. 26, 1994, that issued as U.S. Pat. No. 5,576,208; U.S. patent application Ser. No. 07/703,619, filed May 21, 1991, that issued as U.S. Pat. No. 5,378,825; U.S. patent application Ser. No. 08/040,903, filed Mar. 31, 1993, that issued as U.S. Pat. No. 5,386,023; U.S. patent application Ser. No. 07/040,526, filed on Apr. 20, 1987, that issued as U.S. Pat. No. 5,489,677; U.S. patent application Ser. No. 08/174,379, filed Dec. 28, 1993, that issued as U.S. Pat. No. 5,541,307; U.S. patent application Ser. No. 08/040,933, filed Mar. 31, 1993, now abandon; U.S. patent application Ser. No. 08/300,072, filed Sep. 2, 1994, that issued U.S. Pat. No. 5,618,704; U.S. patent application Ser. No. 08/039,979, filed Mar. 30, 1993, now abandon; U.S. patent application Ser. No. 08/395,168, filed Feb. 27, 1995, that issued as U.S. Pat. No. 5,623,070; U.S. patent application Ser. No. 07/814,961, filed Dec. 24, 1991, now abandon; PCT Patent Application PCT/US92/11339, filed Dec. 23, 1992; and U.S. patent application Ser. No. 08/244,993, filed Jun. 21, 1994, that issued as U.S. Pat. No. 5,623,065; and U.S. patent application Ser. No. 08/468,037, filed Jun. 6, 1995; now U.S. Pat. No. 5,859,221 each of which are incorporated herein by reference in their entirety.

FIELD OF THE INVENTION

This invention relates to compositions and methods for the inhibition of expression of the ras gene, a naturally occurring gene which occasionally converts to an activated form that has been implicated in tumor formation. This invention is also directed to the specific inhibition of expression of the activated form of the ras gene. This invention is further directed to the detection of both normal and activated forms of the ras gene in cells and tissues, and can form the basis for research reagents and kits both for research and diagnosis. Furthermore, this invention is directed to treatment of such conditions as arise from activation of the ras gene. This invention also relates to stabilized oligonucleotides for inhibition of expression of the ras gene, to such oligonucleotides which have been further modified to enhance their affinity for the ras RNA target, and to such oligonucleotides which have been still further modified to yield sequence-specific elimination of the ras RNA target.

BACKGROUND OF THE INVENTION

Alterations in the cellular genes which directly or indirectly control cell growth and differentiation are considered to be the main cause of cancer. There are some thirty families of genes, called oncogenes, which are implicated in human tumor formation. Members of one such family, the ras gene family, are frequently found to be mutated in human tumors. In their normal state, proteins produced by the ras genes are thought to be involved in normal cell growth and maturation. Mutation of the ras gene, causing an amino acid alteration at one of three critical positions in the protein product, results in conversion to a form which is implicated in tumor formation. A gene having such a mutation is said to be "activated." It is thought that such a point mutation leading to ras activation can be induced by carcinogens or other environmental factors. Over 90% of pancreatic adenocarcinomas, about 50% of adenomas and adenocarcinomas of the colon, about 50% of adenocarcinomas of the lung and carcinomas of the thyroid, and a large fraction of malignancies of the blood such as acute myeloid leukemia and myelodysplastic syndrome have been found to contain activated ras oncogenes. Overall, some 10 to 20% of human tumors have a mutation in one of the three ras genes (H-ras, K-ras, or N-ras).

It is presently believed that inhibiting expression of activated oncogenes in a particular tumor cell might force the cell back into a more normal growth habit. For example, Feramisco et al., *Nature* 1985, 314, 639–642, demonstrated that if cells transformed to a malignant state with an activated ras gene are microinjected with antibody which binds to the protein product of the ras gene, the cells slow their rate of proliferation and adopt a more normal appearance. This has been interpreted as support for the involvement of the product of the activated ras gene in the uncontrolled growth typical of cancer cells.

The H-ras gene has recently been implicated in a serious cardiac arrhythmia called long Q-T syndrome, a hereditary condition which often causes sudden death if treatment is not given immediately. Frequently there are no symptoms prior to the onset of the erratic heartbeat. Whether the H-ras gene is precisely responsible for long Q-T syndrome is unclear. However, there is an extremely high correlation between inheritance of this syndrome and the presence of a particular variant of the chromosome 11 region surrounding the H-ras gene. Therefore, the H-ras gene is a useful indicator of increased risk of sudden cardiac death due to the long Q-T syndrome.

There is a great desire to provide compositions of matter which can modulate the expression of the ras gene, and particularly to provide compositions of matter which specifically modulate the expression of the activated form of the ras gene. It is greatly desired to provide methods of diagnosis and detection of the ras gene in animals. It is also desired to provide methods of diagnosis and treatment of conditions arising from ras gene activation. In addition, improved research kits and reagents for detection and study of the ras gene are desired.

Inhibition of oncogene expression has been accomplished using retroviral vectors or plasmid vectors which express a 2-kilobase segment of the Ki-ras protooncogene RNA in antisense orientation. Mukhopadhyay, T. et al. (1991) *Cancer Research* 51, 1744–1748; PCT Patent Application PCT/US92/01852 (WO 92/15680); Georges, R. N. et al. (1993) *Cancer Research*, 53, 1743–1746.

Antisense oligonucleotide inhibition of oncogenes has proven to be a useful tool in understanding the roles of various oncogene families. Antisense oligonucleotides are small oligonucleotides which are complementary to the "sense" or coding strand of a given gene, and as a result are also complementary to, and thus able to stably and specifically hybridize with, the mRNA transcript of the gene. Holt et al., *Mol. Cell Biol.* 1988, 8, 963–973, have shown that antisense oligonucleotides hybridizing specifically with mRNA transcripts of the oncogene c-myc, when added to cultured HL60 leukemic cells, inhibit proliferation and induce differentiation. Anfossi et al., *Proc. Natl. Acad. Sci.* 1989, 86, 3379–3383, have shown that antisense oligonucleotides specifically hybridizing with mRNA transcripts of the c-myb oncogene inhibit proliferation of human myeloid leukemia cell lines. Wickstrom et al., *Proc. Nat. Acad. Sci.* 1988, 85, 1028–1032, have shown that expression of the protein product of the c-myc oncogene as well as proliferation of HL60 cultured leukemic cells are inhibited by antisense oligonucleotides hybridizing specifically with c-myc mRNA. U.S. Pat. No. : 4,871,838 (Bos et al.) discloses oligonucleotides complementary to a mutation in codon 13 of N-ras to detect said mutation. U.S. Pat. No. : 4,871,838 (Bos et al.) discloses molecules useful as probes for detecting a mutation in DNA which encodes a ras protein.

In all these cases, instability of unmodified oligonucleotides has been a major problem, as they are subject to degradation by cellular enzymes. PCT/US88/01024 (Zon et al.) discloses phosphorothioate oligonucleotides hybridizable to the translation initiation region of the amplified c-myc oncogene to inhibit HL-60 leukemia cell growth and DNA synthesis in these cells. Tidd et al., *Anti-Cancer Drug Design* 1988, 3, 117–127, evaluated methylphosphonate antisense oligonucleotides hybridizing specifically to the activated N-ras oncogene and found that while they were resistant to biochemical degradation and were nontoxic in cultured human HT29 cells, they did not inhibit N-ras gene expression and had no effect on these cells. Chang et al. showed that both methylphosphonate and phosphorothioate oligonucleotides hybridizing specifically to mRNA transcripts of the mouse Balb-ras gene could inhibit translation of the protein product of this gene in vitro. Chang et al., *Anti-Cancer Drug Design* 1989, 4, 221–232; Brown et al., *Oncogene Research* 1989, 4, 243–252. It was noted that $T_m$ was not well correlated with antisense activity of these oligonucleotides against in vitro translation of the ras p21 protein product. Because the antisense oligonucleotides used by Chang et al. hybridize specifically with the translation initiation region of the ras gene, they are not expected to show any selectivity for activated ras and the binding ability of these oligonucleotides to normal (wild-type) vs. mutated (activated) ras genes was not compared.

Helene and co-workers have demonstrated selective inhibition of activated (codon 12 G→T transition) H-ras mRNA expression using a 9-mer phosphodiester linked to an acridine intercalating agent and/or a hydrophobic tail. This compound displayed selective targeting of mutant ras message in both Rnase H and cell proliferation assays at low micromolar concentrations. Saison-Behmoaras, T. et al., *EMBO J.* 1991, 10, 1111–1118. Chang and co-workers disclose selective targeting of mutant H-ras message; this time the target was H-ras codon 61 containing an A→T transversion and the oligonucleotide employed was either an 11-mer methylphosphonate or its psoralen derivative. These compounds, which required concentrations of 7.5–150 $\mu$M for activity, were shown by immunoprecipitation to selectively inhibit mutant H-ras p21 expression relative to normal p21. Chang et al., *Biochemistry* 1991, 30, 8283–8286.

Modified nucleotides which increase $\Delta\Delta G°_{37}$ for base mismatches can be used to increase selectivity. It has been found that $\Delta\Delta G°_{37}$ ranges from 1–2 kcal/mol for the most stable mismatches to 5–6 kcal/mol for the least stable mismatches. When possible, therefore, to maximize selectivity for the mutant target, mutations that generate stable mismatches (e.g., G→A) are less preferred than mutations that generate unstable mismatches (e.g., C→G, U→G, A→C). An example of this can be found in the autosomal dominant mutations associated with familial Alzheimer's disease. Three different point mutations of the β-amyloid precursor gene have been shown to cosegregate with this disease. These mutations include G→A ($\Delta\Delta G°_{37}$=+1.2 kcal/mol), G→T ($\Delta\Delta G°_{37}$=+3.9 kcal/mol), and T→G ($\Delta\Delta G°_{37}$=+6.3 kcal/mol)[2]. Goate et al., *Nature* 1991, 349, 704–706; Murrel et al., *Science* 1991, 254, 97–99; Chartier-Harlin et al., *Nature* 1991, 353, 844–846. In this case, targeting the T→G mutation is believed to yield the greatest selectivity for mutant β-amyloid by an antisense oligonucleotide.

DNA oligonucleotides having unmodified phosphodiester internucleoside linkages or modified phosphorothioate internucleoside linkages are substrates for cellular RNase H; i.e., they activate the cleavage of target RNA by the RNase H. (Dagle, J. M, Walder, J. A. and Weeks, D. L., *Nucleic Acids Research* 1990, 18, 4751; Dagle, J. M., Weeks, D. L. and Walder, J. A., *Antisense Research And Development* 1991, 1, 11; and Dagle, J. M., Andracki, M. E., DeVine, R. J. and Walder, J. A., *Nucleic Acids Research* 1991, 19, 1805). RNase H is an endonuclease that cleaves the RNA strand of RNA:DNA duplexes; activation of this enzyme therefore results in cleavage of the RNA target, and thus can greatly enhance the ability of antisense oligonucleotides to inhibit target RNA expression. Walder et al. note that in Xenopus embryos, both phosphodiester linkages and phosphorothioate linkages are also subject to exo-nuclease degradation. Such nuclease degradation is detrimental since it rapidly depletes the oligonucleotide available for RNase H activation. PCT Publication WO 89/05358, Walder et al., discloses DNA oligonucleotides modified at the 3' terminal internucleoside linkage to make them resistant to nucleases while remaining substrates for RNAse H.

Attempts to take advantage of the beneficial properties of oligonucleotide modifications while maintaining the substrate requirements for RNase H have led to the employment of chimeric oligonucleotides. Giles, R. V. et al., *Anti-Cancer Drug Design* 1992, 7, 37; Hayase, Y. et al., *Biochemistry* 1990, 29, 8793; Dagle, J. M. et al., *Nucleic Acids Research* 1990, 18, 4751; Dagle, J. M. et al., *Nucleic Acids Research* 1991, 19, 1805. Chimeric oligonucleotides contain two or more chemically distinct regions, each comprising at least one nucleotide. These oligonucleotides typically contain a region of modified nucleotides that confer one or more beneficial properties (such as, for example, increased nuclease resistance, increased uptake into cells, increased binding affinity for the RNA target) and an unmodified region that retains the ability to direct RNase H cleavage. This approach has been employed for a variety of backbone modifications, most commonly methylphosphonates, which alone are not substrates for RNAse H. Methylphosphonate oligonucleotides containing RNase H-sensitive phosphodiester linkages were found to be able to direct target RNA cleavage by RNase H in vitro. Using *E. coli* RNase H, the minimum phosphodiester length required to direct efficient RNase H cleavage of target RNA strands has been reported to be either three or four linkages. Quartin, R. S. et al. *Nucleic Acids Research* 1989, 17, 7253; Furdon, P. J. et al. *Nucleic Acids Research* 1989, 17, 9193. Similar studies have been reported using in vitro mammalian RNase H cleavage assays. Agrawal, S. et al., *Proc. Natl. Acad. Sci. USA* 1990, 87, 1401. In this case, a series of backbone modifications, including methylphosphonates, containing different phosphodiester lengths were examined for cleavage efficiency. The minimum phosphodiester length required for efficient RNase H cleavage directed by oligonucleotides of this nature is five linkages. More recently, it has been shown that methylphosphonate/phosphodiester chimeras display increased specificity and efficiency for target RNA cleavage using *E. coli* RNase H in vitro. Giles, R. V. et al., *Anti-Cancer Drug Design* 1992, 7, 37. These compounds have also been reported to be effective antisense inhibitors in Xenopus oocytes and in cultured mammalian cells. Dagle, J. M. et al., *Nucleic Acids Res.* 1990, 18, 4751; Potts, J. D., et al., *Proc. Natl. Acad. Sci. USA* 1991, 88, 1516.

PCT Publication WO 90/15065, Froehler et al., discloses chimeric oligonucleotides "capped" at the 3' and/or the 5' end by phosphoramidite, phosphorothioate or phosphorodithioate linkages in order to provide stability against exonucleases while permitting RNAse H activation. PCT Publication WO 91/12323, Pederson et al., discloses chimeric oligonucleotides in which two regions with modified backbones (methyl phosphonates, phosphoromorpholidates, phosphoropiperazidates or phosphoramidates) which do not activate RNAse H flank a central deoxynucleotide region which does activate RNAse H cleavage. 2'-deoxy oligonucleotides have been stabilized against nuclease degradation while still providing for RNase H activation by positioning a short section of phosphodiester linked nucleotides between sections of backbone-modified oligonucleotides having phosphoramidate, alkylphosphonate or phosphotriester linkages. Dagle, J. M, Walder, J. A. and Weeks, D. L., *Nucleic Acids Research* 1990, 18, 4751; Dagle, J. M., Weeks, D. L. and Walder, J. A., *Antisense Research And Development* 1991, 1, 11; and Dagle, J. M., Andracki, M. E., DeVine, R. J. and Walder, J. A., *Nucleic Acids Research* 1991, 19, 1805. While the phosphoramidate containing oligonucleotides were stabilized against exonucleases, each phosphoramidate linkage resulted in a loss of 1.6° C. in the measured $T_m$ value of the phosphoramidate containing oligonucleotides. Dagle, J. M., Andracki, M. E., DeVine, R. J. and Walder, J. A., *Nucleic Acids Research* 1991, 19, 1805. Such loss of the $T_m$ value is indicative of a decrease in the hybridization between the oligonucleotide and its target strand.

Saison-Behmoaras, T., Tocque, B. Rey, I., Chassignol, M., Thuong, N. T. and Helene, C., *EMBO Journal* 1991, 10, 1111, observed that even though an oligonucleotide was a substrate for RNase H, cleavage efficiency by RNase H was low because of weak hybridization to the mRNA.

Chimeric oligonucleotides are not limited to backbone modifications, though chimeric oligonucleotides containing 2' ribose modifications mixed with RNase H-sensitive deoxy residues have not been as well characterized as the backbone chimeras. EP Publication 260,032 (Inoue et al.) and Ohtsuka et al., *FEBS Lett.* 1987, 215, 327–330, employed 2'-O-methyl oligonucleotides (which alone would not be substrates for RNAse H) containing unmodified deoxy gaps to direct cleavage in vitro by *E. coli* RNase H to specific sites within the complementary RNA strand. These compounds required a minimum deoxy gap of four bases for efficient target RNA cleavage. However, oligonucleotides of this nature were not examined for cleavage efficiency using mammalian RNase H nor tested for antisense activity in cells. These oligonucleotides were not stabilized against nucleases.

Studies on the ability to direct RNase H cleavage and antisense activity of 2' ribose modifications other than O-methyl have been extremely limited. Schmidt, S. et al., *Biochim. Biophys. Acta* 1992, 1130, 41.

While it has been recognized that cleavage of a target RNA strand using an antisense oligonucleotide and RNase H would be useful, nuclease resistance of the oligonucleotide and fidelity of the hybridization are also of great importance. There has been a long-felt need for methods or materials that could both activate RNase H while concurrently maintaining or improving hybridization properties and providing nuclease resistance. There remains a long-felt need for such methods and materials for enhancing antisense activity.

OBJECTS OF THE INVENTION

It is an object of the invention to provide oligonucleotides complementary to ras mRNA which inhibit expression of the ras gene.

It is another object of the invention to provide oligonucleotides complementary to ras mRNA which specifically inhibit expression of an activated (mutant) form of the ras gene.

Yet another object of the invention is to provide stabilized oligonucleotides which inhibit expression of the ras gene.

Another object of the invention is to provide stabilized oligonucleotides complementary to ras mRNA and modified to increase their affinity for the ras mRNA target, which inhibit expression of the ras gene.

Still another object is to provide oligonucleotides which are complementary to ras mRNA and which are substrates for RNAse H.

An additional object of the invention is to provide oligonucleotides which inhibit proliferation of cancer cells. Methods of inhibiting proliferation of cancer cells are also an object of this invention.

Detection of the mutation from the normal (wild-type) to activated form of the ras gene is another object of the invention.

Differential diagnosis of morphologically similar tumors and identification of high-risk conditions based on the presence of the activated ras gene is yet another object of this invention.

A further object of this invention is to provide methods of diagnosis and treatment of conditions arising due to mutation of the gene from the wild-type to the mutant, activated form of the ras gene.

SUMMARY OF THE INVENTION

In accordance with the present invention oligonucleotides having modified internucleosidic linkages or modified nucleosidic units are provided that are complementary to DNA or RNA. In one preferred embodiment, oligonucleotides that are complementary to DNA or RNA deriving from the human H-ras gene are provided. In certain preferred oligonucleotides of the invention are oligonucleotides having alternating linkages or chimeric oligonucleotides having alternating linkages.

It is preferred that these oligonucleotides be complementary to the translation initiation codon of the gene, and preferably that the oligonucleotides comprise a sequence CAT. In accordance with another preferred embodiment, oligonucleotides that are complementary to codon 12 of the activated H-ras gene are provided, preferably comprising a sequence GAC. In another such embodiment, oligonucleotides are provided that are complementary to and hybridize preferentially with the mutated codon 12 of the activated H-ras gene. In this embodiment, such oligonucleotide preferably comprises a sequence GAC.

Oligonucleotides of the invention are conveniently and desirably presented in a pharmaceutically acceptable carrier.

One preferred group of oligonucleotides of the inventions have at least one methylene(methylimino) linkage.

A further preferred group oligonucleotides of the invention have at least one methylene(methylimino) linkage alternating with a phosphorothioate or phosphodiester linkage. An even further group of oligonucleotides of the invention are chimeric oligonucleotides having from 8 to 30 nucleotide units specifically hybridizable with selected DNA or mRNA and containing a first region having at least one methylene(methylimino) linkage and a second region having at least one phosphorothioate linkage. In a more preferred group of these chimeric oligonucleotides the second region is flanked by two of the first regions each of which includes at least one methylene(methylimino) linkage.

In a further preferred groups of chimeric oligonucleotide of the invention the first region includes at least one nucleosidic unit modified at the 2' position. Preferred for the 2 modifications are 2'-O-alkyl, 2'-O-substituted alkyl or 2'-fluoro modifications. Most preferred is 2'-O-methoxyethyl modifications. In the chimeric oligonucleotides of the invention, preferred oligonucleotides include the second region comprising 2'-deoxynucleotides. A first preferred length for this second region is at least four nucleotides long. A more preferred length for this second region is from five to nine nucleotides long.

In certain preferred chimeric oligonucleotides of the invention the first region includes at least one methylene (methylimino) linkage alternating with a phosphorothioate or phosphodiester linkage. In further preferred oligonucleotides of the invention the first region includes one, two or three methylene(methylimino) linkages alternating with phosphorothioate or phosphodiester linkages.

In accordance with other preferred embodiments, oligonucleotides complementary to ras mRNA are provided which inhibit ras expression and which, at once, have increased resistance to nucleases, have increased binding affinity for the ras mRNA target, and are substrates for RNAse H.

It is presently preferred that increased binding affinity is conveyed by modification of at least one nucleotide at the 2' position of the sugar, most preferably comprising a 2'-O-alkyl, 2'-O-alkylamino, 2'-O-alkyl-O-alkyl or 2'-fluoro modification.

In some preferred embodiments, the oligonucleotides of the invention are chimeric oligonucleotides comprising at least one region which is modified to increase binding affinity for the complementary ras mRNA, and a region which is a substrate for RNAse H cleavage. In one such embodiment an RNAse H substrate region is flanked by two regions having increased ras mRNA binding affinity.

Other aspects of the invention are directed to methods for modulating the expression of the human ras gene in cells or tissues and for specifically modulating the expression of the activated ras gene in cells or tissues suspected of harboring a mutation leading to such activation.

Some embodiments of the invention are directed to methods for inhibiting the expression of the ras gene and for specifically inhibiting the expression of the activated ras gene.

Additional aspects of the invention are directed to methods of detection of the ras gene in cells or tissues and specific detection of the activated ras gene in cells or tissues suspected of harboring said mutated gene. Such methods comprise contacting cells or tissues suspected of containing the human ras gene with oligonucleotides in accordance with the invention in order to detect said gene.

Other aspects of the invention are directed to methods for diagnostics and therapeutics of animals suspected of having a mutation leading to activation of the ras gene. Such methods comprise contacting the animal or cells or tissues or a bodily fluid from the animal with oligonucleotides in accordance with the invention in order to inhibit the expression of this gene, to treat conditions arising from activation of this gene, or to effect a diagnosis thereof.

BRIEF DESCRIPTION OF THE DRAWINGS

FIG. 5 shows the ras mRNA target sequence (shown 5' to 3') and locations and sequences of antisense oligonucleotides targeted to the H-ras translation initiation codon (AUG) and the codon 12 region. Antisense oligonucleotides are shown 3' to 5'.

FIG. 9 is a two-part figure showing antisense oligonucleotide binding to the 47-mer H-ras RNA hairpin target.

Deoxy number=1; □: Deoxy number=0. (Inset: structure of 47-mer H-ras hairpin target shown with sequence of oligonucleotide 2570).

Figure 10:
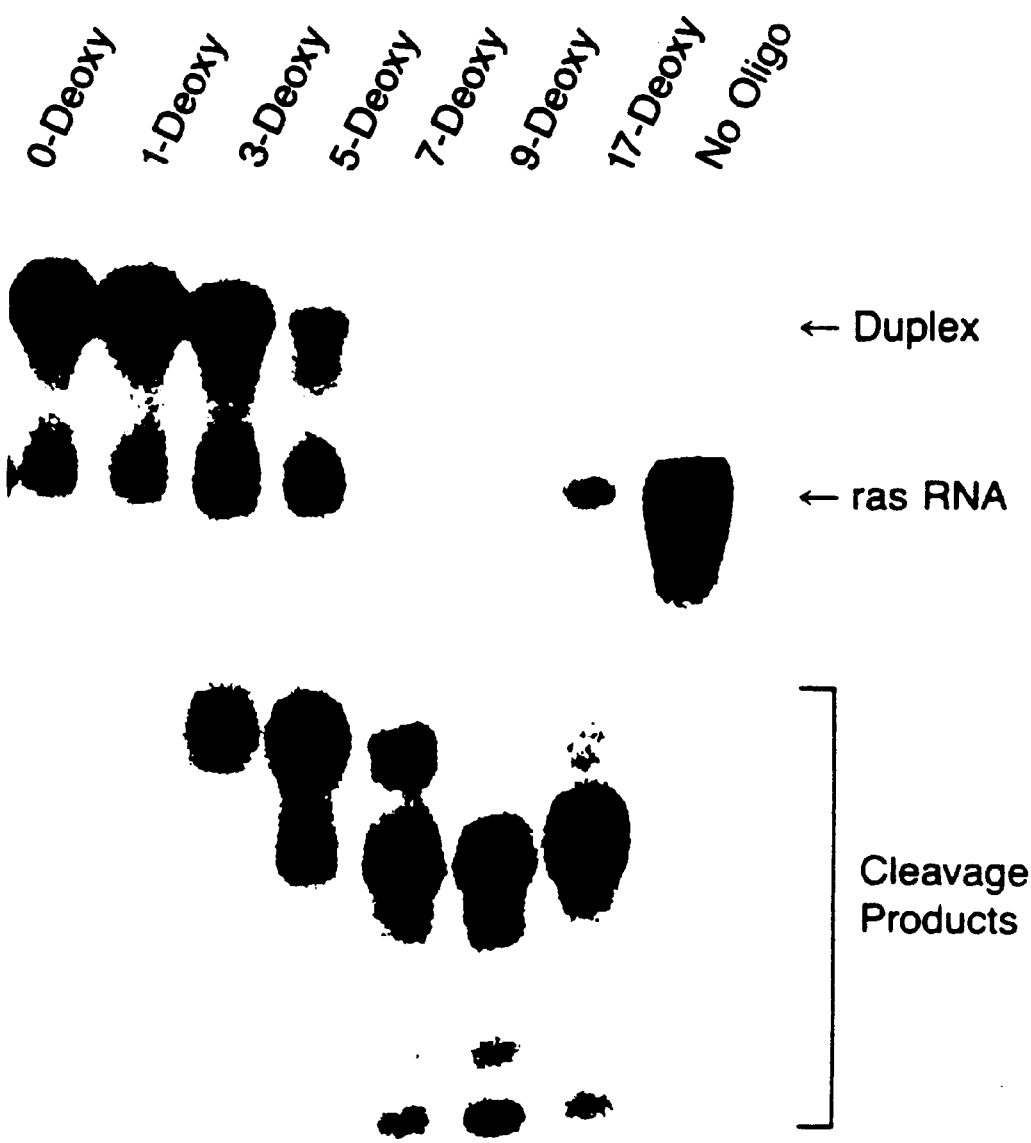

FIG. 10 is a gel showing RNAse H dependent cleavage of complementary H-ras RNA by 2'-O-methyl chimeric phosphorothioate oligonucleotides. Lane designations refer to the length of the centered deoxy gap.

FIG. 11 is a two-part figure showing antisense activity of phosphorothioate 2'-O-methyl chimeric oligonucleotides targeted to ras codon-12 RNA sequences.

Figure 11A:
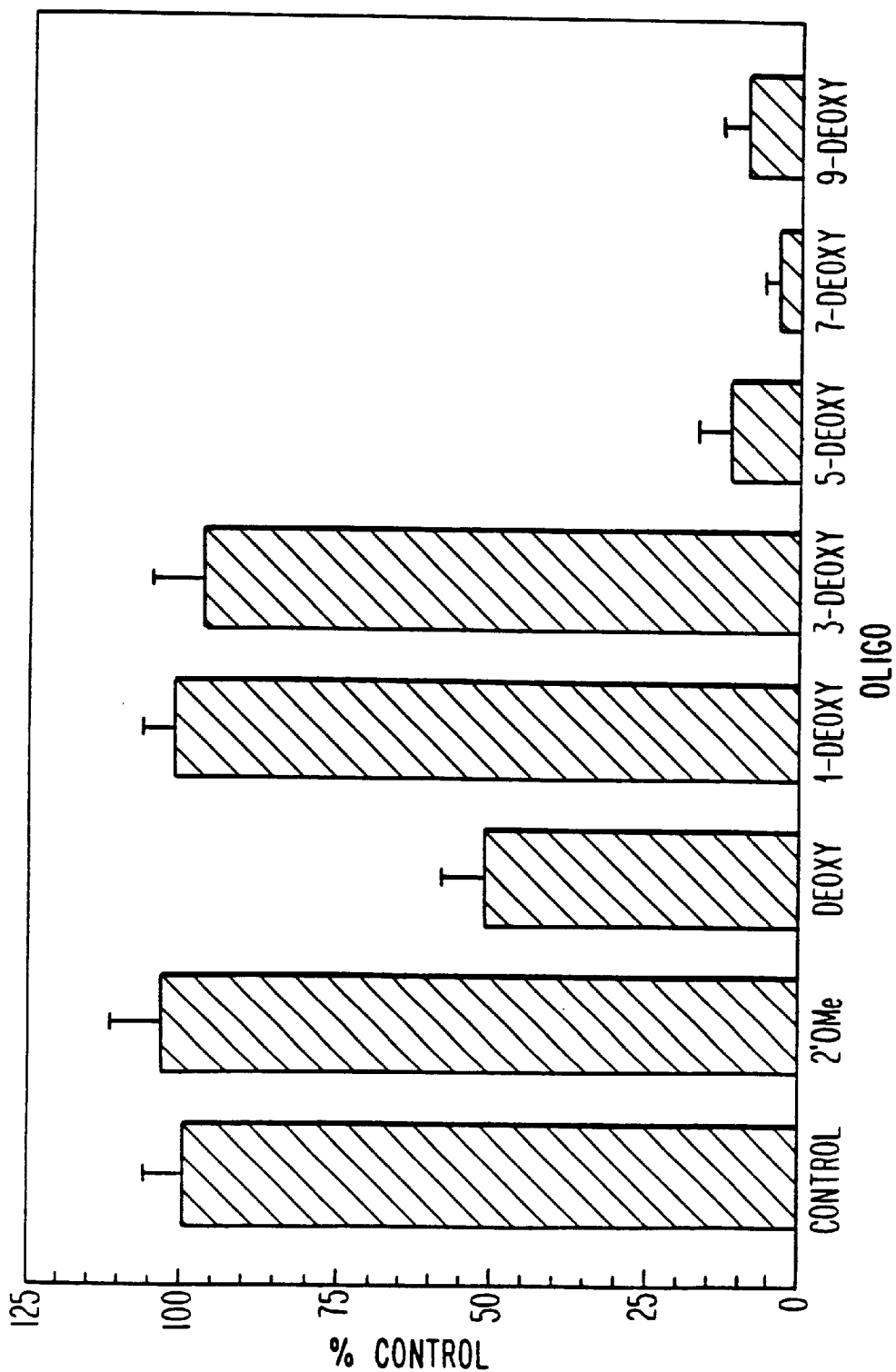

FIG. 11A is a bar graph showing single-dose activity (100 nM) of uniform 2'-O-methyl oligonucleotides, uniform deoxy oligonucleotides and chimeric 2'-O-methyl oligonucleotides containing centered 1-, 3-, 5-, 7- or 9-base deoxy gaps.

Figure 11B:
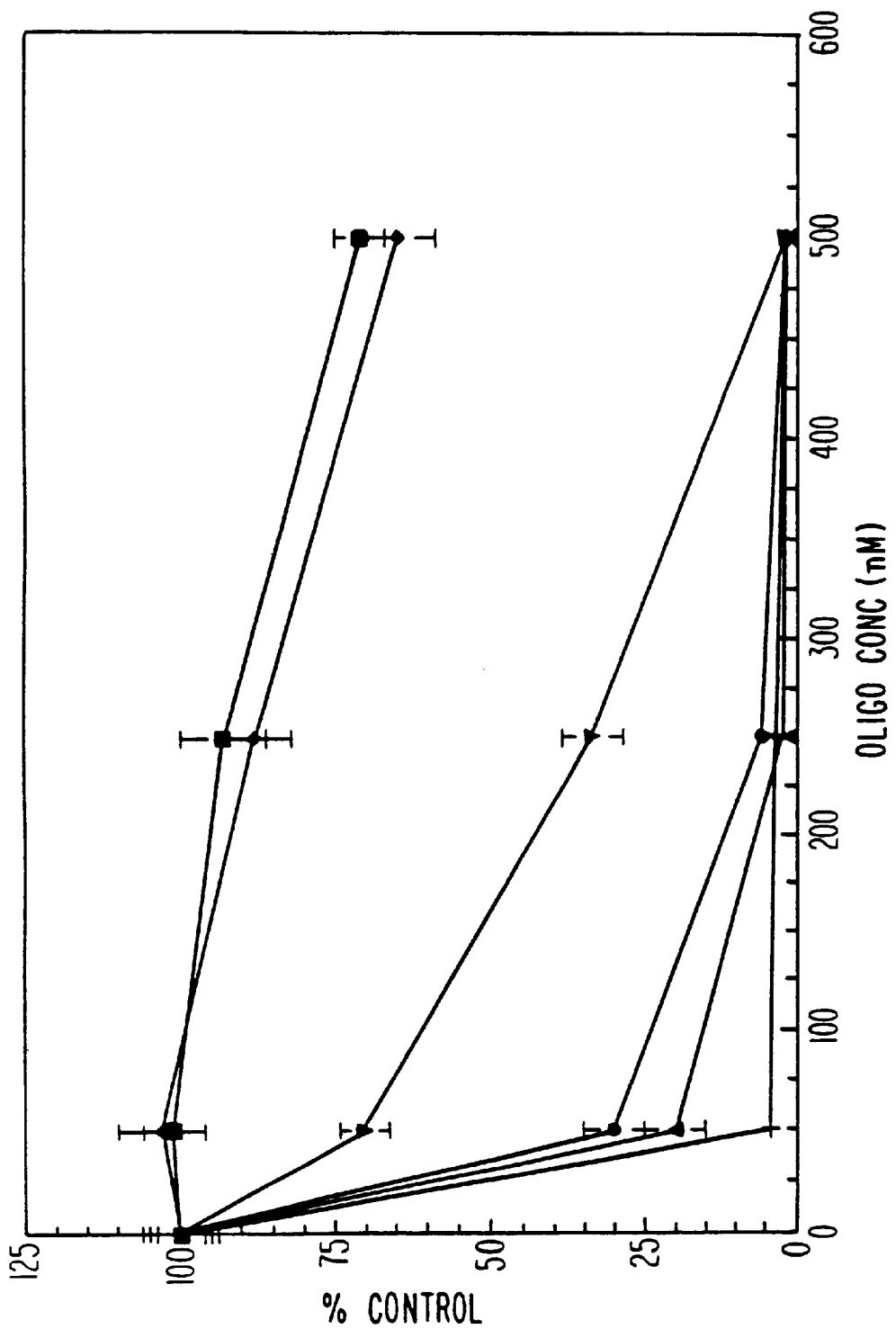

FIG. 11B is a line graph showing dose-response activity of uniform deoxy (▼) or 2'-O-methyl oligonucleotides containing centered 4-(■,♦), 5-(●), 7-(+) or 9-base (▲) deoxy gaps.

Figure 12:
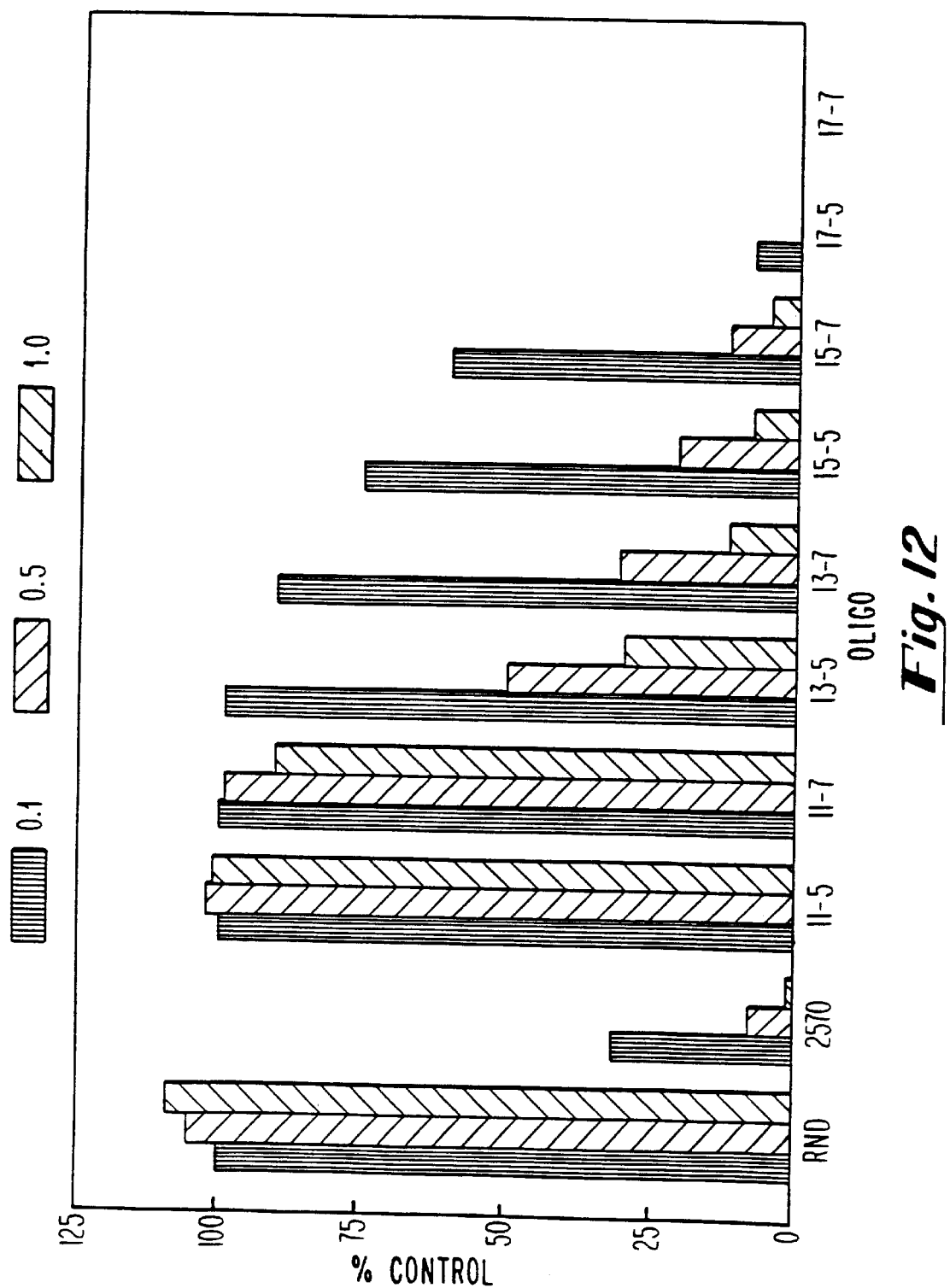

FIG. 12 is a bar graph showing antisense activities of a uniform deoxy phosphorothioate and shortened chimeric oligonucleotides against ras-luciferase.

Figure 13:
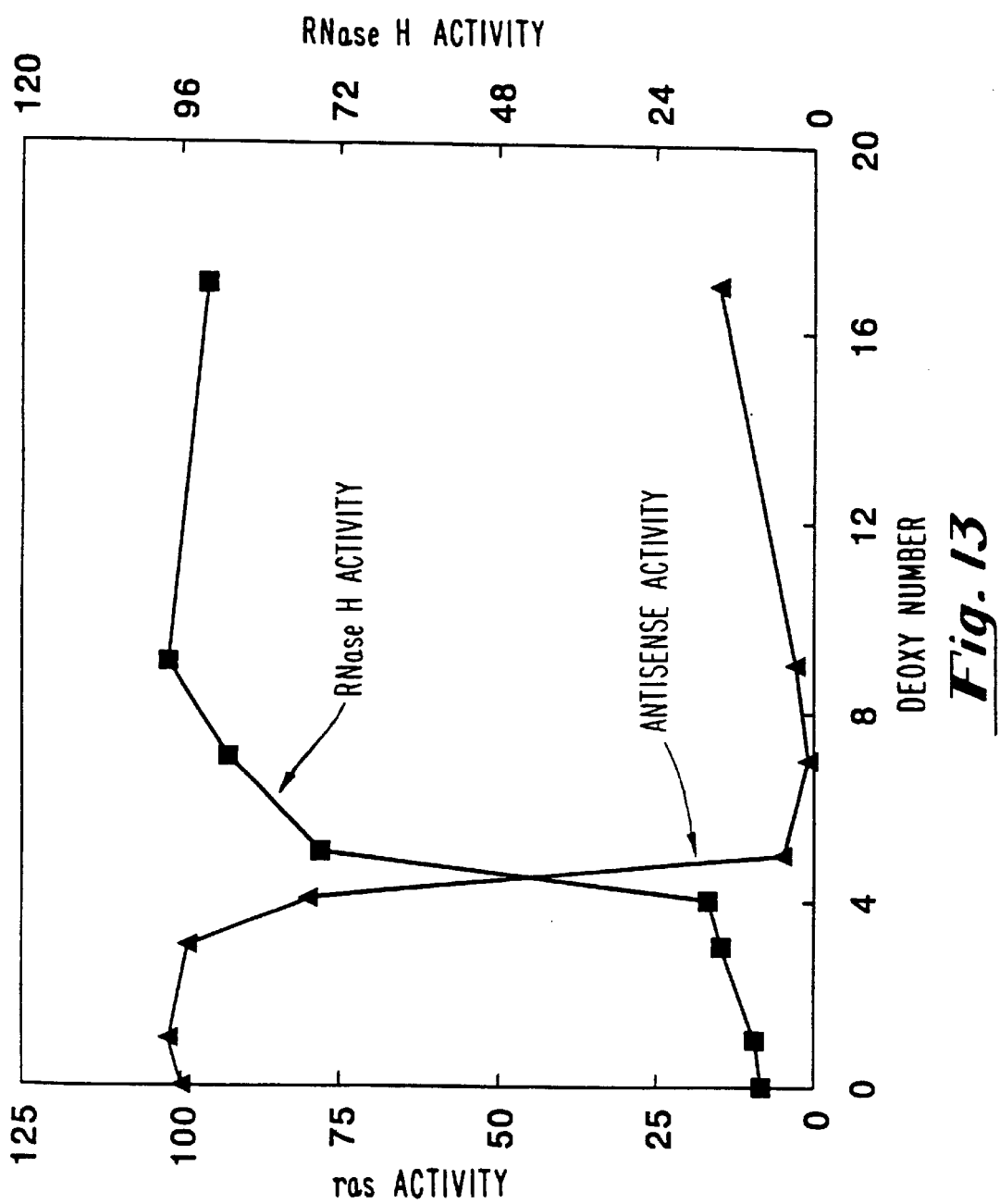

FIG. 13 is a line graph showing correlation between antisense activity and ability to activate RNAse H as a function of deoxy gap length using phosphorothioate 2'-O-methyl oligonucleotides targeted against ras.

Figure 14:
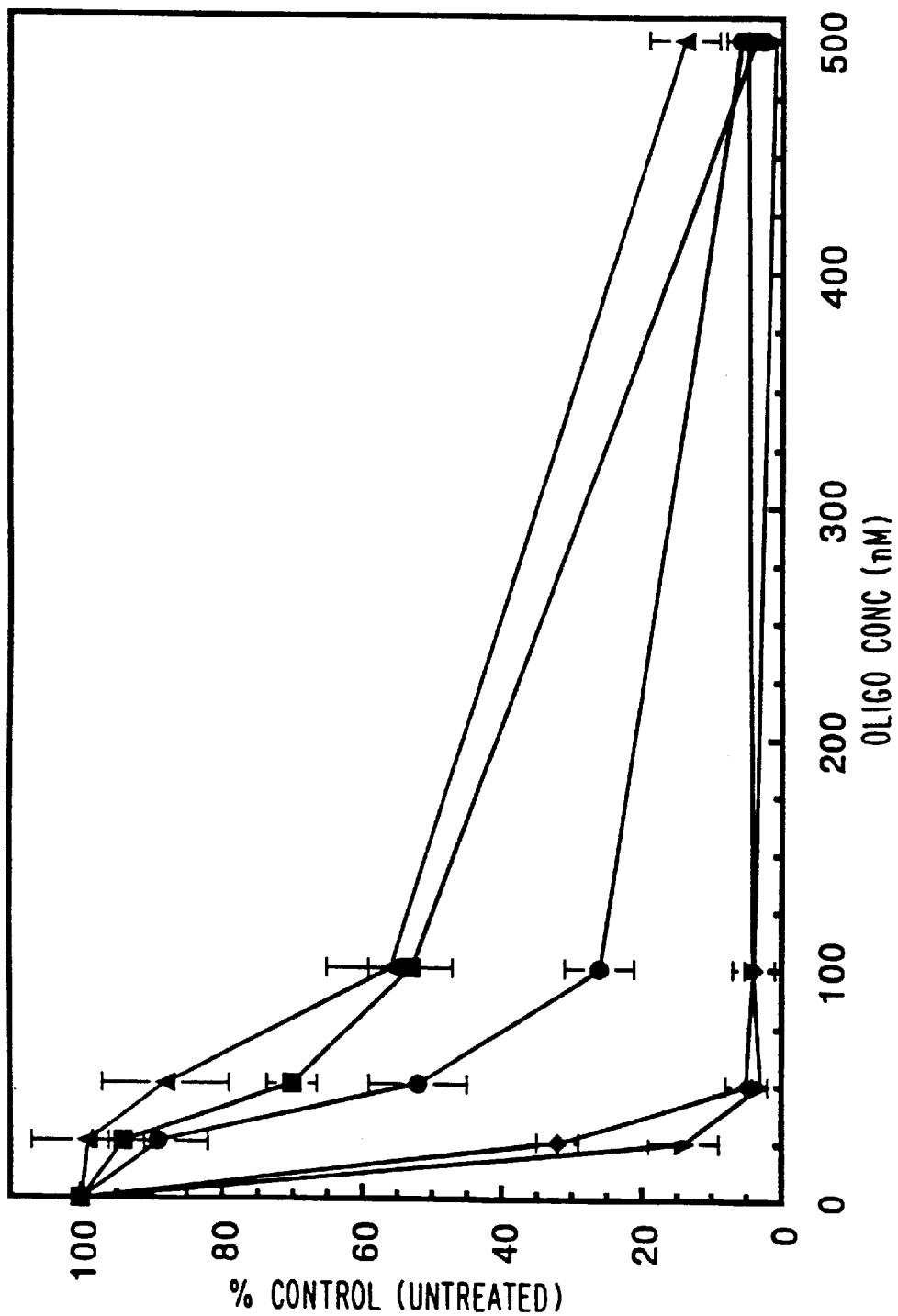

FIG. 14 is a line graph showing does response antisense activities of phosphorothioate 2'-modified chimeric oligonucleotides containing 7-base deoxy gaps. (▲), uniform deoxy phosphorothioate; (■), 2'-O-pentyl chimera; (●), 2'-O-propyl chimera; (♦) 2'-O-methyl chimera; (▼), 2'-fluoro chimera.

Figure 15:
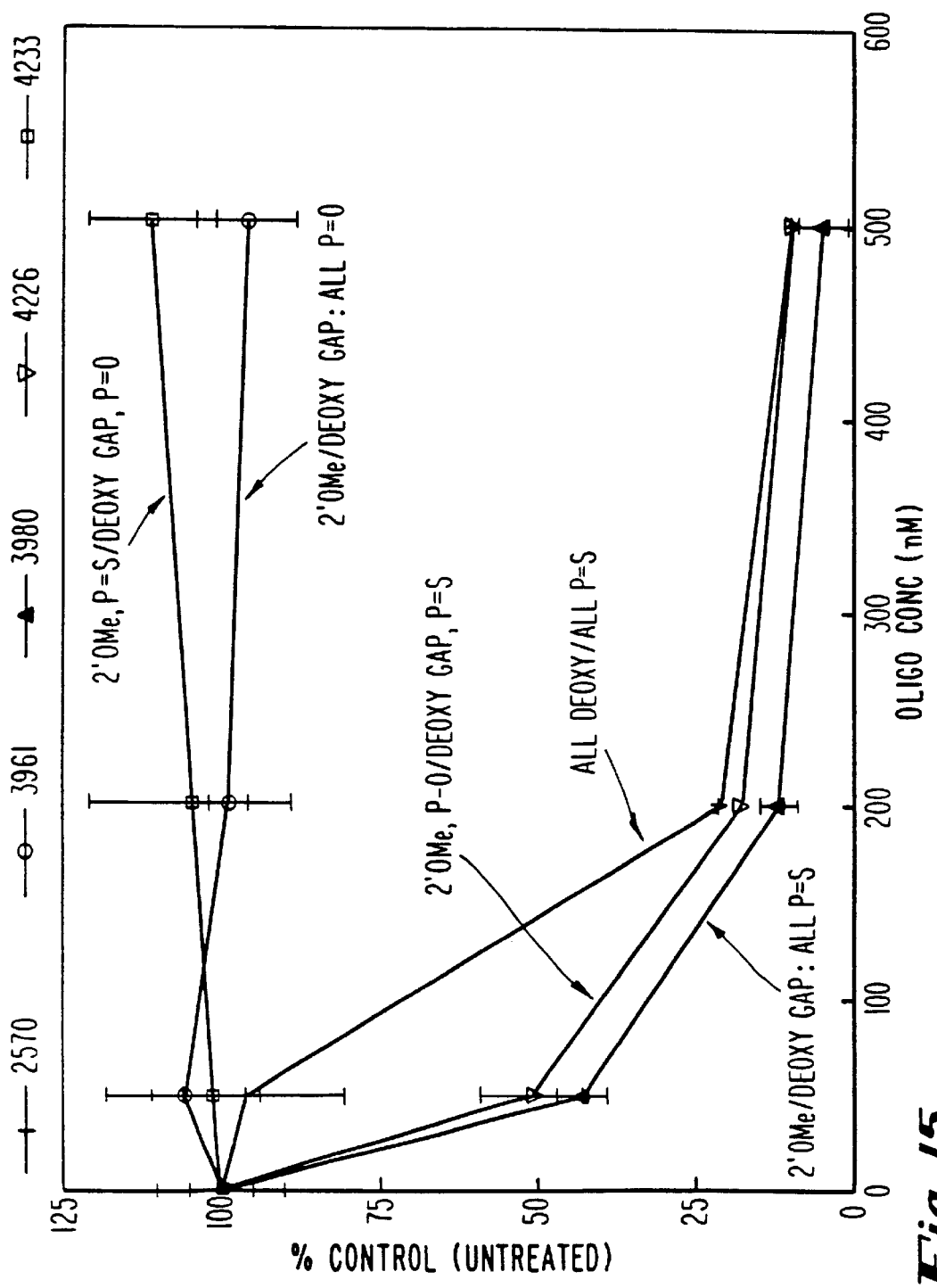

FIG. 15 is a bar graph showing dose-dependent oligonucleotide inhibition of ras-luciferase by chimeric oligonucleotides having various combinations of phosphorothioate and phosphodiester backbones and 2'-O-methyl and 2'-deoxy nucleotides.

Figure 16:
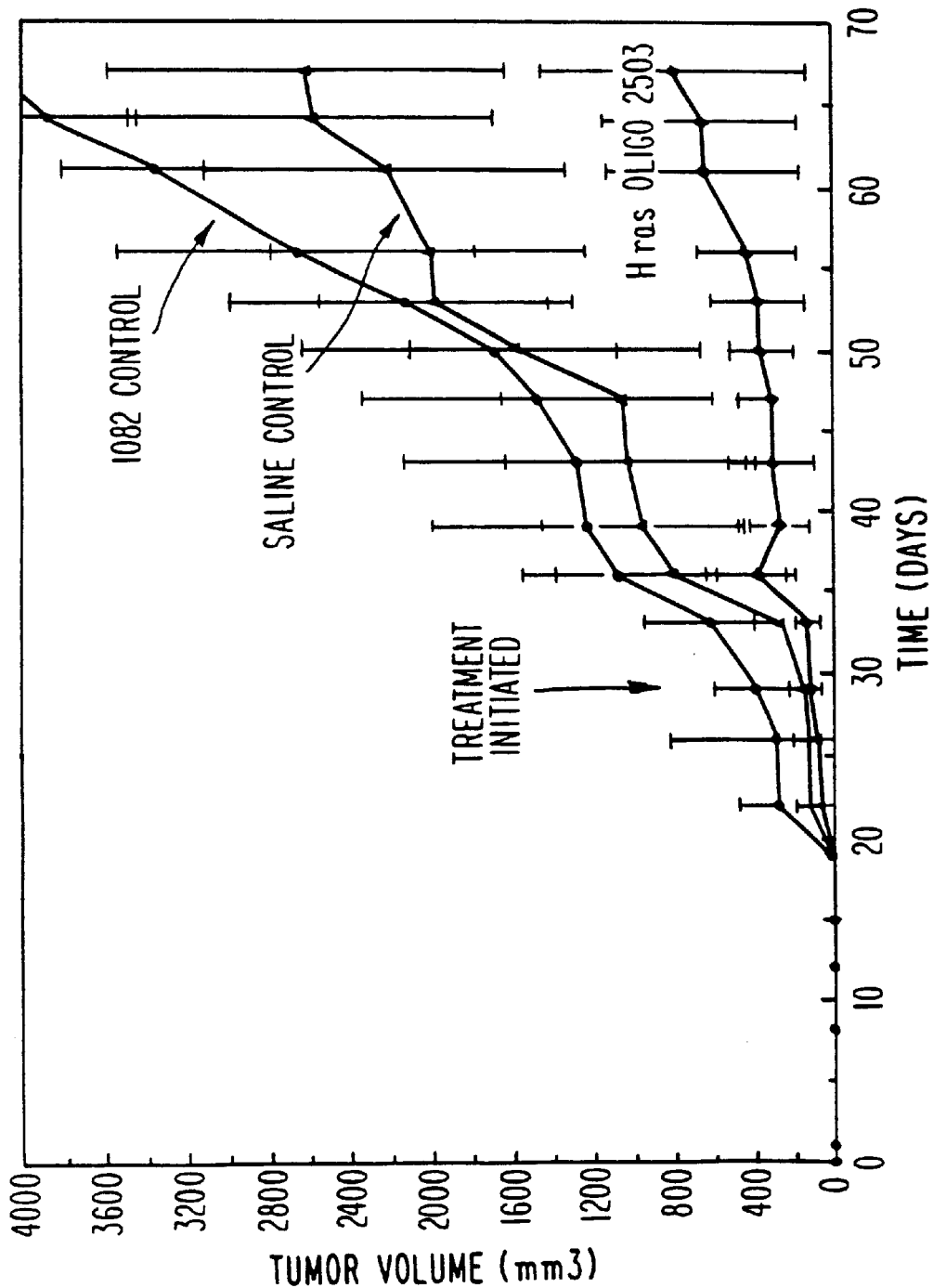

FIG. 16 is a line graph showing anti-tumor activity of ISIS 2503 against A549 human cell tumors in nude mice.

Figure 17:
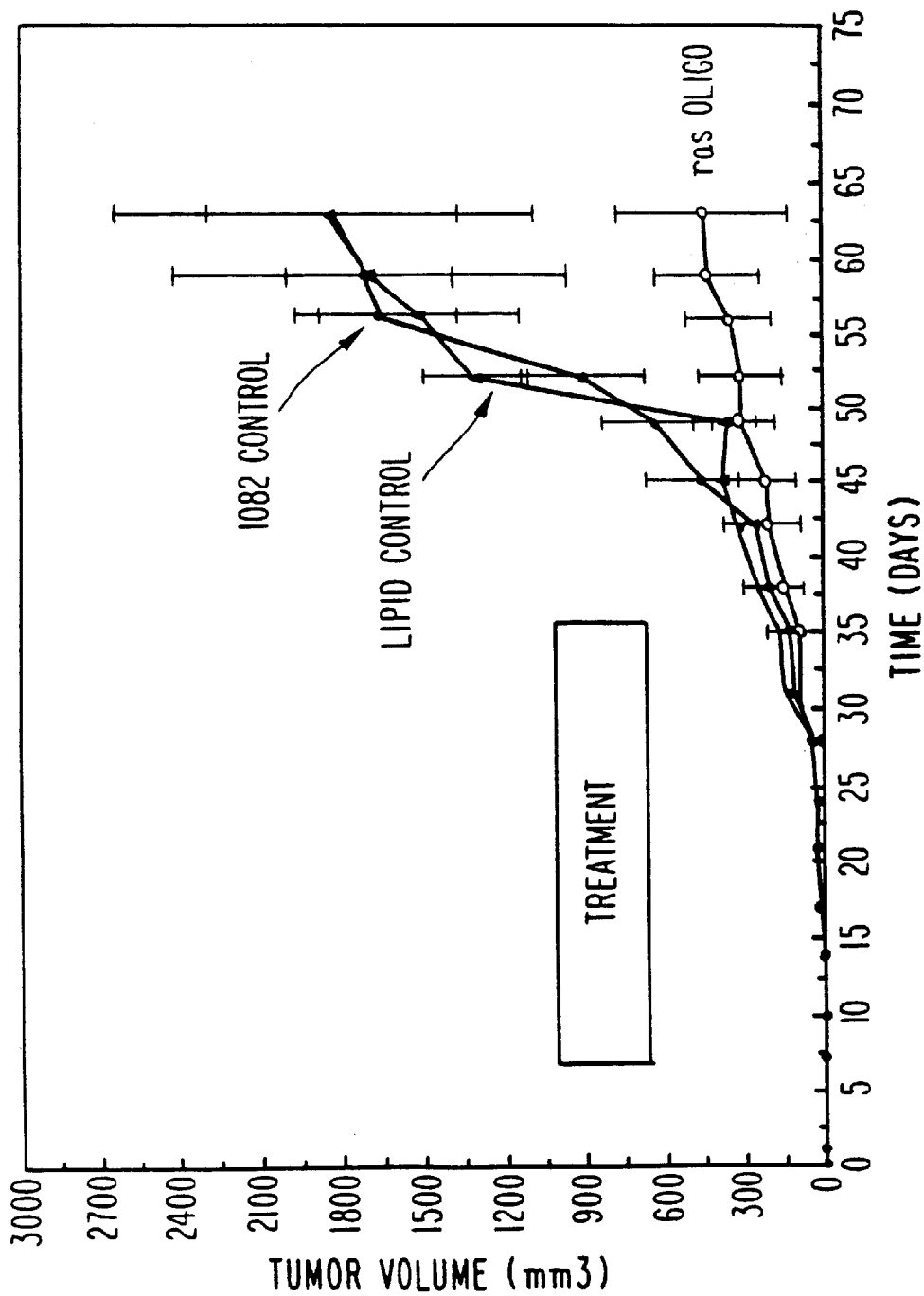

FIG. 17 is a line graph showing anti-tumor activity of ras oligo ISIS 2503, administered with cationic lipid, against A549 human cell tumors in nude mice.

Figure 18:
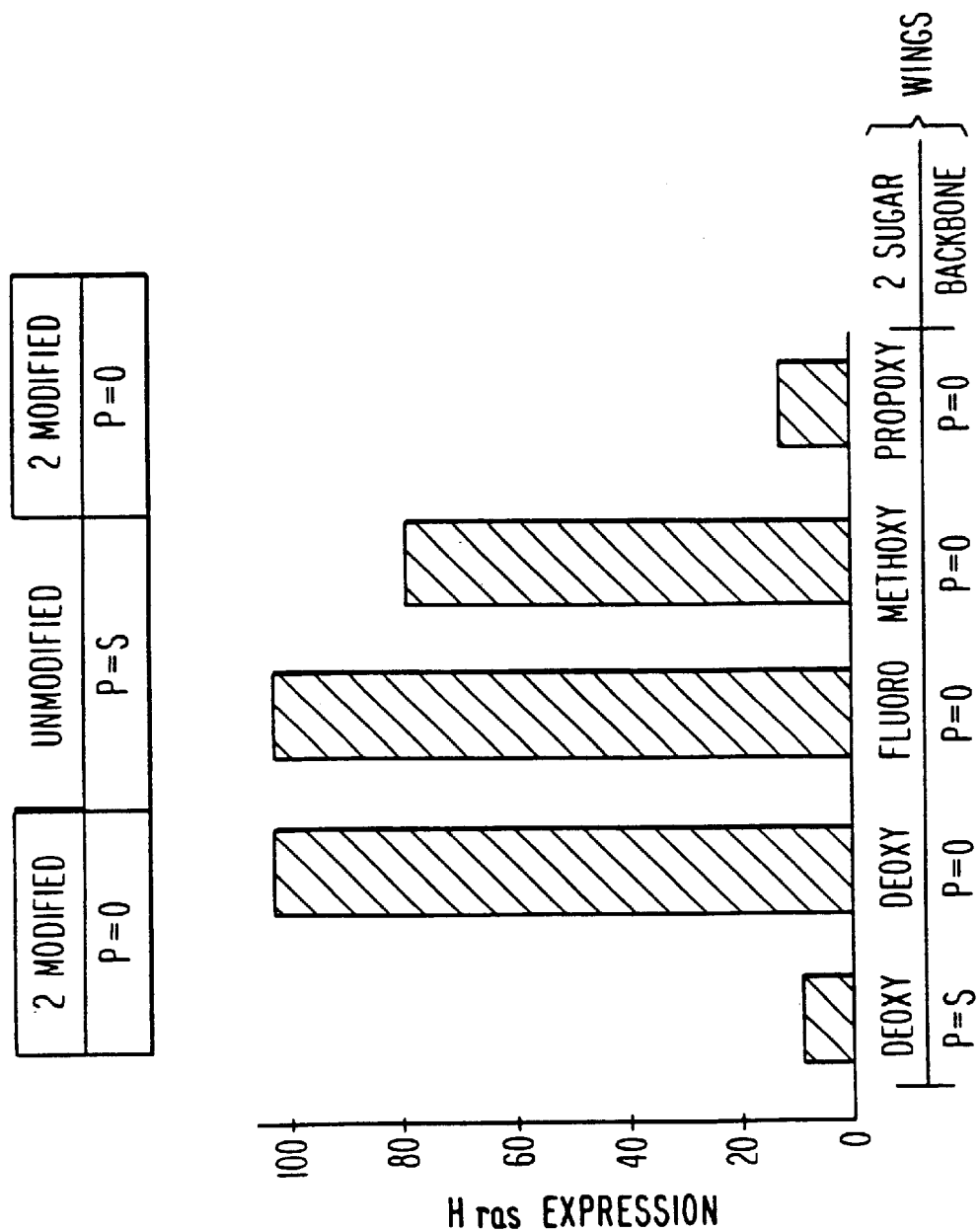

FIG. 18 is a bar graph showing activity against Ha-ras of oligonucleotides with various 2' sugar modifications and phosphodiester (P=O) backbones compared to a 2'deoxyoligonucleotide with phosphorothioate (P=S) backbone.

Figure 19:
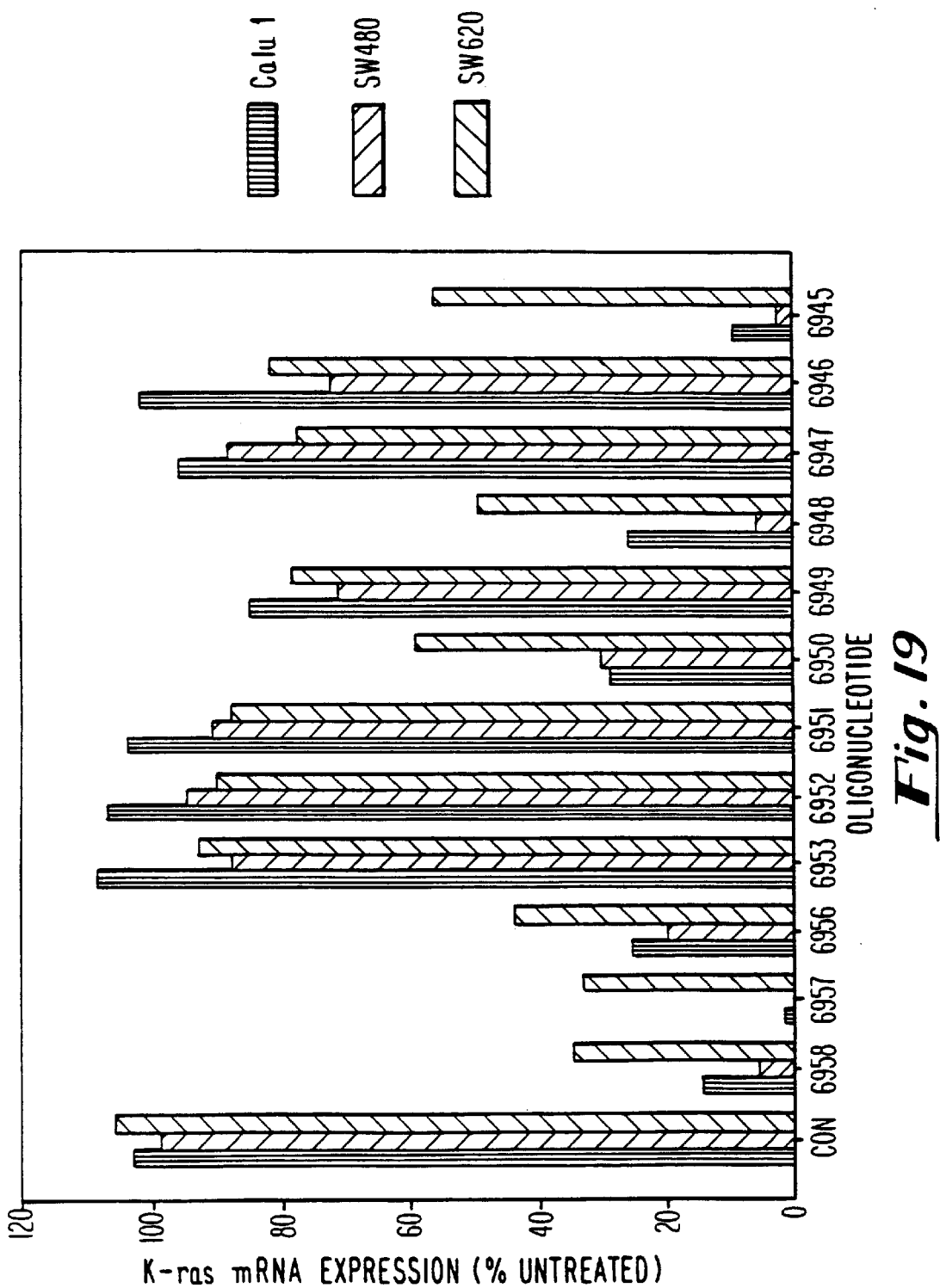

FIG. 19 is a bar graph showing antisense inhibition of Ki-ras mRNA expression in three human colon carcinoma cell lines, Calu1, SW480 and SW620.

Figure 20:
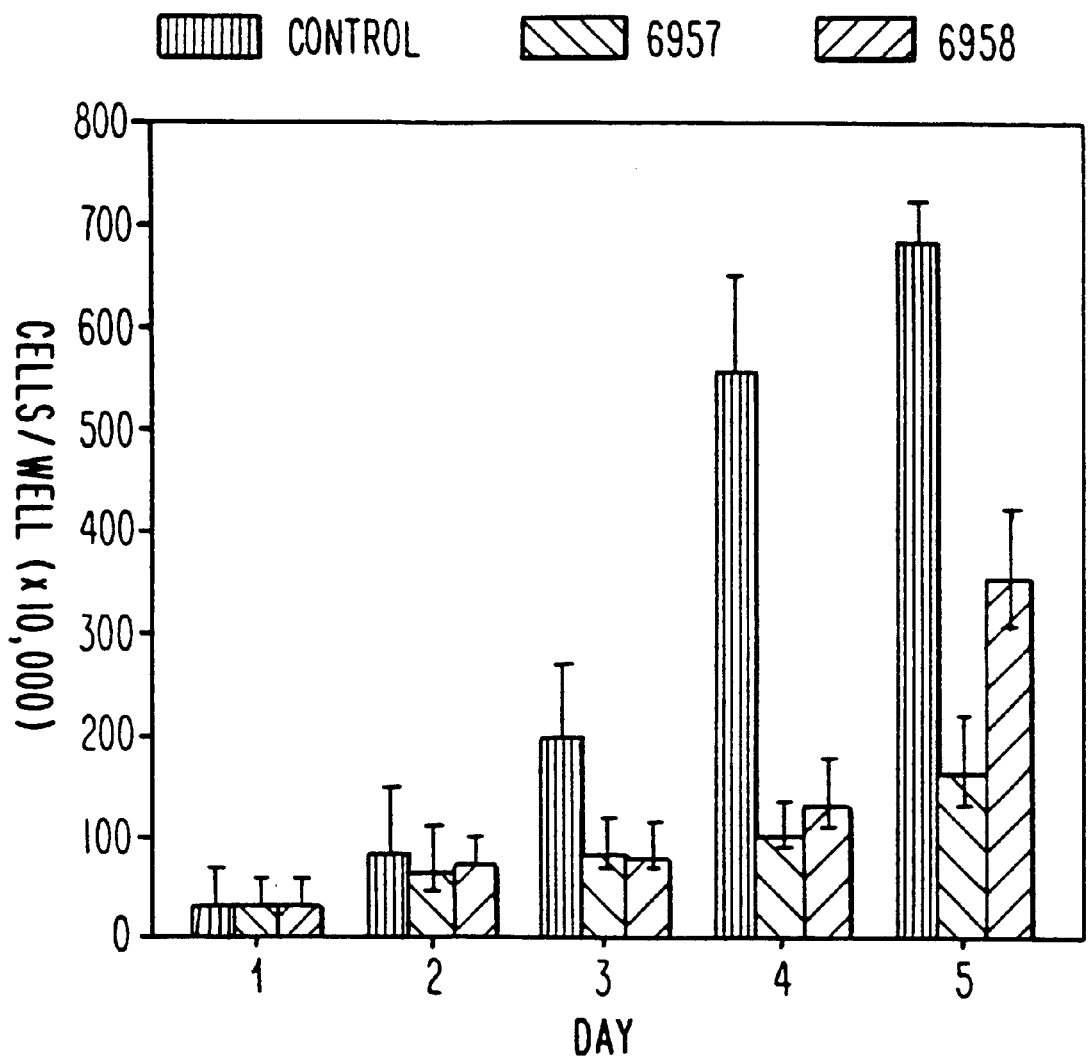

FIG. 20 is a bar graph showing inhibition of SW480 human carcinoma cell line proliferation by Ki-ras specific oligonucleotides ISIS 6957 and ISIS 6958.

Figure 21:
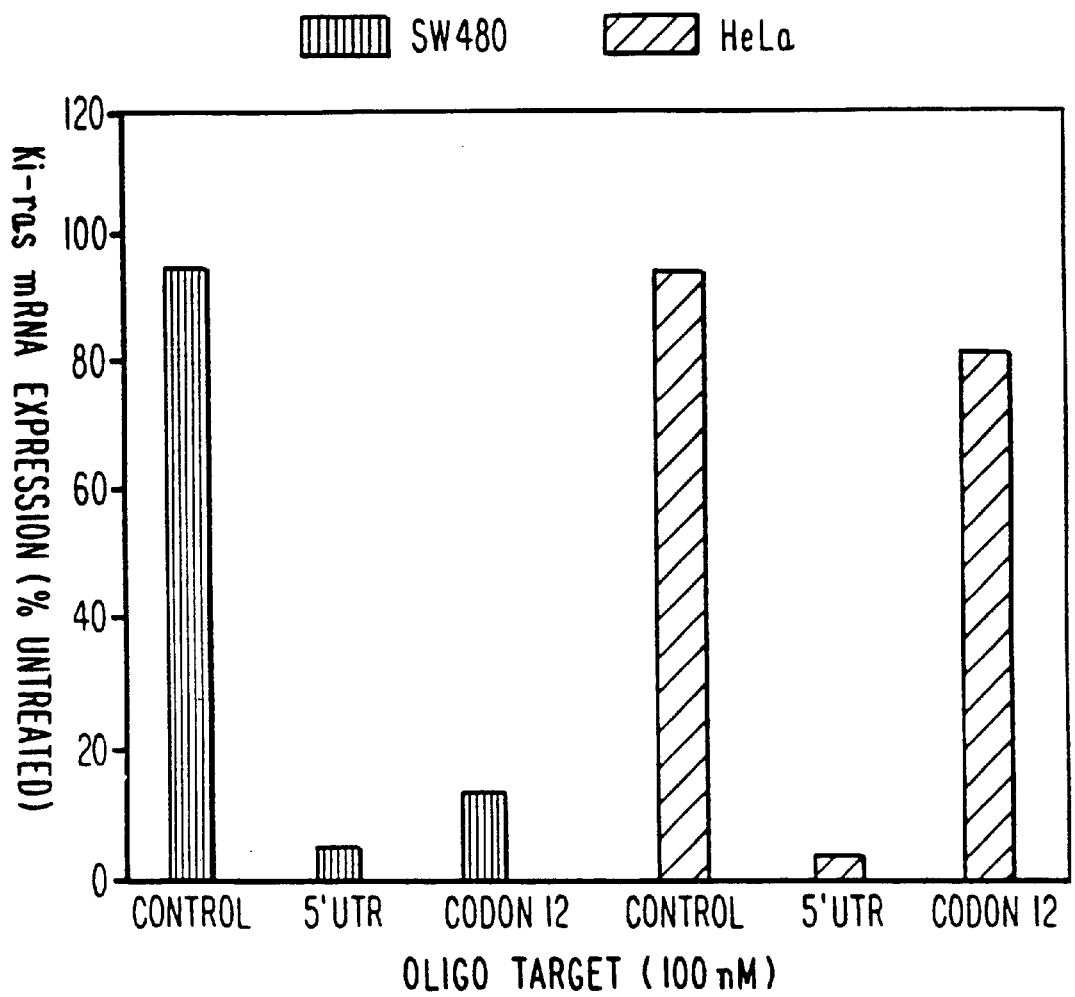

FIG. 21 is a bar graph showing selective inhibition of Ki-ras mRNA expression in human carcinoma SW480 cells, which express mutant Ki-ras, compared to HeLa cells, which express wild-type Ki-ras, when treated with oligonucleotide targeted to the mutant Ki-ras codon-12.

Figure 22:
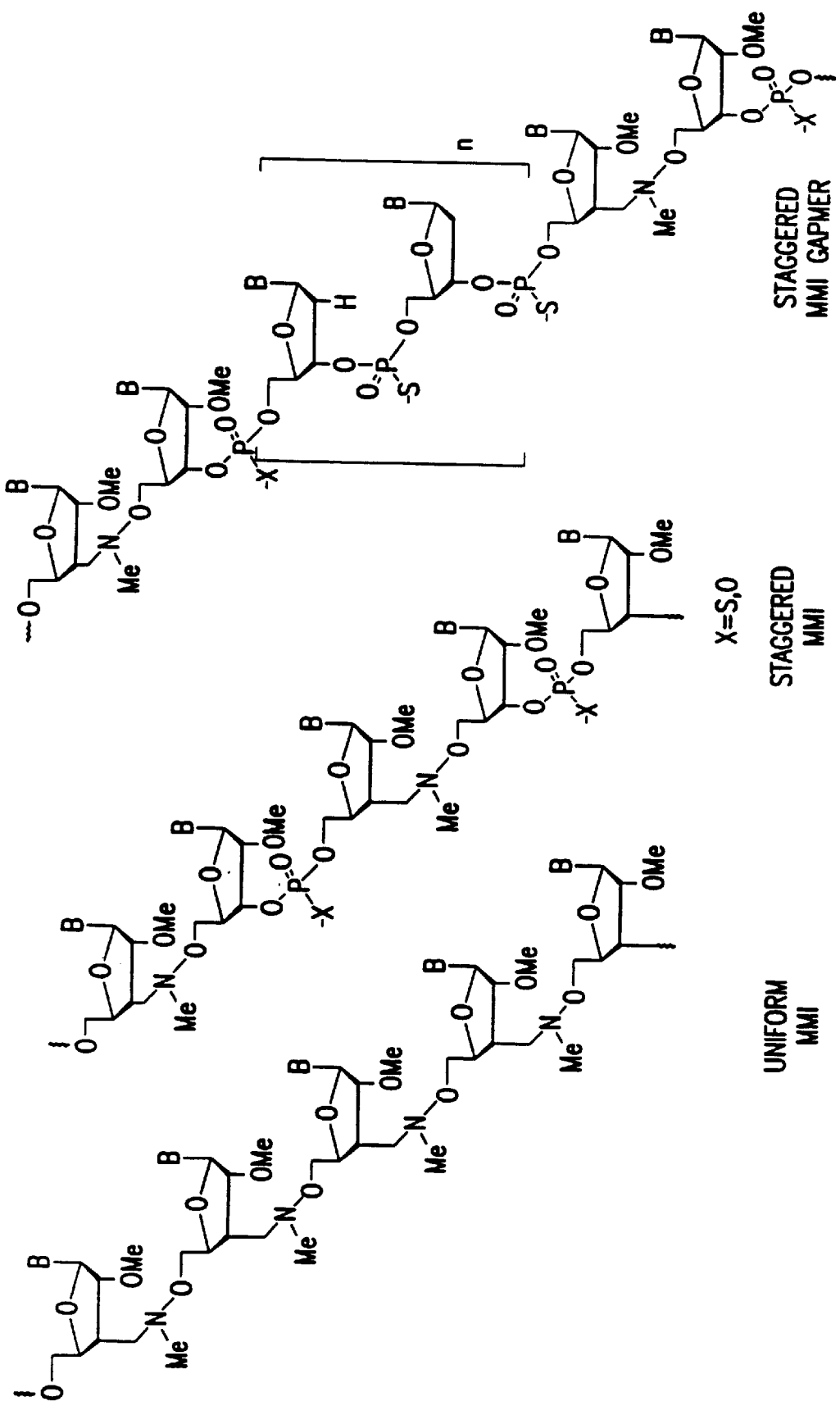

FIG. 22 illustrates preferred chemical structures of certain oligonucleotides of the invention.

Figures 23A, 23B:
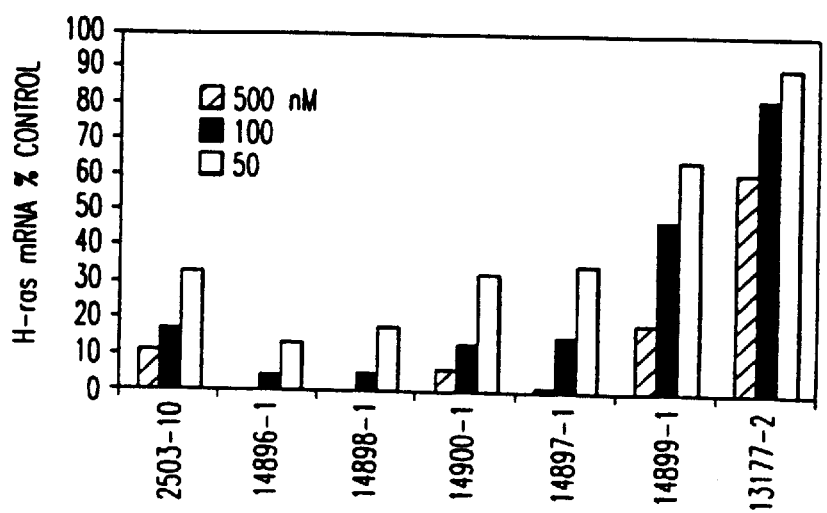
Figures 24A, 24B:
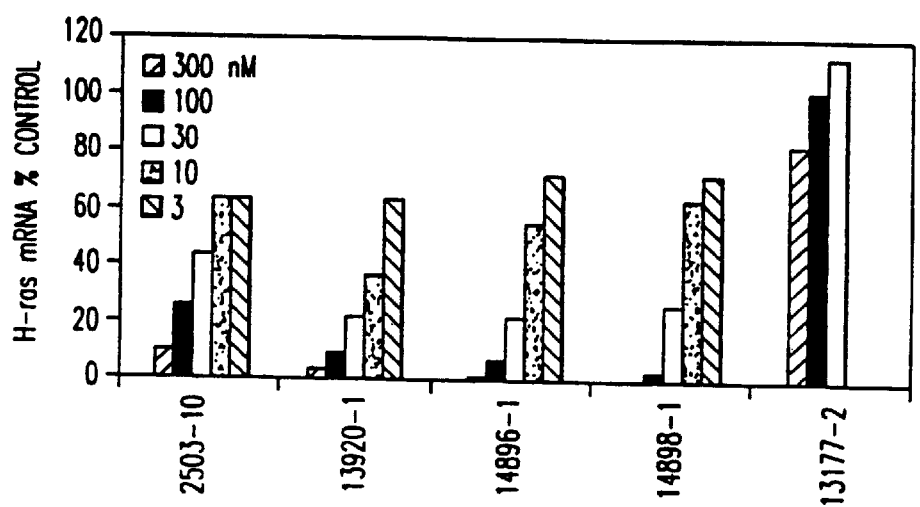

FIGS. 23 and 24 each show a table and a bar graph summarizing properties and inhibition responses for certain preferred antisense oligonucleotides specifically hybridizable with the activated H-ras gene or scrambled controls. The tables show the nucleobase composition and chemistry at each position along the length of the oligonucleotides. The bar graphs summarize the dose response inhibition of H-ras mRNA in T-24 cells for each of the tested doses of the oligonucleotides.

DETAILED DESCRIPTION OF THE INVENTION

Malignant tumors develop through a series of stepwise, progressive changes that lead to the loss of growth control characteristic of cancer cells, i.e., continuous unregulated proliferation, the ability to invade surrounding tissues, and the ability to metastasize to different organ sites. Carefully controlled in vitro studies have helped define the factors that characterize the growth of normal and neoplastic cells and have led to the identification of specific proteins that control cell growth and differentiation. In addition, the ability to study cell transformation in carefully controlled, quantitative in vitro assays has led to the identification of specific genes capable of inducing the transformed cell phenotype. Such cancer-causing genes, or oncogenes, are believed to acquire transformation-inducing properties through mutations leading to changes in the regulation of expression of their protein products. In some cases such changes occur in non-coding DNA regulatory domains, such as promoters and enhancers, leading to alterations in the transcriptional activity of oncogenes, resulting in over- or under-expression of their gene products. In other cases, gene mutations occur within the coding regions of oncogenes, leading to the production of altered gene products that are inactive, overactive, or exhibit an activity that is different from the normal (wild-type) gene product.

To date, more than 30 cellular oncogene families have been identified. These genes can be categorized on the basis of both their subcellular location and the putative mechanism of action of their protein products. The ras oncogenes are members of a gene family which encode related proteins that are localized to the inner face of the plasma membrane. ras proteins have been shown to be highly conserved at the amino acid level, to bind GTP with high affinity and specificity, and to possess GTPase activity. Although the cellular function of ras gene products is unknown, their biochemical properties, along with their significant sequence homology with a class of signal-transducing proteins known as GTP binding proteins, or G proteins, suggest that ras gene products play a fundamental role in basic cellular regulatory functions relating to the transduction of extracellular signals across plasma membranes.

Three ras genes, designated H-ras, K-ras, and N-ras, have been identified in the mammalian genome. Mammalian ras genes acquire transformation-inducing properties by single point mutations within their coding sequences. Mutations in naturally occurring ras oncogenes have been localized to codons 12, 13, and 61. The sequences of H-ras, K-ras and N-ras are known. Capon et al., *Nature* 302 1983, 33–37; Kahn et al., *Anticancer Res.* 1987, 7, 639–652; Hall and Brown, *Nucleic Acids Res.* 1985, 13, 5255–5268. The most commonly detected activating ras mutation found in human tumors is in codon 12 of the H-ras gene in which a base change from GGC to GTC results in a glycine-to-valine substitution in the GTPase regulatory domain of the ras protein product. Tabin, C. J. et al., *Nature* 1982, 300, 143–149; Reddy, P. E. et al., *Nature* 1982, 300, 149–152; Taparowsky, E. et al., *Nature* 1982, 300, 762–765. This single amino acid change is thought to abolish normal control of ras protein function, thereby converting a normally regulated cell protein to one that is continuously active. It is believed that such deregulation of normal ras protein function is responsible for the transformation from normal to malignant growth.

The present invention provides oligonucleotides for inhibition of human ras gene expression. Such oligonucleotides specifically hybridize with selected DNA or mRNA deriving from a human ras gene. The invention also provides oligonucleotides for selective inhibition of expression of the mutant form of ras.

In the context of this invention, the term "oligonucleotide" refers to an oligomer or polymer of ribonucleic acid or deoxyribonucleic acid. This term includes oligomers consisting of naturally occurring bases, sugars and intersugar (backbone) linkages as well as oligomers having non-naturally occurring portions which function similarly. Such modified or substituted oligonucleotides are often preferred over native forms because of properties such as, for example, enhanced cellular uptake and increased stability in the presence of nucleases.

Specific examples of preferred oligonucleotides of the invention contain phosphodiester, phosphorothioates or heteroatom intersugar linkages or chimeric and/or alternating mixtures of these linkages. Preferred heteroatom intersugar linkage are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P(=O)—O—$CH_2$). Most preferred is the $CH_2$—N($CH_3$)—O1'$CH_2$ linkage. The $CH_2$—N($CH_3$)—O—$CH_2$ linkage can be named in various ways including as 3'-de(oxyphosphinico)-3'-[methylene(methylimino)] linkage that can be shorten to a methylene(methylimino) linkage or shorten still to the acronym "MMI" linkage. In certain chimeric mixed backbones of the invention regions of phosphorothioate nucleotides are flanked by regions of heteroatom linkages or by regions of alternating heteroatom and one of phosphodiester or phosphorothioate linkages.

Other preferred oligonucleotides may contain alkyl and halogen-substituted sugar moieties. Preferred substituted sugar moieties comprise one of the following at the 2' position: F, $O(CH_2)_nNH_2$, $O(CH_2)_nCH_3$ or $O(CH_2)_n$—O—$(CH_2)_nCH_3$ where n is from 0 to about 10.

The oligonucleotides of the invention include the standard nucleosidic bases including but not limited to purin-9-yl and pyrimid-1-yl heterocycles including adenine, guanine, thymine, uracil and cytosine. Other preferred embodiments may include at least one modified base form. Some specific examples of such modified bases include 2-(amino)adenine, 2-(methylamino)adenine, 2-(imidazolylalkyl)adenine, 2-(aminoalklyamino)adenine, 7-deaza-propynyl adenine or guanine, 7-deaza-8-aza adenine or guanine, 5-methylcytosine, 5-propynyl uracil, 2-thiouracil, 2-aminouracil, and psuedouracil.

Preferred oligonucleotides of this invention may, at once, comprise nucleotides modified to increase their resistance to nucleases, comprise nucleotides modified to increase their affinity for ras mRNA, and comprise nucleotides which are substrates for RNAse H. In one preferred embodiment, a chimeric oligonucleotide comprises at least one region modified to increase ras mRNA binding affinity, and a region which is a substrate for RNAse H. The oligonucleotide is also modified to enhance nuclease resistance. In a more preferred embodiment, the region which is a substrate for RNAse H is flanked by two regions which are modified to increase ras mRNA binding affinity. The effect of such modifications is to greatly enhance antisense oligonucleotide inhibition of ras gene expression.

The oligonucleotides in accordance with this invention preferably comprise from about 8 to about 50 nucleic acid base units. It is more preferred that such oligonucleotides comprise from about 8 to 30 nucleic acid base units, and still more preferred to have from about 13 to 25 nucleic acid base units. As will be appreciated, a nucleic acid base unit is a base-sugar combination suitably bound to adjacent nucleic acid base unit through phosphodiester or other bonds.

"Hybridization," in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them.

"Specifically hybridizable" indicates a sufficient degree of complementarity to avoid non-specific binding of the oligonucleotide to non-target sequences. It is understood that an oligonucleotide need not be 100% complementary to its target nucleic acid sequence to be specifically hybridizable.

Antisense Oligonucleotide Inhibition of ras-Luciferase Gene Expression: A series of antisense phosphorothioate oligonucleotides targeted to either the H-ras translation initiation codon or the codon-12 point mutation of activated H-ras were screened using the ras-luciferase reporter gene system described in Examples 2–5. Of this initial series, six oligonucleotides were identified that gave significant and reproducible inhibition of ras-luciferase activity. The base sequences, sequence reference numbers and SEQ ID numbers of these oligonucleotides (all are phosphorothioates) are shown in Table 1.

TABLE 1

| OLIGO REF NO | SEQUENCE | SEQ ID NO: |
|---|---|---|
| 2502 | CTT-ATA-TTC-CGT-CAT-CGC-TC | 1 |
| 2503 | TCC-GTC-ATC-GCT-CCT-CAG-GG | 2 |
| 2570 | CCA-CAC-CGA-CGG-CGC-CC | 3 |
| 2571 | CCC-ACA-CCG-ACG-GCG-CCC-A | 4 |
| 2566 | GCC-CAC-ACC-GAC-GGC-GCC-CAC | 5 |
| 2560 | TGC-CCA-CAC-CGA-CGG-CGC-CCA-CC | 6 |

Figure 1:
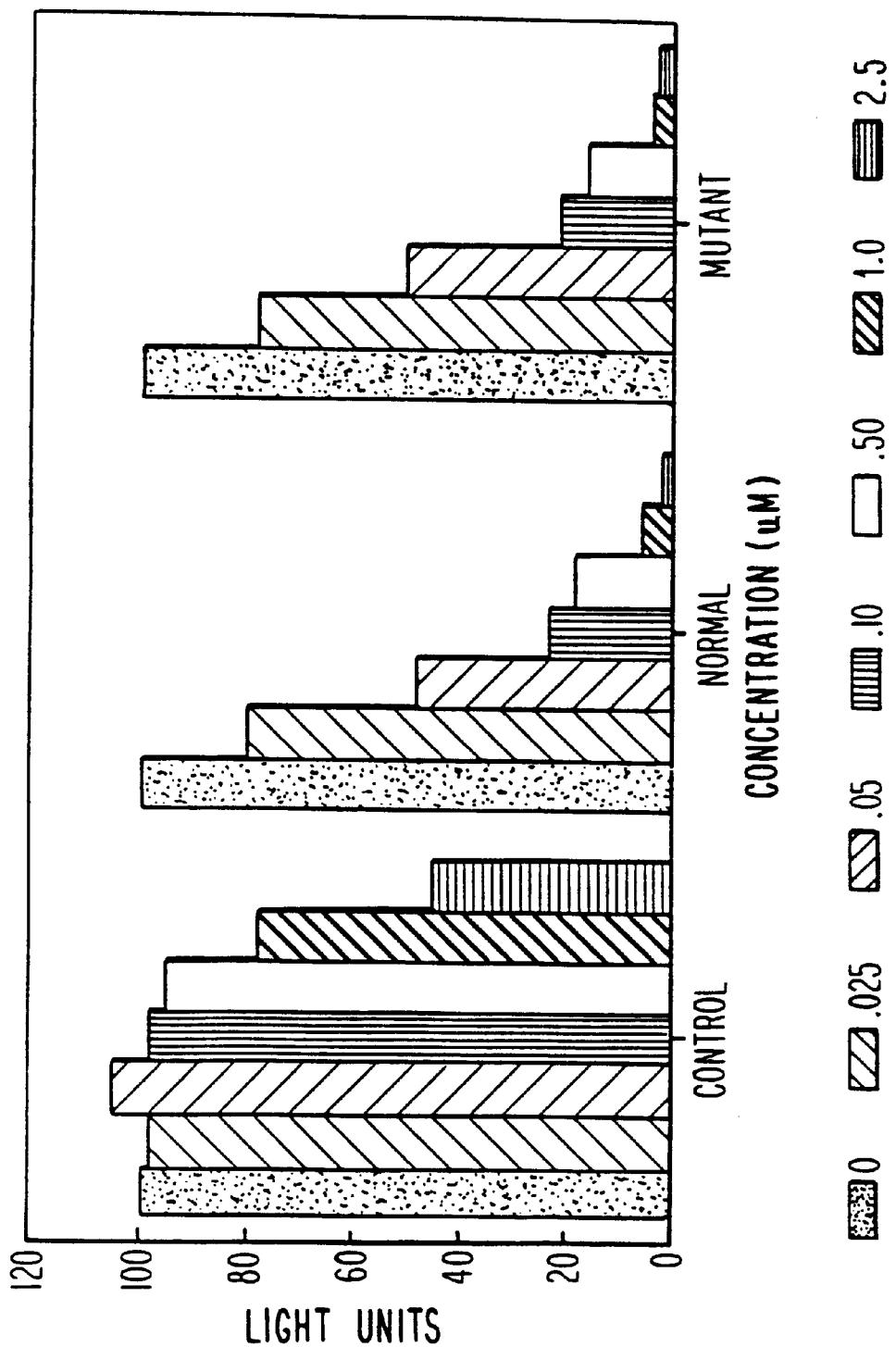
FIG. 1 is a bar graph showing dose-response inhibition of ras-luciferase fusion protein expression using oligonucleotides targeted to the H-ras translation initiation codon (AUG). Expression is measured by measurement of luciferase activity as assayed by amount of light emitted when luciferin is added.

FIG. 1 shows a dose-response experiment in which cells expressing either the normal ras-luciferase reporter gene or the mutant ras-luciferase reporter gene were treated with increasing concentrations of the phosphorothioate oligonucleotide 2503 (SEQ ID NO: 2). This compound is targeted to the translational initiation codon of H-ras RNA transcripts. As shown in FIG. 1, treatment of cells with this oligonucleotide resulted in a dose-dependent inhibition of ras-luciferase activity, displaying IC50 values of approximately 50 nM for both the normal and the mutant ras targets. The control oligonucleotide is a random phosphorothioate oligonucleotide, 20 bases long. Results are expressed as percentage of luciferase activity in transfected cells not treated with oligonucleotide. The observation that an oligonucleotide targeted to the ras translation initiation codon is equally effective in reducing both mutant and normal ras expression is expected since the two targets have identical sequence compositions in the region surrounding the AUG translation initiation site.

Figure 2:
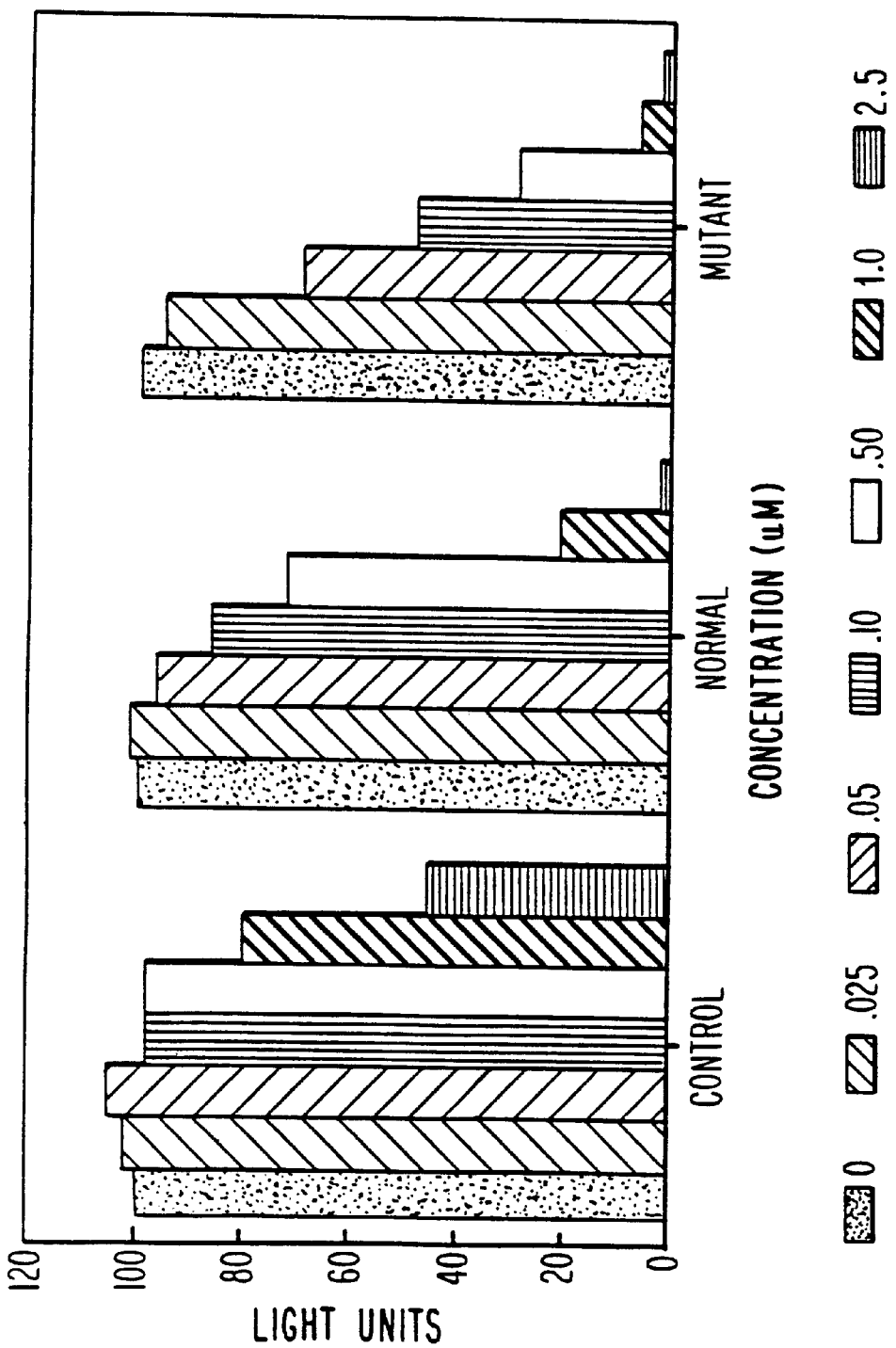
FIG. 2 is a bar graph showing dose-response inhibition of ras-luciferase fusion protein expression using oligonucleotides targeted to the mutated codon-12 region in activated H-ras. Expression is measured by measurement of luciferase activity as assayed by amount of light emitted when luciferin is added.

FIG. 2 shows a dose-response experiment in which cells were treated with phosphorothioate oligonucleotide 2570 (SEQ ID NO: 3), a compound that is targeted to the codon-12 point mutation of mutant (activated) H-ras RNA. The control oligonucleotide is a random phosphorothioate oligonucleotide, 20 bases long. Results are expressed as percentage of luciferase activity in transfected cells not treated with oligonucleotide. As the figure shows, treatment of cells with increasing concentrations of this oligonucleotide resulted in a dose-dependent inhibition of ras-luciferase activity in cells expressing either the mutant form or the normal form of ras-luciferase. However, careful examination of the data shows that at low concentrations, oligonucleotide 2570 displayed approximately threefold selectivity toward the mutant form of ras-luciferase as compared to the normal form. In fact, 2570 displayed an IC50 value for the mutant form of ras-luciferase of approximately 100 nM whereas the same compound displayed in IC50 value of approximately 250 nM for the unmutated form.

Figure 3:
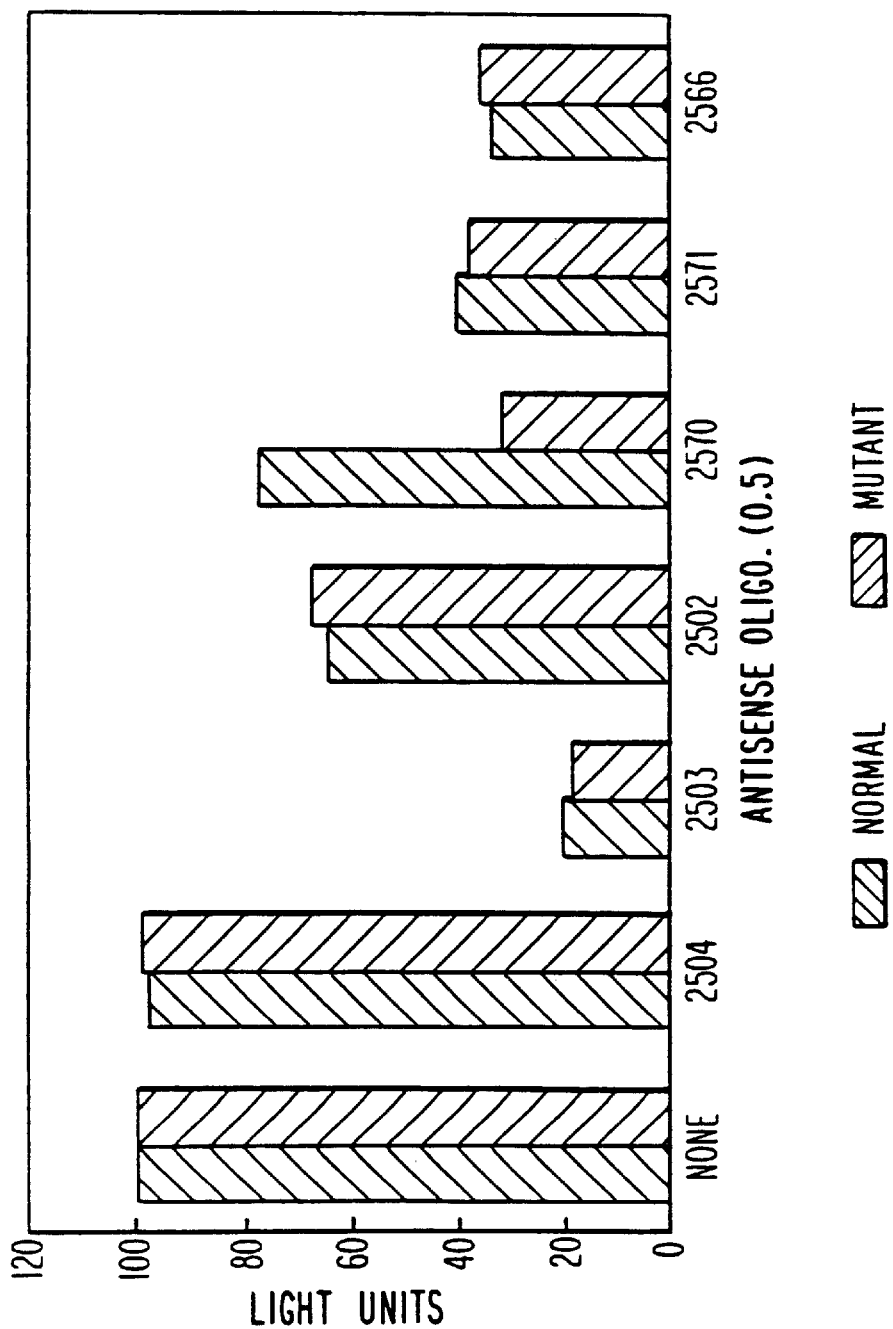
FIG. 3 is a bar graph showing single-dose inhibition of ras-luciferase fusion protein expression by antisense phosphorothioate compounds. Expression is measured by measurement of luciferase activity as assayed by amount of light emitted when luciferin is added.
Figure 4B:
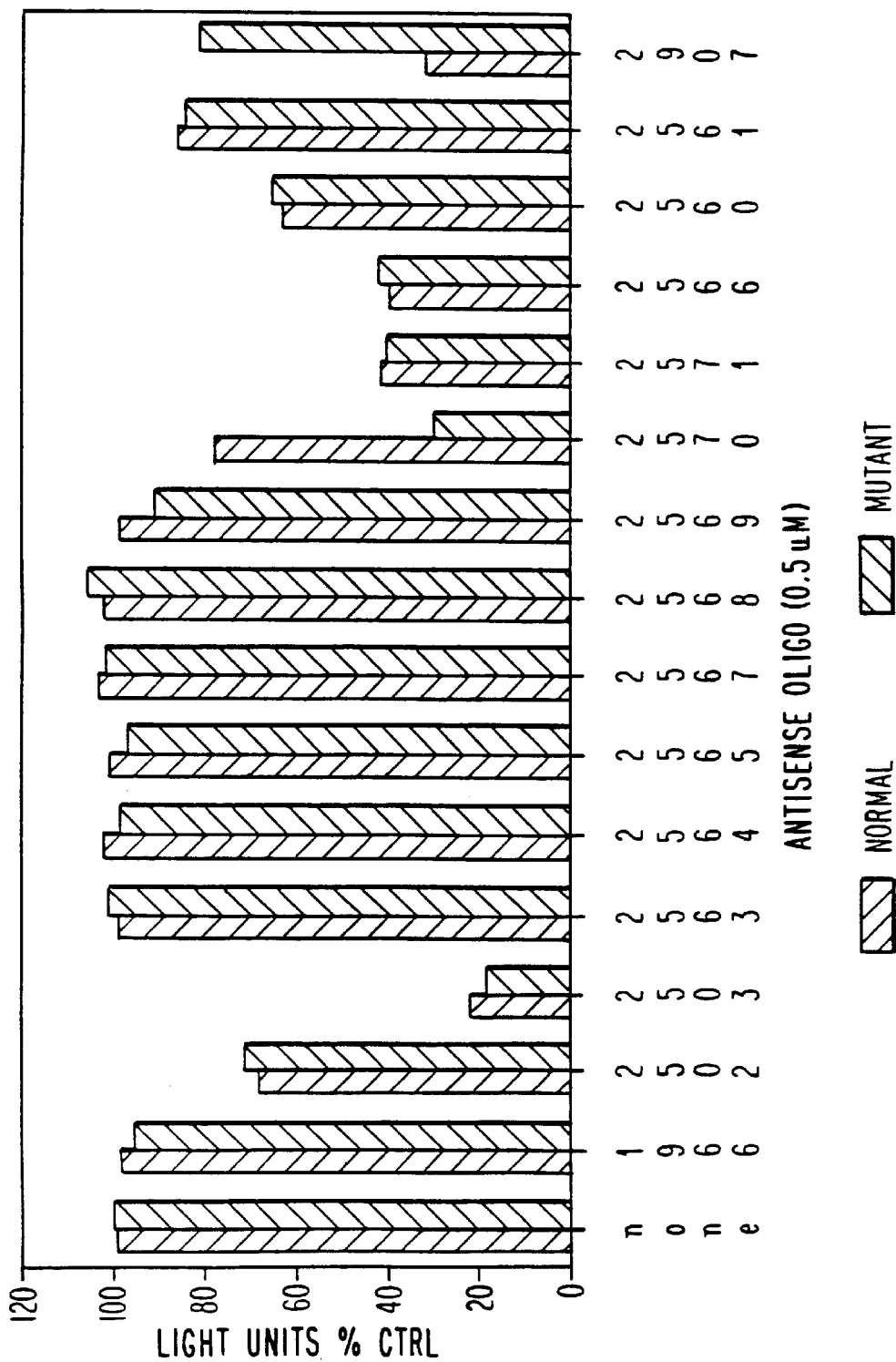
FIG. 4 is a table and bar graph summarizing data obtained for 13 antisense oligonucleotides specifically hybridizable with the activated H-ras gene. Shown for each oligonucleotide is its length, region of the activated ras gene to which it specifically hybridizes, and its activity in inhibiting expression of the ras-luciferase fusion protein.

FIG. 3 shows the results of a typical experiment in which cells expressing either the normal form or the mutant form of ras-luciferase were treated with a single dose (0.5 μM) of oligonucleotide targeted to either the translation initiation codon of H-ras or the codon-12 point mutation. The antisense phosphorothioate oligonucleotides tested are shown in Table 1. The control oligonucleotide (2504) is a random phosphorothioate oligonucleotide, 20 bases long. Results are expressed as percentage of luciferase activity in transfected cells not treated with oligonucleotide. As shown in FIG. 3, compound 2503 (SEQ ID NO: 2), targeted to the ras translational initiation codon, was most effective in inhibiting ras-luciferase activity. Of the three compounds targeted to the codon-12 point mutation of activated H-ras, only the 17-mer oligonucleotide 2570 (SEQ ID NO: 3) displayed selectivity toward the mutated form of ras-luciferase as compared to the normal form. This is also shown in FIG. 4, which summarizes data obtained with all 13 antisense oligonucleotides complementary to the activated H-ras gene, as well as a scrambled control oligonucleotide (1966) and a control oligonucleotide (2907) complementary to the codon-12 region of wild-type ras. Shown for each oligonucleotide is its length, region to which it is complementary, and its activity in suppressing expression of the ras-luciferase fusion protein. The longer phosphorothioates targeted to the codon-12 point mutation, while displaying substantial antisense activity toward ras-luciferase expression, did not demonstrate selective inhibition of expression of the mutant form of ras-luciferase. Phosphorothioate oligonucleotides targeted to the codon-12 point mutation that were less than 17 nucleotides in length did not show activity to either form of ras-luciferase. These results demonstrate effective antisense activity of phosphorothioate oligonucleotides targeted to ras sequences.

Figure 5A:
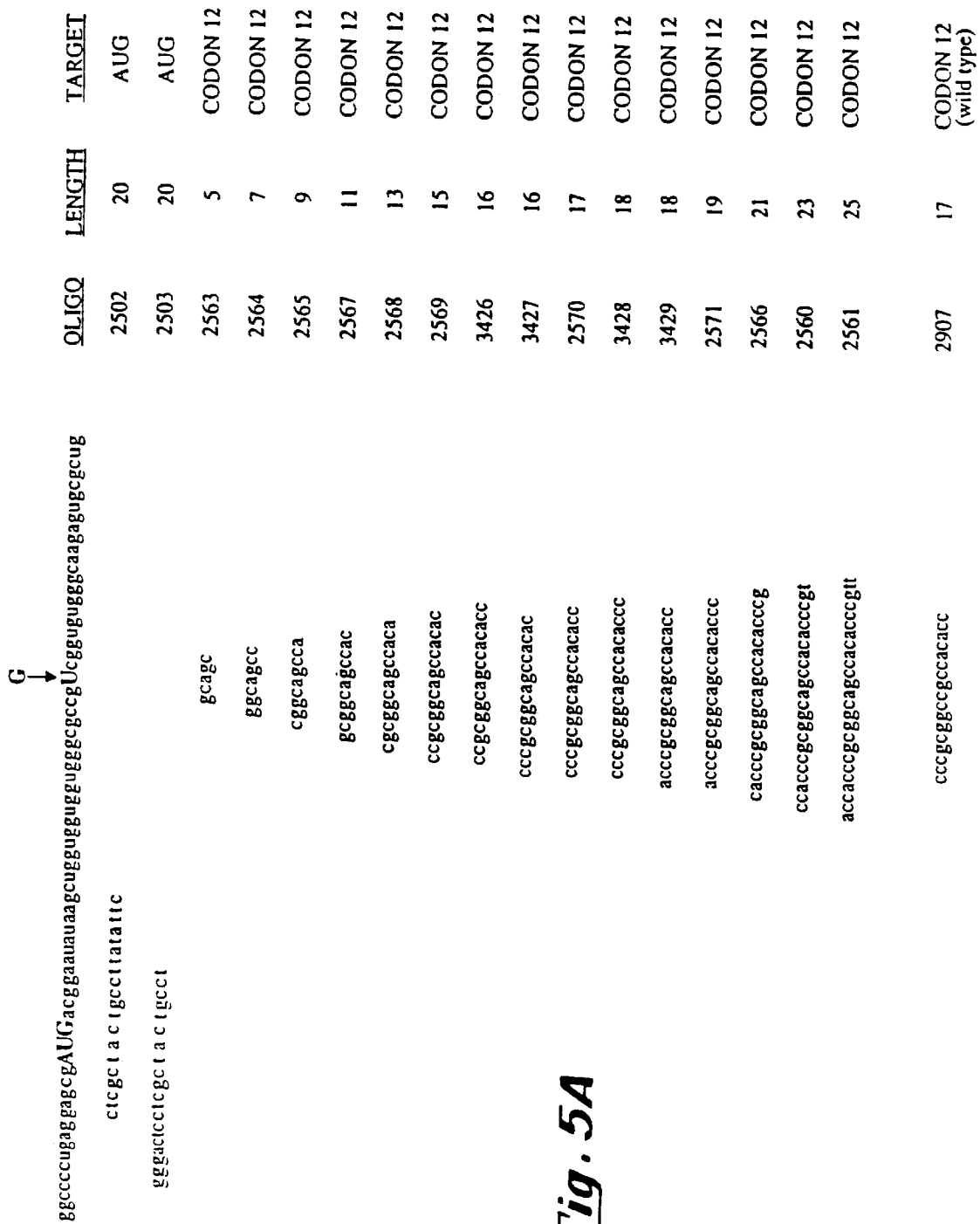
FIG. 5A shows two 20-mers (2502 and 2503) targeted to the AUG and a series of oligonucleotides from 5 to 25 nucleotides in length, targeted to codon 12.
Figure 5B:
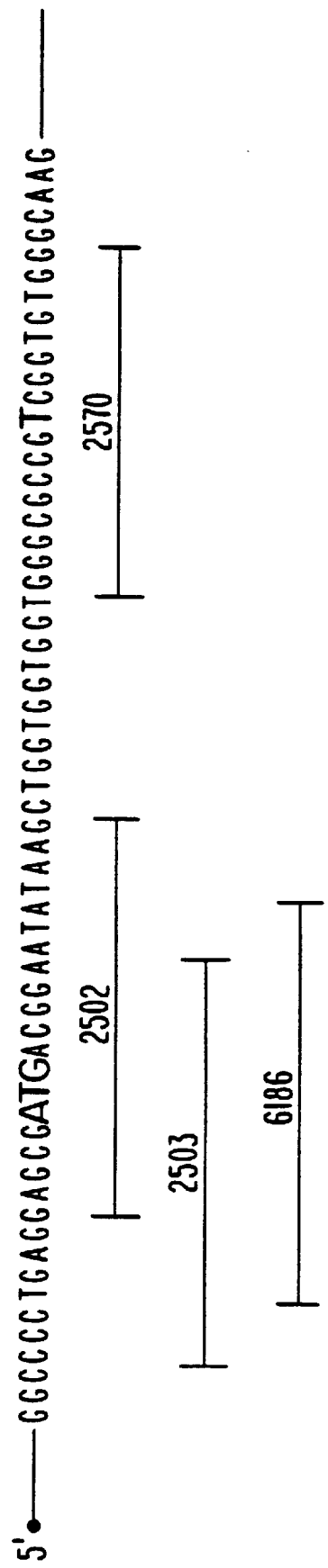
FIG. 5B shows oligonucleotides 2502, 2503, 6186 and 2570 in relation to the ras mRNA target sequence.
Figure 6:
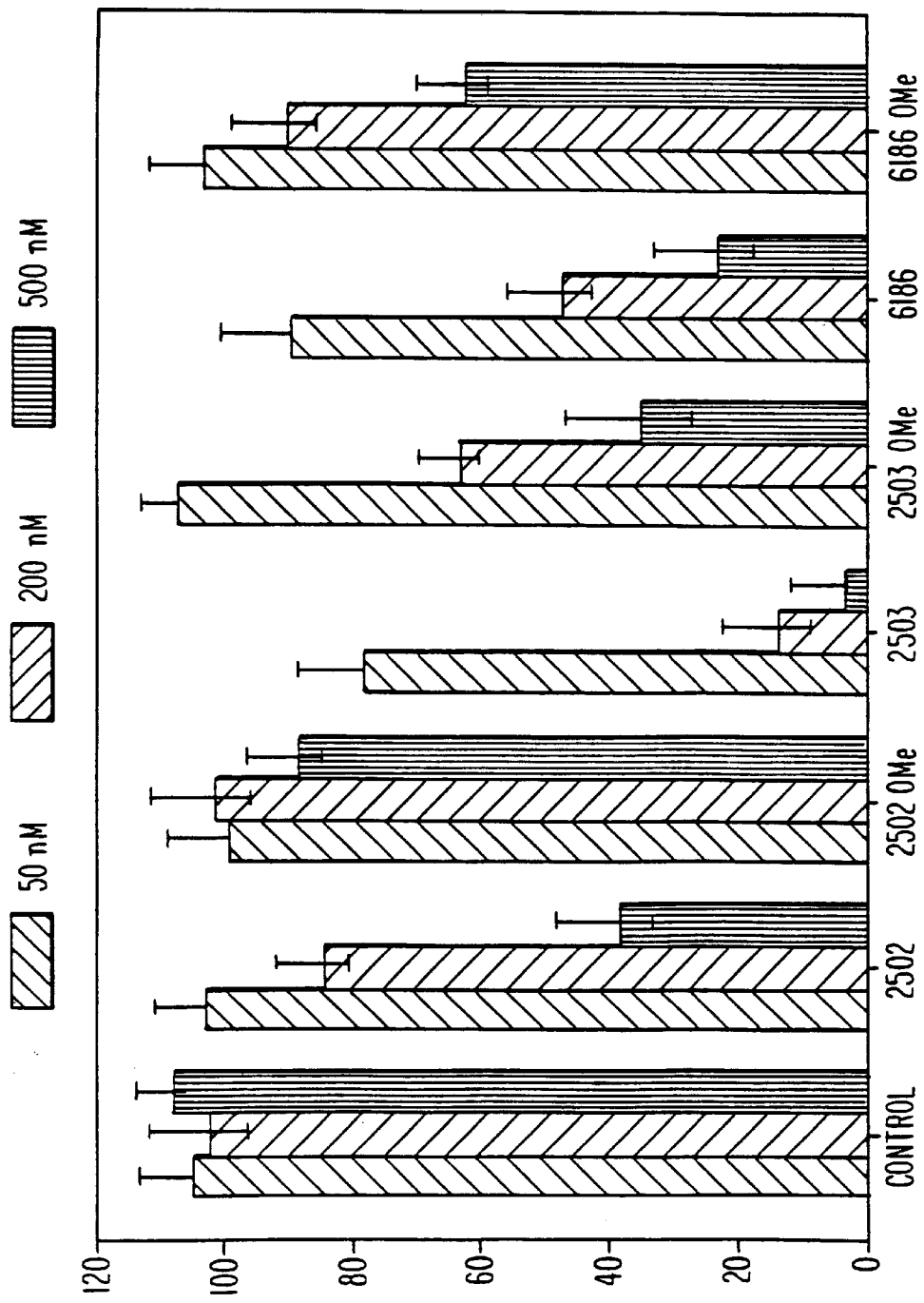
FIG. 6 is a bar graph showing inhibition of ras-luciferase by various doses of oligonucleotides 2502, 2503, 6186 and uniformly 2'-O-methylated versions of these phosphorothioate oligonucleotides.

Antisense oligonucleotides specifically hybridizable with the H-ras AUG: Three 20-base phosphorothioate oligonucleotides, targeted to the H-ras AUG codon, were compared for their ability to inhibit ras-luciferase expression in transient transfection assays as described in Examples 2–5. Results are shown in FIGS. 5A and 5B. These oligonucleotides, ISIS 2502 (SEQ ID NO: 1), 2503 (SEQ ID NO: 2) and 6186 (SEQ ID NO: 7) shown in Table 2, were tested for inhibition of ras-luciferase expression at a single dose (100 nM) in HeLa cells. All three AUG-targeted oligonucleotides were effective in inhibiting ras-luciferase expression. These three phosphorothioate oligonucleotides were also prepared with a 2'-O-methyl modification on each sugar. The 2'-O-methylated version of ISIS 2503 (SEQ ID NO: 2) also inhibited ras-luciferase expression. This is shown in FIG. 6.

TABLE 2

Antisense oligonucleotides targeted to mutant H-ras (Oligonucleotide sequences shown 5' to 3')

| OLIGO | LENGTH | TARGET | SEQUENCE | SEQ. ID NO. |
|---|---|---|---|---|
| 2502 | 20 | AUG | CTTATATTCCGTCATCGCTC | 1 |
| 2503 | 20 | AUG | TCCGTCATCGCTCCTCAGGG | 2 |
| 6186 | 20 | AUG | TATTCCGTCATCGCTCCTCA | 7 |
| 2563 | 5 | CODON 12 | CGACG | 8 |
| 2564 | 7 | CODON 12 | CCGACGG | 9 |
| 2565 | 9 | CODON 12 | ACCGACGGC | 10 |
| 2567 | 11 | CODON 12 | CACCGACGGCG | 11 |
| 2568 | 13 | CODCN 12 | ACACCGACGGCGC | 12 |
| 2569 | 15 | CODON 12 | CACACCGACGGCGCC | 13 |
| 3426 | 16 | CODON 12 | CCACACCGACGGCGCC | 14 |
| 3427 | 16 | CODON 12 | CACACCGACGGCGCCC | 15 |
| 2570 | 17 | CODON 12 | CCACACCGACGGCGCCC | 3 |
| 3428 | 18 | CODON 12 | CCCACACCGACGGCGCCC | 16 |
| 3429 | 18 | CODON 12 | CCACACCGACGGCGCCCA | 17 |
| 2571 | 19 | CODON 12 | CCCACACCGACGGCGCCCA | 4 |
| 2566 | 21 | CODON 12 | GCCCACACCGACGGCGCCCAC | 5 |
| 2560 | 23 | CODON 12 | TGCCCACACCGACGGCGCCCACC | 6 |
| 2561 | 25 | CODON 12 | TTGCCCACACCGACGGCGCCCACCA | 18 |
| 907 | 17 | CODON 12 (wild type) | CCACACCGCCGGCGCCC | 19 |

Figure 7:
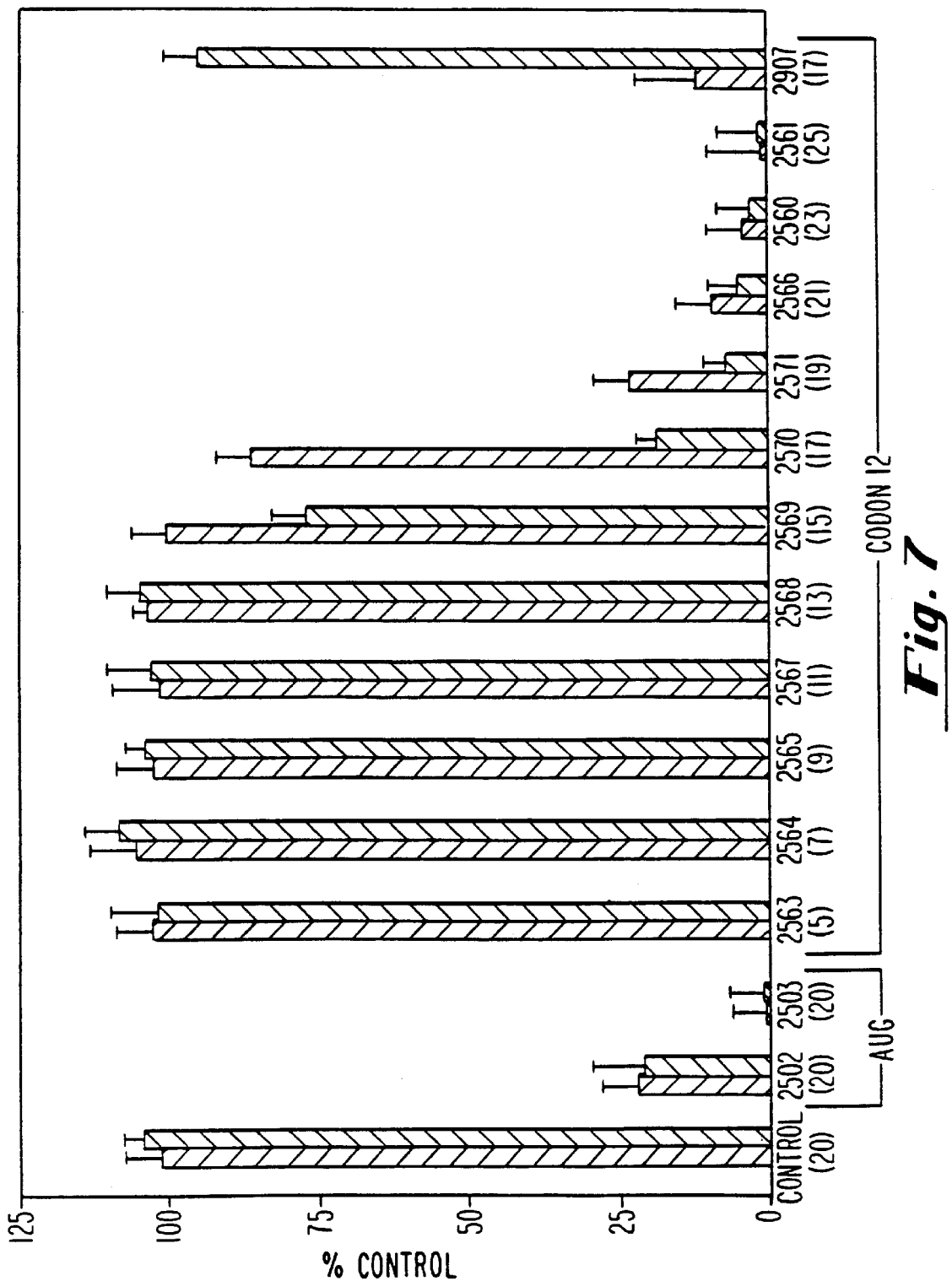
FIG. 7 is a bar graph showing antisense inhibition of mutant (striped bars) and normal (solid bars) ras-luciferase by antisense oligonucleotides of various lengths.
Figure 8A:
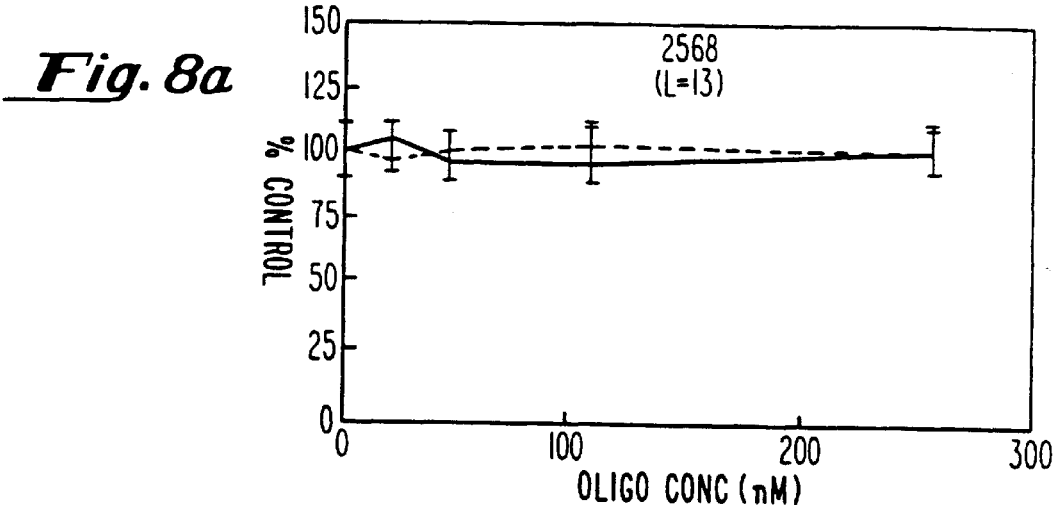
FIG. 8 is a series of 8 panels showing inhibition of ras in a dose-dependent manner. Solid lines are activity against wild-type, dotted lines show activity against activated ras.
Figure 8B:
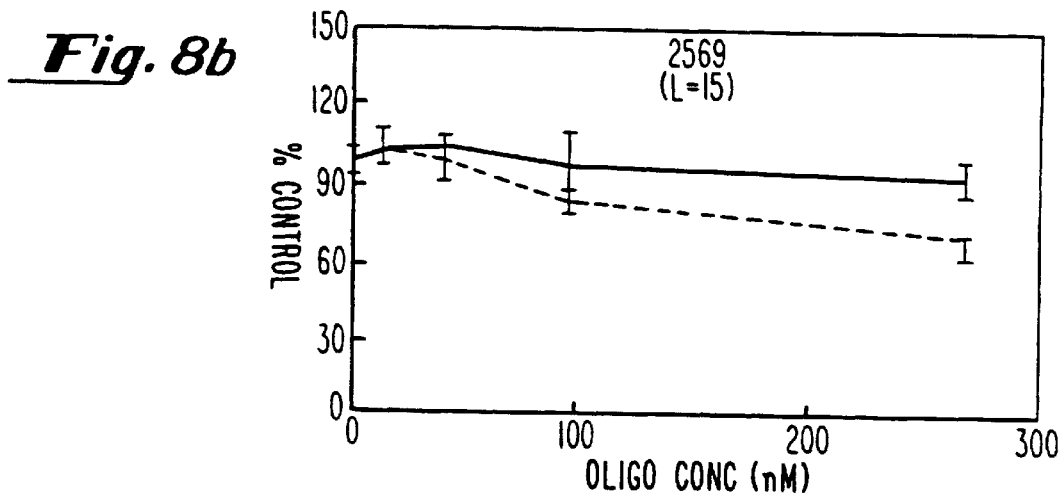
Figure 8C:
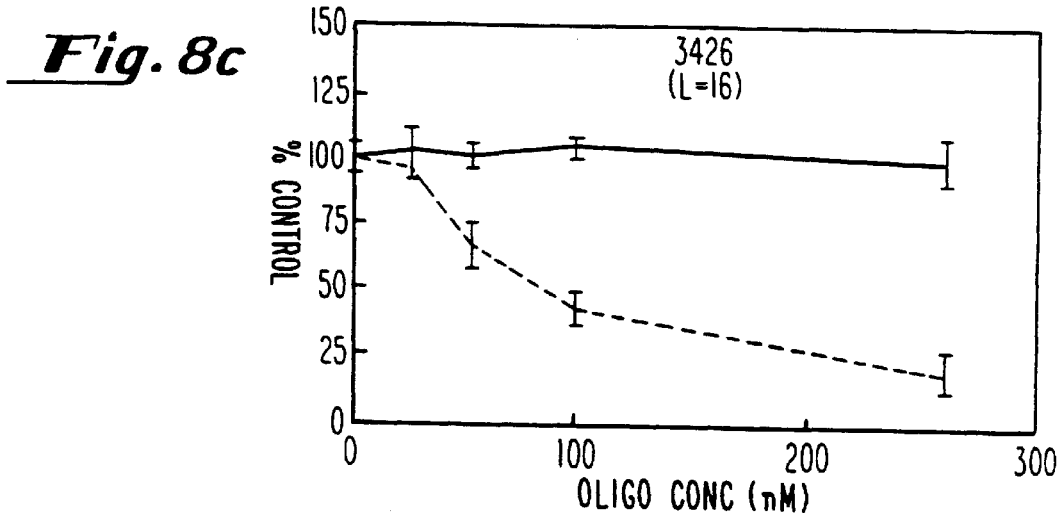
Figure 8D:
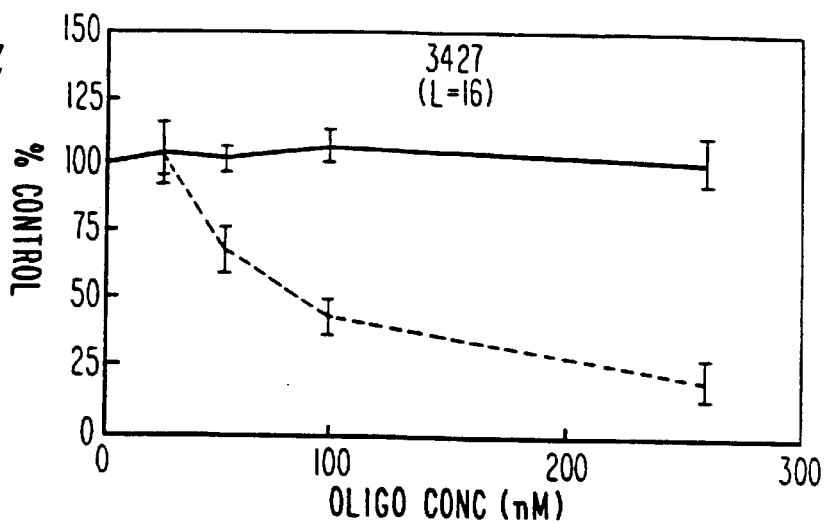
Figure 8E:
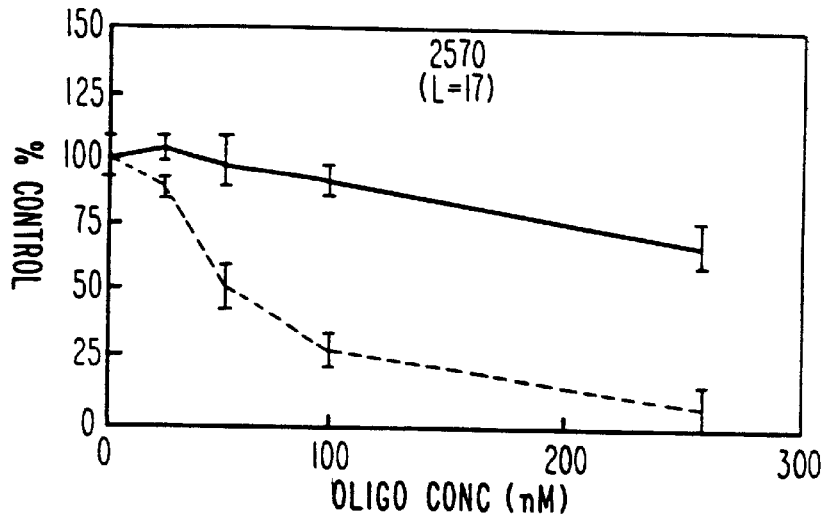
Figure 8F:
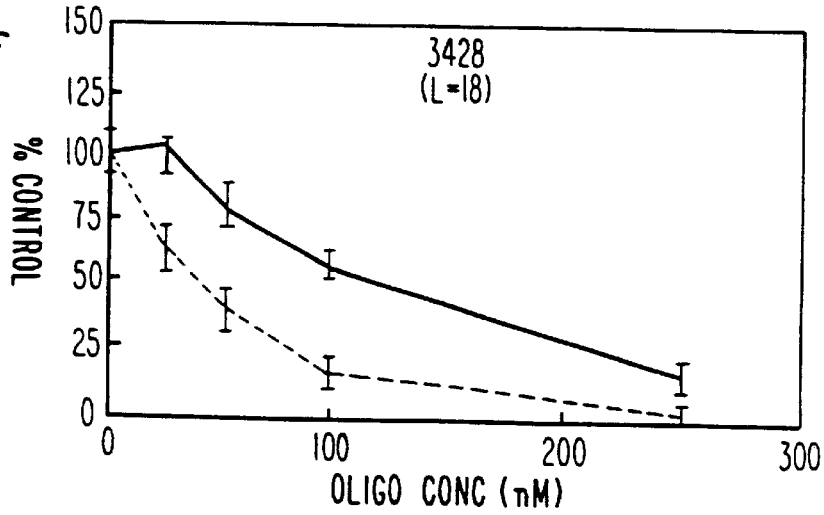
Figure 8G:
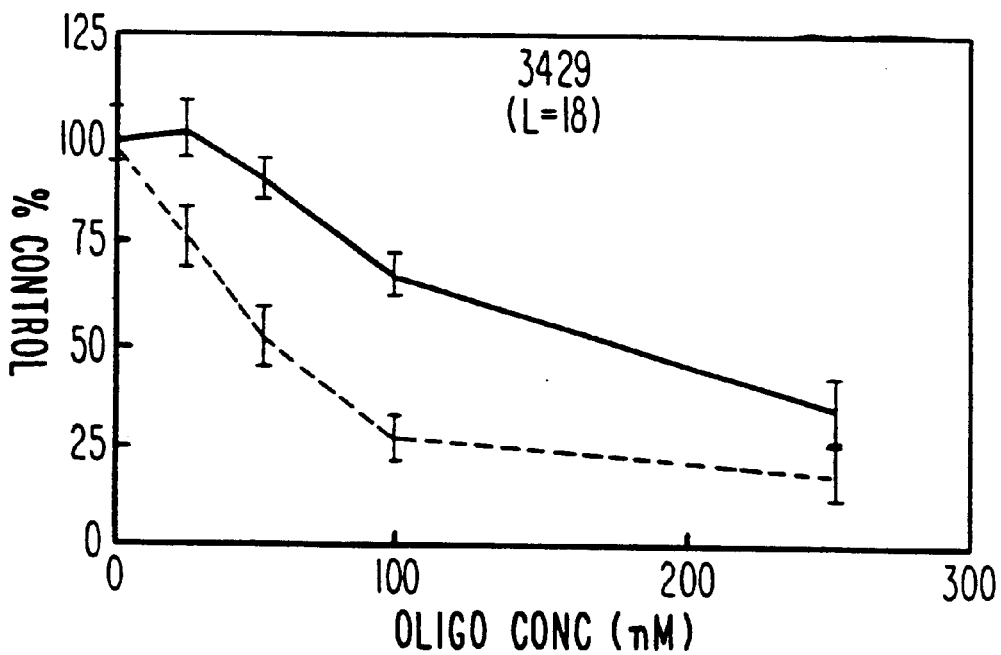
Figure 8H:
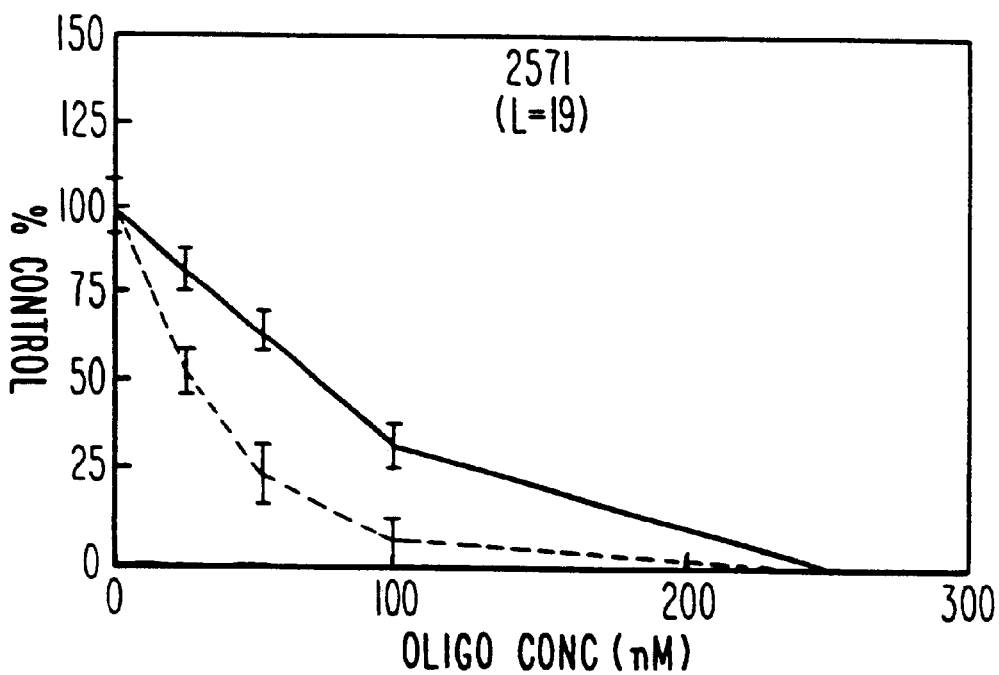

Oligonucleotide length affects antisense activity and specificity: Oligonucleotides targeted to the H-ras codon-12 point mutation also were effective in inhibiting expression of ras-luciferase. A series of eleven phosphorothioate oligonucleotides, ranging in length between 5 and 25 bases, were made and tested for ability to inhibit mutant and wild type ras-luciferase in transient transfection assays as described in Examples 2–5. The oligonucleotides are shown in Table 2. At 100 nM oligonucleotide concentration, oligonucleotides 15 bases or greater in length were found to inhibit expression of the mutant H-ras target. Selective inhibition of mutant over wild type ras-luciferase expression was observed for oligonucleotides between 15 and 19 bases in length. The maximum selectivity observed for inhibition of mutant ras-luciferase relative to wild type was for the 17-mer 2570 (SEQ ID NO: 3) and was approximately 4-fold. In order to demonstrate that 2570 was acting in a sequence-specific manner, a variant of this compound was tested (2907; SEQ ID NO: 19) in which the central adenosine residue was replaced with cytosine, making this oligonucleotide perfectly complementary to the wild type H-ras target. Hence, this oligonucleotide will contain a single mismatch at the center of the oligonucleotide/RNA duplex when fully hybridized to the mutant H-ras sequence. As shown in FIG. 7, oligonucleotide 2907 selectively inhibited expression of wild type ras-luciferase relative to mutant ras-luciferase, with the difference being approximately 5-fold at an oligonucleotide dosage of 100 nM.

Two 16-mers and two 18-mers complementary to the mutant codon-12 region (FIG. 5 and Table 2) were tested as described in Examples 2–5. FIG. 8 shows the results of an experiment in which antisense activity and mutant selectivity was determined for oligonucleotides of length 13, 15, 16, 17, 18 and 19 bases in a dose-dependent manner. The results obtained with these oligonucleotides demonstrated that the compounds that were active against mutant H-ras sequences also showed selectivity; oligonucleotides of length 16 (SEQ ID NO: 14 and SEQ ID NO: 15) and 17 bases (SEQ ID NO: 3) displayed the greatest selectivity (4- and 5-fold, respectively). The 13 base compound, 2568 (SEQ ID NO: 12), did not display antisense activity at any of the tested concentrations.

Chimeric 2'-O-methyl oligonucleotides with deoxy gaps: Based on the sequence of the mutant-selective 17-mer (2570), a series of chimeric phosphorothioate 2'-O-methyl oligonucleotides were synthesized in which the end regions consisted of 2'-O-methyl nucleosides and the central residues formed a "deoxy gap". The number of deoxy residues ranged from zero (full 2'-O-methyl) to 17 (full deoxy). These oligonucleotides are shown in Table 3.

TABLE 3

Chimeric phosphorothioate oligonucleotides having 2'-O-methyl ends (bold) and central deoxy gap (Mutant codon-12 target)

| OLIGO # | DEOXY | SEQUENCE | SEQ ID NO |
|---|---|---|---|
| 4122 | 0 | CCACACCGACGGCGCCC | 3 |
| 3975 | 1 | CCACACCGACGGCGCCC | 3 |
| 3979 | 3 | CCACACCGACGGCGCCC | 3 |
| 4236 | 4 | CCACACCGACGGCGCCC | 3 |
| 4242 | 4 | CCACACCGACGGCGCCC | 3 |
| 3980 | 5 | CCACACCGACGGCGCCC | 3 |
| 3985 | 7 | CCACACCGACGGCGCCC | 3 |
| 3984 | 9 | CCACACCGACGGCGCCC | 3 |
| 2570 | 17 | CCACACCGACGGCGCCC | 3 |

These oligonucleotides were characterized for hybridization efficiency as described in Example 6, ability to direct RNase H cleavage in vitro using mammalian RNase H as described in Example 8, and for antisense activity. Antisense activity against full length H-ras mRNA was determined using a transient co-transfection reporter gene system in which H-ras gene expression was monitored using a ras-responsive enhancer element linked to the reporter gene luciferase, as described in Example 9.

Hybridization of phosphorothioate antisense oligonucleotides to single stranded 25-mer RNA targets: FIG. 5 and Table 2 show the sequences of 15 phosphorothioate oligonucleotides targeted to activated H-ras mRNA containing the codon 12 G→U point mutation. These oligonucleotides range between 5 and 25 bases in length and are centered around the point mutation. Melting temperatures ($T_m$) for these antisense phosphorothioates against mutant and wild type 25-mer RNA targets at 4 $\mu$M oligonucleotide concentration were measured. $T_m$ increased with increasing chain length and, for any chain length, $T_m$ for hybridization to the mutant target was greater than that for the wild type target. Oligonucleotide 2907 is a phosphorothioate 17-mer variant of 2570 in which the central adenosine residue was replaced with cytosine, making this oligonucleotide perfectly complementary to the wild type H-ras target. As expected, the melting temperature for hybridization of this oligonucleotide to the wild type target was greater than that for the mutant target, which now contains a single mismatch in the oligonucleotide/RNA duplex at the site of the point mutation. For the 17-mer phosphorothioate (2570) that is perfectly complementary to the mutant H-ras target, thermodynamic parameters were also obtained from dependence of $T_m$ on oligonucleotide concentration. These data were used to determine the free energy difference ($\Delta\Delta G°_{37}$) between hybridization of oligonucleotides to the mutant target and to the wild type target. For a given oligonucleotide, $\Delta\Delta G°_{37}$ can be obtained from $T_m$ dependence on oligonucleotide concentration. Borer, P. N. et al., *J. Mol. Biol.* 1974, 86, 843–853. The $\Delta\Delta G°_{37}$ for 2570 was calculated to be +1.8 kcal/mole.

The maximum degree of selectivity that can be achieved for targeting mutant over wild type ras increases significantly as $\Delta\Delta G°_{37}$ increases. Therefore, chemical modifications of the antisense oligonucleotide which increase $\Delta\Delta G°_{37}$ enhance selectivity. One such modification is 2,6-diaminopurine, which is believed to bind more tightly than dA to U and less tightly than dA to G, and thus to increase $\Delta\Delta G°_{37}$ for the A-U→>A-G mismatch. The substrate requirements of RNase H can also be exploited to obtain selectivity according to the teachings of this invention. If the enzyme is unable to bind or cleave a mismatch, additional selectivity will be obtained beyond that conferred by $\Delta\Delta G°_{37}$ by employing chimeric oligonucleotides that place the RNAse H recognition site at the mismatch. This has been found to be the case; RNase H can indeed discriminate between a fully matched duplex and one containing a single mismatch.

Hybridization of "deoxy gap" oligonucleotides to short oligonucleotide targets: Hybridization analysis of the 2'-O-methyl deoxy gap series against a 25-mer synthetic oligoribonucleotide complement as described in Example 6 demonstrated that $T_m$ values for a given oligonucleotide correlated directly with 2'-O-methyl content. As 2'-O-methyl modifications were replaced with deoxy substituents, $T_m$ values were reduced at approximately 1.5° C. per modification. In these experiments, the $T_m$ values of the oligonucleotides containing 2'-O-methyl modifications were higher than the $T_m$ values of the full deoxy compound of the same sequence.

Hybridization of "deoxy gap" oligonucleotides to a structured RNA target: In further experiments oligonucleotides were hybridized to a larger H-ras target which contains a stable stem loop structure in the codon 12 region. Effects of 2'-O-methyl modifications on antisense hybridization to the structured H-ras target were determined by gel shift analysis as described in Example 7.

Figure 9A:
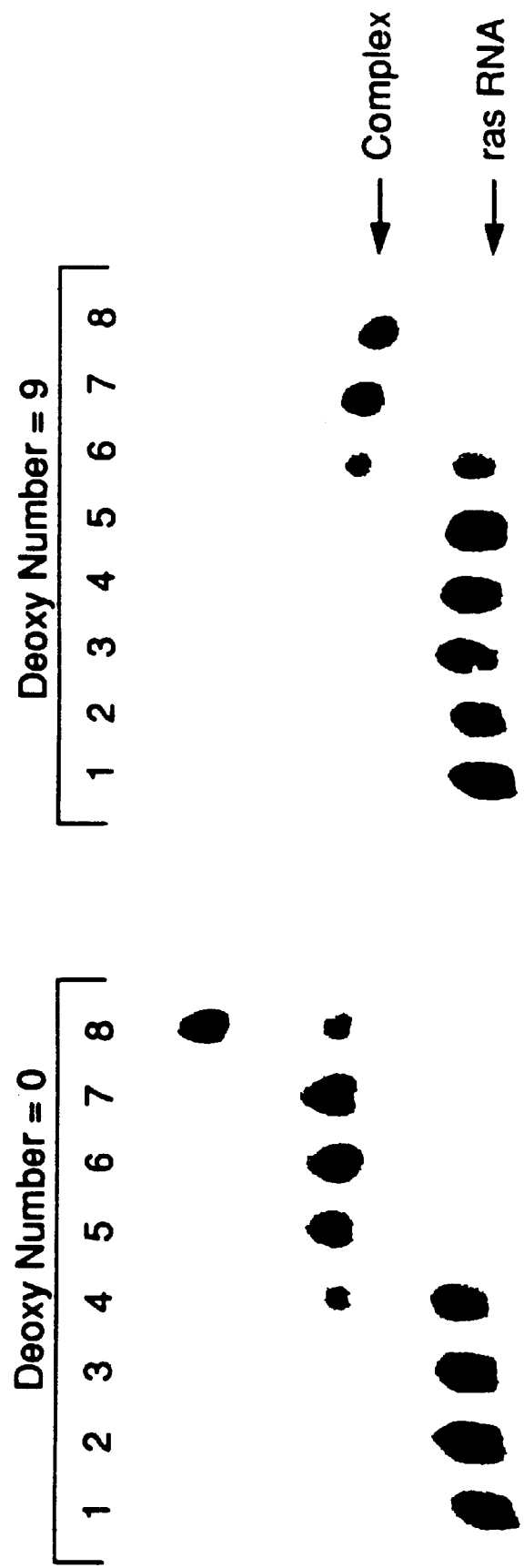
FIG. 9A is a gel shift analysis of hairpin target with uniform 2'-O-methyl oligonucleotide (deoxy number=0) and of hairpin target with a 2'-O-methyl chimeric oligonucleotide having a nine base deoxy gap (deoxy number=9) as a function of oligonucleotide concentration. Lanes 1–8 contain the following oligonucleotide concentrations: 1) none; 2) $10^{-11}$M; 3) $10^{-10}$M; 4) $10^{-9}$M; 5) $10^{-8}$M; 6) $10^{-7}$M; 7) $10^{-6}$M; 8) $10^{-5}$M.
Figure 9B:
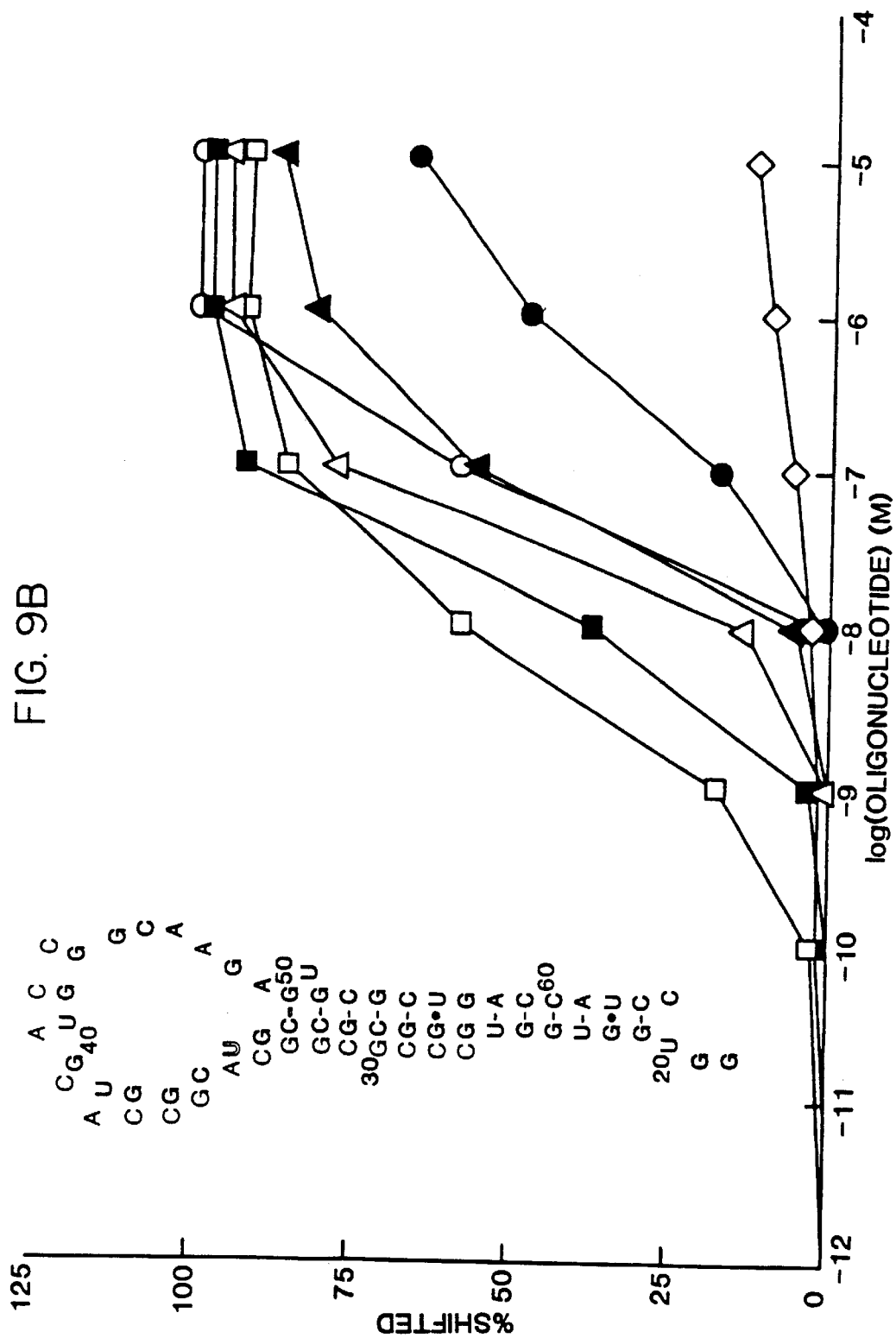
FIG. 9B is a graph showing fraction of hairpin target shifted vs. concentration of antisense oligonucleotide. ◇: Deoxy number=17; ●: Deoxy number=9; ▲: Deoxy number=7; O: Deoxy number=5; ∆: Deoxy number=3; ■.

As shown in FIG. 9, the full deoxy 17-mer formed the least stable duplex with the hairpin target; the full 2'-O-methyl 17-mer formed the most stable duplex. As deoxy gap size was decreased in these oligonucleotides, increasing the number of 2'-O-methyl residues increased duplex stability.

Secondary and tertiary structure of the RNA target affects hybridization of antisense oligonucleotides. A series of 11-mer chimeric oligonucleotides were made which hybridize to various regions of the ras hairpin target. ISIS 5055 hybridizes to the left side of the stem region (as the hairpin is displayed in FIG. 9). ISIS 5056 hybridizes to the left side of the loop. ISIS 5091 hybridizes to the right side of the loop and ISIS 5147 hybridizes to the right side of the stem. All are uniform phosphorothioates with centered 5-deoxy gaps flanked by 2'-O-methyl regions. Only the 11-mer targeted to the left side of the loop bound measurably to the target. The other 11-mers did not bind measurably. Longer versions of these oligonucleotides were also made; these 13-mer oligoribonucleotides all demonstrated measurable binding to the hairpin target, with the oligonucleotide targeted to the left side of the loop demonstrating the tightest binding in the gel-shift assay.

RNAse H cleavage directed by deoxy gapped oligonucleotides: Ability of 2'-O-methyl deoxy gap oligonucleotides to direct RNase H cleavage of a complementary RNA was determined in vitro using HeLa nuclear extracts as a source of RNase H as described in Example 8. As shown in FIG. 10, no cleavage was observed with the fully modified 2'-O-methyl oligonucleotide or one containing a single deoxy residue. Oligonucleotides with a deoxy length of three, four, five, seven or nine were able to direct RNase H cleavage. Deoxy gaps of five, seven or nine are preferred and gaps of seven or nine are most preferred.

Antisense activity of deoxy-gapped oligonucleotides against full length ras mRNA: The beneficial properties of enhanced target affinity conferred by 2'-O-methyl modifications can be exploited for antisense inhibition provided these compounds are equipped with RNase H-sensitive deoxy gaps of the appropriate length. 2'-O-methyl deoxy gap oligonucleotides were tested for antisense activity against the full length H-ras mRNA using the H-ras transactivation reporter gene system described in Example 9. Antisense experiments were performed initially at a single oligonucleotide concentration (100 nM). As shown in FIG. 11, chimeric 2'-O-methyl oligonucleotides containing deoxy gaps of five or more residues inhibited H-ras gene expression. These compounds displayed activities greater than that of the full deoxy parent compound.

Dose response experiments were performed using these active compounds, along with the 2'-O-methyl chimeras containing four deoxy residues. As shown in FIG. 11B, oligonucleotide-mediated inhibition of full-length H-ras by these oligonucleotides was dose-dependent. The most active compound was the seven-residue deoxy chimera, which displayed an activity approximately five times greater than that of the full deoxy oligonucleotide.

Shortened chimeric oligonucleotides: Enhanced target affinity conferred by the 2'-O-methyl modifications was found to confer activity on short chimeric oligonucleotides. A series of short 2'-O-methyl chimeric oligonucleotides were tested for $T_m$ and antisense activity vs. full length ras as described in Example 9. Table 4 shows $T_m$s for oligonucleotides 11, 13, 15 and 17 nucleotides in length, having deoxy gaps either 5 bases long or 7 bases long. In sharp contrast to the full deoxy 13-mer, both 2'-O-methyl chimeric 13-mers inhibited ras expression, and one of the 11-mers was also active. This is shown in FIG. 12.

TABLE 4

| LENGTH | $T_m$ (° C.) | SEQUENCE | SEQ ID NO: |
|---|---|---|---|
| 17 | 77.2 | CCACACCGACGGCGCCC | 3 |
| 15 | 69.8 | CACACCGACGGCGCC | 13 |
| 13 | 62.1 | ACACCGACGGCGC | 12 |

TABLE 4-continued

| LENGTH | $T_m$ (° C.) | SEQUENCE | SEQ ID NO: |
|---|---|---|---|
| 11 | 47.3 | CACCGACGGCG | 11 |
| 17 | 74.6 | CCACACCGACGGCGCCC | 3 |
| 15 | 66.2 | CACACCGACGGCGCC | 13 |
| 13 | 58.0 | ACACCGACGGCGC | 12 |
| 11 | 27.7 | CACCGACGGCG | 11 |

Relative antisense activity and ability to activate RNase H cleavage in vitro by chimeric 2'-O-methyl oligonucleotides is well correlated with deoxy length (FIG. 13).

Asymmetrical deoxy gaps: It is not necessary that the deoxy gap be in the center of the chimeric molecule. It was found that chimeric molecules having the nucleotides of the region at one end modified at the 2' position to enhance binding and the remainder of the molecule unmodified (2'deoxy) can still inhibit ras expression. Oligonucleotides of SEQ ID NO: 3 (17-mer complementary to mutant codon 12) in which a 7-deoxy gap was located at either the 5' or 3' side of the 17-mer, or at different sites within the middle of the molecule, all demonstrated RNase H activation and antisense activity. However, a 5-base gap was found to be more sensitive to placement, as some gap positions rendered the duplex a poor activator of RNase H and a poor antisense inhibitor. Therefore, a 7-base deoxy gap is preferred.

Other sugar modifications: The effects of other 2' sugar modifications besides 2'-O-methyl on antisense activity in chimeric oligonucleotides have been examined. These modifications are listed in Table 5, along with the $T_m$ values obtained when 17-mer oligonucleotides having 2'-modified nucleotides flanking a 7-base deoxy gap were hybridized with a 25-mer oligoribonucleotide complement as described in Example 6. A relationship was observed for these oligonucleotides between alkyl length at the 2' position and $T_m$. As alkyl length increased, $T_m$ decreased. The 2'-fluoro chimeric oligonucleotide displayed the highest $T_m$ of the series.

TABLE 5

Correlation of $T_m$ with Antisense Activity
2'-modified 17-mer with 7-deoxy gap
CCACACCGACGGCGCCC (SEQ ID NO: 3)

| 2' MODIFICATION | $T_m$ (° C.) | IC50 (nM) |
|---|---|---|
| Deoxy | 64.2 | 150 |
| O-Pentyl | 68.5 | 150 |
| O-Propyl | 70.4 | 70 |
| O-Methyl | 74.7 | 20 |
| Fluoro | 76.9 | 10 |

These 2' modified oligonucleotides were tested for antisense activity against H-ras using the transactivation reporter gene assay described in Example 9. As shown in FIG. 14 and Table 5, all of these 2' modified chimeric compounds inhibited ras expression, with the 2'-fluoro 7-deoxy-gap compound the most active. A 2'-fluoro chimeric oligonucleotide with a centered 5-deoxy gap was also active.

Chimeric phosphorothioate oligonucleotides having SEQ ID NO: 3 having 2'-O-propyl regions surrounding a 5-base or 7-base deoxy gap were compared to 2'-O-methyl chimeric oligonucleotides. ras expression in T24 cells was inhibited by both 2'-O-methyl and 2'-O-propyl chimeric oligonucleotides with a 7-deoxy gap and a uniform phosphorothioate backbone. When the deoxy gap was decreased to five nucleotides, only the 2'-O-methyl oligonucleotide inhibited ras expression.

Antisense oligonucleotide inhibition of H-ras gene expression in cancer cells: Two phosphorothioate oligonucleotides (2502, 2503) complementary to the ras AUG region were tested as described in Example 10, along with chimeric oligonucleotides (4998, 5122) having the same sequence and 7-base deoxy gaps flanked by 2'-O-methyl regions. These chimeric oligonucleotides are shown in Table 6.

TABLE 6

Chimeric phosphorothioate oligonucleotides having 2'-O-methyl ends (bold) and central deoxy gap (AUG target)

| OLIGO # | DEOXY | SEQUENCE | SEQ ID NO: |
|---|---|---|---|
| 2502 | 20 | CTTATATTCCGTCATCGCTC | 1 |
| 4998 | 7 | CTTATATTCCGTCATCGCTC | 1 |
| 2503 | 20 | TCCGTCATCGCTCCTCAGGG | 2 |
| 5122 | 7 | TCCGTCATCGCTCCTCAGGG | 2 |

Compound 2503 inhibited ras expression in T24 cells by 71%, and the chimeric compound (4998) inhibited ras mRNA even further (84% inhibition). Compound 2502, also complementary to the AUG region, decreased ras RNA levels by 26% and the chimeric version of this oligonucleotide (5122) demonstrated 15% inhibition. Also included in this assay were two oligonucleotides targeted to the mutant codon 12. Compound 2570 (SEQ ID NO: 3) decreased ras RNA by 82% and the 2'-O-methyl chimeric version of this oligonucleotide with a seven-deoxy gap (3985) decreased ras RNA by 95%.

Oligonucleotides 2570 and 2503 were also tested to determine their effects on ras expression in HeLa cells, which have a wild-type (i.e., not activated) H-ras codon 12. While both of these oligonucleotides inhibited ras expression in T24 cells (having activated codon 12), only the oligonucleotide (2503) specifically hybridizable with the ras AUG inhibited ras expression in HeLa cells. Oligonucleotide 2570 (SEQ ID NO: 3), specifically hybridizable with the activated codon 12, did not inhibit ras expression in HeLa cells, because these cells lack the activated codon-12 target.

Oligonucleotide 2570, a 17-mer phosphorothioate oligonucleotide complementary to the codon 12 region of activated H-ras, was tested for inhibition of ras expression (as described in Example 10) in T24 cells along with chimeric phosphorothioate 2'-O-methyl oligonucleotides 3980, 3985 and 3984, which have the same sequence as 2570 and have deoxy gaps of 5, 7 and 9 bases, respectively (shown in Table 3). The fully 2'-deoxy oligonucleotide 2570 and the three chimeric oligonucleotides decreased ras mRNA levels in T24 cells. Compounds 3985 (7-deoxy gap) and 3984 (9-deoxy gap) decreased ras mRNA by 81%; compound 3980 (5-deoxy gap) decreased ras mRNA by 61%. Chimeric oligonucleotides having this sequence, but having 2'-fluoro-modified nucleotides flanking a 5-deoxy (4689) or 7-deoxy (4690) gap, inhibited ras mRNA expression in T24 cells, with the 7-deoxy gap being preferred (82% inhibition, vs 63% inhibition for the 2'-fluoro chimera with a 5-deoxy gap).

Antisense oligonucleotide inhibition of proliferation of cancer cells: Three 17-mer oligonucleotides having the same sequence (SEQ ID NO: 3), complementary to the codon 12 region of activated ras, were tested for effects on T24 cancer cell proliferation as described in Example 11. 3985 has a 7-deoxy gap flanked by 2'-O-methyl nucleotides, and 4690 has a 7-deoxy gap flanked by 2'-F nucleotides (all are phosphorothioates). Effects of these oligonucleotides on cancer cell proliferation correlated well with their effects on ras mRNA expression shown by Northern blot analysis: oligonucleotide 2570 inhibited cell proliferation by 61%, the 2'-O-methyl chimeric oligonucleotide 3985 inhibited cell proliferation by 82%, and the 2'-fluoro chimeric analog inhibited cell proliferation by 93%.

In dose-response studies of these oligonucleotides on cell proliferation, the inhibition was shown to be dose-dependent in the 25 nM–100 nM range. IC50 values of 44 nM, 61 nM and 98 nM could be assigned to oligonucleotides 4690, 3985 and 2570, respectively. The random oligonucleotide control had no effect at the doses tested.

The effect of ISIS 2570 on cell proliferation was cell type-specific. The inhibition of T24 cell proliferation by this oligonucleotide was four times as severe as the inhibition of HeLa cells by the same oligonucleotide (100 nM oligonucleotide concentration). ISIS 2570 is targeted to the activated (mutant) ras codon 12, which is present in T24 but lacking in HeLa cells, which have the wild-type codon 12.

Chimeric backbone-modified oligonucleotides: Oligonucleotides discussed in previous examples have had uniform phosphorothioate backbones. The 2'modified chimeric oligonucleotides discussed above are not active in uniform phosphodiester backbones. A chimeric oligonucleotide was synthesized (ISIS 4226) having 2'-O-methyl regions flanking a 5-nucleotide deoxy gap, with the gap region having a P=S backbone and the flanking regions having a P=O backbone. Another chimeric oligonucleotide (ISIS 4223) having a P=O backbone in the gap and P=S in flanking regions was also made. These oligonucleotides are shown in Table 7.

Additional oligonucleotides were synthesized, completely 2'deoxy and having phosphorothioate backbones containing either a single phosphodiester (ISIS 4248), two phosphodiesters (ISIS 4546), three phosphodiesters (ISIS 4551), four phosphodiesters (ISIS 4593), five phosphodiesters (ISIS 4606) or ten phosphodiester linkages (ISIS-4241) in the center of the molecule. These oligonucleotides are also shown in Table 7.

TABLE 7

Chimeric backbone (P = S/P = O) oligonucleotides having 2'-O-methyl ends (bold) and central deoxy gap (backbone linkages indicated by s (P = S) or o (P = O) Mutant codon-12 target

| OLIGO # | P = S | SEQUENCE | SEQ ID NO: |
|---|---|---|---|
| 2570 | 16 | CsCsAsCsAsCsCsGsAsCsGsGsCsGsCsC | 3 |
| 4226 | 5 | CoCoAoCoAoCsCsGsAsCsGoGoCoGoCoCoC | 3 |
| 4233 | 11 | CsCsAsCsAsCoCoGoAoCoGsGsCsGsCsC | 3 |
| 4248 | 15 | CsCsAsCsAsCsCsGoAoCsGsGsCsGsCsC | 3 |
| 4546 | 14 | CsCsAsCsAsCsCsGoAoCoGsGsCsGsCsC | 3 |
| 4551 | 13 | CsCsAsCsAsCsCsGoAoCoGoGsCsGsCsC | 3 |
| 4593 | 12 | CsCsAsCsAsCsCoGoAoCoGoGsCsGsCsC | 3 |
| 4606 | 11 | CsCsAsCsAsCsCoGoAoCoGoGoCsGsCsC | 3 |
| 4241 | 6 | CsCsAsCoAoCoCoGoAoCoGoGoCoGsCsC | 3 |

Oligonucleotides were incubated in crude HeLa cellular extracts at 37° C. to determine their sensitivity to nuclease degradation as described in Dignam et al., *Nucleic Acids Res. 1983, 11, 1475–1489.* The oligonucleotide (4233) with a five-diester gap between phosphorothioate/2'-O-methyl wings had a $T_{1/2}$ of 7 hr. The oligonucleotide with a five-phosphorothioate gap in a phosphorothioate/2'-O-methyl molecule had a $T_{1/2}$ of 30 hours. In the set of oligonucleotides having one to ten diester linkages, the oligonucleotide (4248) with a single phosphodiester linkage was as stable to nucleases as was the full-phosphorothioate molecule, ISIS 2570, showing no degradation after 5 hours in HeLa cell extract. Oligonucleotides with two-, three and four-diester gaps had $T_{1/2}$ of approximately 5.5 hours, 3.75 hours, and 3.2 hours, and oligonucleotides with five or ten deoxy linkages had $T_{1/2}$ of 1.75 hours and 0.9 hours, respectively.

Antisense activity of chimeric backbone-modified oligonucleotides: A uniform phosphorothioate backbone is not required for antisense activity. ISIS 4226 and ISIS 4233 were tested in the ras-luciferase reporter system for effect on ras expression as described in Examples 2–5, along with ISIS 2570 (fully phosphorothioate/all deoxy), ISIS 3980 (fully phosphorothioate, 2'-O-methyl wings with deoxy gap) and ISIS 3961 (fully phosphodiester, 2'-O-methyl wings with deoxy gap). All of the oligonucleotides having a P=S (i.e., nuclease-resistant) gap region inhibited ras expression. This is shown in FIG. 15. The two completely 2'deoxy oligonucleotides having phosphorothioate backbones containing either a single phosphodiester (ISIS 4248) or ten phosphodiester linkages (ISIS 4241) in the center of the molecule were also assayed for activity. The compound containing a single P=O was just as active as a full P=S molecule, while the same compound containing ten P=O was completely inactive.

Chimeric phosphorothioate oligonucleotides of SEQ ID NO: 3 were made, having a phosphorothioate backbone in the 7-base deoxy gap region only, and phosphodiester in the flanking regions, which were either 2'-O-methyl or 2'-O-propyl. The oligonucleotide with the 2'-O-propyl diester flanking regions was able to inhibit ras expression.

Inhibition of ras-luciferase gene expression by antisense oligonucleotides containing modified bases: A series of antisense phosphorothioate oligonucleotides complementary to the codon-12 point mutation of activated ras were synthesized as described, having a 2-(amino)adenine at the position complementary to the uracil of the mutated codon 12. Because the amino group at the 2-position of the adenine is able to hydrogen bond with the oxygen in the 2-position on the uracil, three hydrogen bonds instead of the usual two are formed. This serves to greatly stabilize the hybridization of the 2-(amino)adenine-modified antisense oligonucleotide to the activated ras gene, while destabilizing or having no net effect on the stability of this oligonucleotide to the wild-type codon 12, because of the modified A-G mismatch at this position. This increases the specificity of the modified oligonucleotide for the desired target.

An oligonucleotide having a single 2,6-(diamino) adenosine at this position in an otherwise unmodified uniform phosphorothioate 17-mer (sequence identical to 2570, SEQ ID NO: 3) was found to be at least as effective an RNase H substrate as the 2570 sequence. It is therefore expected to be an effective antisense molecule. An oligonucleotide having a single 2,-(diamino)adenosine at this position in a deoxy gapped phosphorothioate oligonucleotide of the same sequence also demonstrates RNase H activation.

in vivo anti-tumor data: ISIS 2503 (SEQ ID NO: 2) has been evaluated for activity against human tumors in vivo as described in Examples 13 and 14. These studies employed a human lung adenocarcinoma cell line (A549) which was subcutaneously implanted into nude mice, resulting in tumor growth at site of implantation. Since these cells do not contain a mutation in the Ha-ras gene, but do express normal Ha-ras, only the AUG-directed oligonucleotide ISIS 2503 was evaluated for anti-tumor activity.

In the first study, phosphorothioate oligonucleotides in saline were administered by intraperitoneal injection at a dosage of 20 mg/kg. Drug treatment was initiated at the time tumors first became visible (28 days following tumor cell inoculation) and treatments were performed every other day. As shown in FIG. 16, no effect on tumor growth was observed after treatment with the unrelated control phosphorothioate oligonucleotide ISIS 1082. However, significant inhibition of tumor growth was observed for the Ha-ras-specific oligonucleotide ISIS 2503 (SEQ ID NO: 2). The anti-tumor effects of the Ha-ras compound were first observed 20 days following initiation of drug treatment and continued throughout the duration of the study.

In a second study, phosphorothioate oligonucleotides were prepared in a cationic lipid formulation (DMRIE:DOPE) and administered by subcutaneous injection as described in Example 15. Drug treatment was initiated one week following tumor cell inoculation and was performed three times a week for only four weeks. As was observed in the first study, administration of the Ha-ras-specific compound ISIS 2503 (SEQ ID NO: 2) caused a marked reduction in tumor growth whereas the unrelated control oligonucleotide (ISIS 1082) had no significant effect (FIG. 17). Reduction in tumor volume was first observed 20 days following appearance of visible tumors and continued over time throughout the remainder of the study.

Stability of 2'-modified phosphodiester oligonucleotides in cells: Modification of oligonucleotides to confer nuclease stability is required for antisense activity in cells. Certain modifications at the 2' position of the sugar have been found to confer nuclease resistance sufficient to elicit antisense effects in cells without any backbone modification. As shown in FIG. 18, a uniformly 2'-propoxy modified phosphodiester oligonucleotide (SEQ ID NO: 3) was found to inhibit Ha-ras expression in T24 cells, 24 hours after administration, at a level equivalent to a phosphorothioate 2'-deoxyoligonucleotide having the same sequence. Uniform 2'-methoxy phosphodiester oligonucleotide also showed some activity. 2'-pentoxy modifications were found to be at least as active as the 2'-propoxy.

Antisense Oligonucleotides Active Against Ki-ras:

Oligonucleotides were designed to be complementary to the 5'-untranslated region, 3'-untranslated region and coding region of the human Ki-ras oncogene. McGrath, J. P. et al., (1983) *Nature* 304, 501–506. Of the latter, oligonucleotides were targeted to codons 12 and 61 which are known sites of mutation that lead to Ki-ras-mediated transformation, and also to codon 38, which is not known to be involved in transformation. The oligonucleotides are shown in Table 8.

TABLE 8

Antisense Oligonucleotides Complementary to Human Ki-ras

| ISIS # | SEQUENCE | TARGET | SEQ ID NO: |
|---|---|---|---|
| 6958 | CTG CCT CCG CCG CCG CGG CC | 5' UTR/5' cap | 20 |
| 6957 | CAG TGC CTG CGC CGC GCT CG | 5'-UTR | 21 |
| 6956 | AGG CCT CTC TCC CGC ACC TG | 5'-UTR | 22 |
| 6953 | TTC AGT CAT TTT CAG CAG GC | AUG | 23 |
| 6952 | TTA TAT TCA GTC ATT TTC AG | AUG | 24 |
| 6951 | CAA GTT TAT ATT CAG TCA TT | AUG | 25 |
| 6950 | GCC TAC GCC ACC AGC TCC AAC | Codon 12 (WT) | 26 |
| 6949 | CTA CGC CAC CAG CTC CA | Codon 12 (WT) | 27 |
| 6948 | G TAC TCC TCT TGA CCT GCT GT | Codon 61 (WT) | 28 |
| 6947 | CCT GTA GGA ATC CTC TAT TGT | Codon 38 | 29 |
| 6946 | GGT AAT GCT AAA ACA AAT GC | 3'-UTR | 30 |
| 6945 | GGA ATA CTG GCA CTT CGA GG | 3'-UTR | 31 |
| 7453 | TAC GCC AAC AGC TCC | Codon 12 (G→T mut.) | 32 |
| 7679 | TTT TCA GCA GGC CTC TCT CC | 5'-UTR/AUG | 33 |

Twelve Ki-ras-specific oligonucleotides were screened for antisense activity against three colon carcinoma cell lines that contain a mutation at codon 12 in the Ki-ras oncogene and evaluated by measurement of Ki-ras mRNA levels. As shown in FIG. 19, half of the tested compounds displayed significant activity (at least 40% inhibition) against the Ki-ras transcript, with the most active compounds being targeted to the 5'- and 3'-untranslated regions. However, significant inhibition of Ki-ras expression was also observed for compounds directed against wild type codons 12 and 61. Compounds that displayed significant activity were effective against all three carcinoma cell lines tested.

Dose response analysis of these compounds demonstrated that ISIS 6958 and ISIS 6957, both of which target the 5'-UTR, are the most potent inhibitors of Ki-ras in this series of oligonucleotides. These oligonucleotides were examined for their ability to inhibit proliferation of Ki-ras transformed cell lines. The colon carcinoma cell line SW480 was treated with a single dose of oligonucleotide (200 nM) and cell number was determined over a five-day period. As shown in FIG. 20, both Ki-ras specific oligonucleotides were effective inhibitors of proliferation of SW480 cells, with ISIS 6957 (SEQ ID NO: 21) showing greater activity than ISIS 6958 (SEQ ID NO: 20). This difference in activity correlates well with the inhibition of Ki-ras mRNA expression (FIG. 19).

Selectivity of inhibition of mutant Ki-ras relative to normal Ki-ras: Oligonucleotides targeted to Ki-ras have been examined for their ability to selectively inhibit mutant Ki-ras relative to normal Ki-ras. Two cell lines were employed: the SW480 cell line that expresses mutant Ki-ras (codon 12, G to T transversion) and a cell line (HeLa) that expresses normal Ki-ras. Two oligonucleotides were tested: ISIS 6957, SEQ ID NO: 21, a 20 mer phosphorothioate targeted to the 5'-untranslated region of Ki-ras, and ISIS 7453, SEQ ID NO: 32, a 15 mer phosphorothioate targeted to the Ki-ras codon 12 region. Ki-ras mRNA levels were measured 24 hours after treatment. The codon 12-directed compound was effective in the cell line expressing mutant Ki-ras. However, as shown in FIG. 21, the Ki-ras oligonucleotide targeted to the 5'-untranslated region was a potent inhibitor of Ki-ras expression in both cell lines. Selectivity for mutant Ki-ras was found to be dependent on oligonucleotide concentration and affinity for the RNA target.

Ki-ras oligonucleotides with deoxy gaps: Phosphorothioate oligonucleotides (SEQ ID NO: 21, targeted to the 5'-untranslated region of Ki-ras) were synthesized with 2'-O-methyl modifications flanking central 2'-deoxy gap regions of 6 or 8 nucleotides in length. Both gapped oligonucleotides were active against Ki-ras expression as determined by Northern blot analysis. A uniformly 2'-O-methylated compound (no deoxy gap) was inactive. An additional oligonucleotide, ISIS 7679 (SEQ ID NO: 33, complementary to the 5' untranslated/AUG region of Ki-ras), was also found to be active when synthesized with a 6- or 8- nucleotide deoxy gap.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed, however the actual synthesis of the oligonucleotides are well within the talents of the routineer. It is also well known to use similar techniques to prepare other oligonucleotides such as the phosphorothioates and alkylated derivatives.

The oligonucleotides of this invention are designed to be complementary to, and thus hybridizable with, messenger RNA derived from the H-ras gene. Such hybridization, when accomplished, interferes with the normal roles of the messenger RNA to cause a loss of its function in the cell. The functions of messenger RNA to be interfered with include all vital functions such as translocation of the RNA to the site for protein translation, actual translation of protein from the RNA, splicing of the RNA to yield one or more mRNA species, and possibly even independent catalytic activity which may be engaged in by the RNA. The overall effect of such interference with the RNA function is to interfere with expression of the H-ras gene. Some oligonucleotides of this invention are designed to activate RNAse H cleavage of the ras mRNA.

The protein products of the other mammalian ras genes, N-ras and K-ras, are identical to H-ras over the first 85 amino acids. The nucleic acid sequences of the three ras genes, while not identical, are known, and persons of ordinary skill in the art will be able to use this invention as a guide in preparing oligonucleotides specifically hybridizable with the N-ras and K-ras genes. While the preferred embodiments of this invention relate to antisense oligonucleotides specifically hybridizable with codon 12 of the H-ras mRNA, this invention can be used by persons skilled in the art as a guide in preparing oligonucleotides specifically hybridizable with other point mutations of the ras gene, particularly the well defined point mutations at codon 12, codon 13 and codon 61 of H-ras, N-ras and K-ras, the sequences of which are known.

FIG. 22 illustrates the chemical structural aspects of certain preferred chimeric oligonucleotides of the invention. The left hand structure illustrates an oligonucleotide having certain heteroatom linkage abbreviated as MMI linkages connecting each of the sugar-nucleosidic base units together. Specific methods for preparing these MMI linkages are taught in U.S. Pat. Nos. 5,378,825, that issued on Jan. 3, 1995; 5,386,023, that issued on Jan. 31, 1995; 5,489,243, that issued on Feb. 6, 1996; 5,541,307, that issued on Jul. 30, 1996; 5,618,704, issued Apr. 8, 1997; and 5,623,070, issued Apr. 22, 1997; each of which is incorporate herein by reference. MMI is an abbreviation for methylene (methylimino) that in turn is a shorten version of the more complex chemical nomenclature "3'-de(oxyphosphinico)-3'[methylene(methylimino)]." Irrespective of chemical nomenclature, the linkages are as described in these patents. The linkages of these patents have also been described in various scientific publications by the inventors and their co-authors including Bhat et al., *J. Org. Chem.*, 1996, 61, 8186–8199, and the various references cited therein.

Illustrated in the center of FIG. 22 are certain oligonucleotides that have staggered or alternating linkages. These are formed from alternating MMI and phosphodiester or phosphorothioate linkages. Illustrated on the right hand side of FIG. 22 are oligonucleotides that have chimeric structures formed by a region of phosphorothioate linkages in a central "gap" flanked by the mixed or alternating, i.e. staggered, linkages of the center of the figure.

In the MMI containing oligonucleotides of FIG. 22, except for those in the "gap" region on the left hand side of the figure, the remainder of the nucleoside units of the "flank" regions of the various oligonucleotides are illustrated as a 2'-O-methyl nucleoside units, i.e. 2'-OMe nucleosides. Other 2'-substituted nucleoside units for inclusion in the oligonucleotides of the invention include 2'-fluoro, 2'-O-alkyl and 2'-O-substituted alkyl nucleosides. A preferred substituent is an alkoxy subsituents, i.e. an ethers. Most preferred is are 2'-O-methoxyethyl substituted nucleosides, see Martin, P., *Helvetica Chimica Acta,* 1995, 78, 486–504.

Various oligonucleotides of SEQ ID NO. 2 having specific chemical structures as illustrated in FIG. 22 were tested for their ability to inhibit production of H-ras mRNA in T-24 cells. For these test, T-24 cells were plated in 6-well plates and then treated with various escalating concentrations of oligonucleotide in the presence of cationic lipid (Lipofectin, GIBCO) at the ration of 2.5 µg/ml Lipofectin per 100 nM oligonucleotide. Oligonucleotide treatment was carried out in serum free media for 4 hours. Eighteen hours after treatment the total RNA was harvested and analyzed by northern blot for H-ras mRNA and control gene G3PDH. The structures of the oligonucleotides and the test data are shown in FIGS. 23 and 24. The data is presented in the bar graphs as percent control normalized for the G3PDH signal. As is seen in the FIGS. 23 and 24, oligonucleotides of the inventions each exhibited a dose responses across the range of doses. The chimeric oligonucleotides that incorporated the MMI nucleoside units had responses equivalent to or better than the phosphorothioate oligonucleotide used as the positive control for these tests with oligonucleotides having 1 or 2 MMI linkages (oligos 14896, 14897 and 14898) in each of the flank regions showing the greatest reduction of H-ras mRNA. The oligo having 3 MMI linkages alternating with phosphorothioate linkages (oligo 14900) was essential equal potent with that of the positive control while the oligo having 3 MMI linkages alternating with phosphodiester linkages (oligo 14899) showed lower potency than that of the positive control. Of equal potency with the positive control was the oligonucleotide (oligo 13920) having 2'-O-methoxyethyl substituents in its flanking regions.

The oligonucleotides of this invention can be used in diagnostics, therapeutics and as research reagents and kits. Since the oligonucleotides of this invention hybridize to the ras gene, sandwich and other assays can easily be constructed to exploit this fact. Furthermore, since the oligonucleotides of this invention hybridize preferentially to the mutant (activated) form of the ras oncogene, such assays can be devised for screening of cells and tissues for ras conversion from wild-type to activated form. Such assays can be utilized for differential diagnosis of morphologically similar tumors, and for detection of increased risk of cancer stemming from ras gene activation. Provision of means for detecting hybridization of oligonucleotide with the ras gene can routinely be accomplished. Such provision may include enzyme conjugation, radiolabelling or any other suitable detection systems. Kits for detecting the presence or absence of ras or activated ras may also be prepared.

The following examples illustrate the present invention and are not intended to limit the same.

EXAMPLES

Example 1

Oligonucleotide Synthesis

Substituted and unsubstituted deoxyoligonucleotides were synthesized on an automated DNA synthesizer (Applied Biosystems model 380B) using standard phosphoramidate chemistry with oxidation by iodine. For phosphorothioate oligonucleotides, the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 hr), the oligonucleotides were purified by precipitation twice out of 0.5 M NaCl solution with 2.5 volumes ethanol. Analytical gel electrophoresis was accomplished in 20% acrylamide, 8 M urea, 454 mM Tris-borate buffer, pH=7.0. Oligonucleotides were judged from polyacrylamide gel electrophoresis to be greater than 80% full-length material.

Oligoribonucleotides were synthesized using the automated synthesizer and 5'-dimethoxy-trityl 2'-tertbutyldimethylsilyl 3'-O-phosphoramidites (American Bionetics, Hayward, Calif.). The protecting group on the exocyclic amines of A,C and G was phenoxyacetyl [Wu, T., Oglivie, K. K., and Pon, R. T., *Nucl. Acids Res.* 1989, 17, 3501–3517]. The standard synthesis cycle was modified by increasing the wait step after the pulse delivery of tetrazole to 900 seconds. Oligonucleotides were deprotected by overnight incubation at room temperature in methanolic ammonia. After drying in vacuo, the 2'-silyl group was removed by overnight incubation at room temperature in 1 M tetrabutylammoniumfluoride (Aldrich; Milwaukee, Wis.) in tetrahydrofuran. Oligonucleotides were purified using a C-18 Sep-Pak cartridge (Waters; Milford, Mass.) followed by ethanol precipitation. Analytical denaturing polyacrylamide electrophoresis demonstrated the RNA oligonucleotides were greater than 90% full length material.

Example 2 ras-Luciferase Reporter Gene Assembly

The ras-luciferase reporter genes described in this study were assembled using PCR technology. Oligonucleotide primers were synthesized for use as primers for PCR cloning of the 5'-regions of exon 1 of both the mutant (codon 12) and non-mutant (wild-type) human H-ras genes. The plasmids pT24-C3, containing the c-H-ras1 activated oncogene (codon 12, GGC→GTC), and pbc-N1, containing the c-H-ras proto-oncogene, were obtained from the American Type Culture Collection (Bethesda, Md.). The plasmid pT3/T7 luc, containing the 1.9 kb firefly luciferase gene, was obtained from Clontech Laboratories (Palo Alto, Calif.). The oligonucleotide PCR primers were used in standard PCR reactions using mutant and non-mutant H-ras genes as templates. These primers produce a DNA product of 145 base pairs corresponding to sequences −53 to +65 (relative to the translational initiation site) of normal and mutant H-ras, flanked by NheI and HindIII restriction endonuclease sites. The PCR product was gel purified, precipitated, washed and resuspended in water using standard procedures.

PCR primers for the cloning of the *P. pyralis* (firefly) luciferase gene were designed such that the PCR product would code for the full-length luciferase protein with the exception of the amino-terminal methionine residue, which would be replaced with two amino acids, an amino-terminal lysine residue followed by a leucine residue. The oligonucleotide PCR primers used for the cloning of the luciferase gene were used in standard PCR reactions using a commercially available plasmid (pT3/T7-Luc) (Clontech), containing the luciferase reporter gene, as a template. These primers yield a product of approximately 1.9 kb corresponding to the luciferase gene, flanked by unique HindIII and BssHII restriction endonuclease sites. This fragment was gel purified, precipitated, washed and resuspended in water using standard procedures.

To complete the assembly of the ras-luciferase fusion reporter gene, the ras and luciferase PCR products were digested with the appropriate restriction endonucleases and cloned by three-part ligation into an expression vector containing the steroid-inducible mouse mammary tumor virus promotor MMTV using the restriction endonucleases NheI, HindIII and BssHII. The resulting clone results in the insertion of H-ras 5' sequences (−53 to +65) fused in frame with the firefly luciferase gene. The resulting expression vector encodes a ras-luciferase fusion product which is expressed under control of the steroid-inducible MMTV promoter. These plasmid constructions contain sequences encoding amino acids 1–22 of activated (RA2) or normal (RA4) H-ras proteins fused in frame with sequences coding for firefly luciferase. Translation initiation of the ras-luciferase fusion mRNA is dependent upon the natural H-ras AUG codon. Both mutant and normal H-ras luciferase fusion constructions were confirmed by DNA sequence analysis using standard procedures.

Example 3

Transfection of Cells with Plasmid DNA

Transfections were performed as described by Greenberg, M. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, NY, with the following modifications. HeLa cells were plated on 60 mm dishes at $5\times10^5$ cells/dish. A total of 10 μg or 12 μg of DNA was added to each dish, of which 1 μg was a vector expressing the rat glucocorticoid receptor under control of the constitutive Rous sarcoma virus (RSV) promoter and the remainder was ras-luciferase reporter plasmid. Calcium phosphate-DNA coprecipitates were removed after 16–20 hours by washing with Tris-buffered saline [50 Mm Tris-Cl (pH 7.5), 150 mM NaCl] containing 3 mM EGTA. Fresh medium supplemented with 10% fetal bovine serum was then added to the cells. At this time, cells were pretreated with antisense oligonucleotides prior to activation of reporter gene expression by dexamethasone.

Example 4

Oligonucleotide Treatment of Cells

Following plasmid transfection, cells were washed with phosphate buffered saline prewarmed to 37° C. and Opti-MEM containing 5 μg/mL N-[1-(2,3-dioleyloxy)propyl]-N, N,N,-trimethylammonium chloride (DOTMA) was added to each plate (1.0 ml per well). oligonucleotides were added from 50 μM stocks to each plate and incubated for 4 hours at 37° C. Medium was removed and replaced with DMEM containing 10% fetal bovine serum and the appropriate oligonucleotide at the indicated concentrations and cells were incubated for an additional 2 hours at 37° C. before reporter gene expression was activated by treatment of cells with dexamethasone to a final concentration of 0.2 μM. Cells were harvested and assayed for luciferase activity fifteen hours following dexamethasone stimulation.

Example 5

Luciferase Assays

Luciferase was extracted from cells by lysis with the detergent Triton X-100 as described by Greenberg, M. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, NY. A Dynatech ML1000 luminometer was used to measure peak luminescence upon addition of luciferin (Sigma) to 625 μM. For each extract, luciferase assays were performed multiple times, using differing amounts of extract to ensure that the data were gathered in the linear range of the assay.

Example 6

Melting Curves

Absorbance vs temperature curves were measured at 260 nm using a Gilford 260 spectrophotometer interfaced to an IBM PC computer and a Gilford Response II spectrophotometer. The buffer contained 100 mM Na$^+$, 10 mM phosphate and 0.1 mM EDTA, pH 7. Oligonucleotide concentration was 4 µM each strand determined from the absorbance at 85° C. and extinction coefficients calculated according to Puglisi and Tinoco, *Methods in Enzymol.* 1989, 180, 304–325. $T_m$ values, free energies of duplex formation and association constants were obtained from fits of data to a two state model with linear sloping baselines. Petersheim, M. and Turner, D. H., *Biochemistry* 1983, 22, 256–263. Reported parameters are averages of at least three experiments. For some oligonucleotides, free energies of duplex formation were also obtained from plots of $T_m^{-1}$ vs $\log_{10}$ (concentration). Borer, P. N., Dengler, B., Tinoco, I., Jr., and Uhlenbeck, O. C., *J. Mol. Biol.,* 1974, 86, 843–853.

Example 7

Gel Shift Assay

The structured ras target transcript, a 47-nucleotide hairpin containing the mutated codon 12, was prepared and mapped as described in Lima et al., *Biochemistry* 1991, 31, 12055–12061. Hybridization reactions were prepared in 20 µl containing 100 mM sodium, 10 mM phosphate, 0.1 mM EDTA, 100 CPM of T7-generated RNA (approximately 10 pM), and antisense oligonucleotide ranging in concentration from 1 pM to 10 µM. Reactions were incubated 24 hours at 37° C. Following hybridization, loading buffer was added to the reactions and reaction products were resolved on 20% native polyacrylamide gels, prepared using 45 mM trisborate and 1 mM MgCl$_2$ (TBM). Electrophoresis was carried out at 10° C. and gels were quantitated using a Molecular Dynamics Phosphorimager.

Example 8

RNase H Analysis

RNase H assays were performed using a chemically synthesized 25-base oligoribonucleotide corresponding to bases +23 to +47 of activated (codon 12, G→U) H-ras mRNA. The 5' end-labeled RNA was used at a concentration of 20 nM and incubated with a 10-fold molar excess of antisense oligonucleotide in a reaction containing 20 mM tris-Cl, pH 7.5, 100 mM KCl, 10 mM MgCl$_2$, 1 mM dithiothreitol, 10 µg tRNA and 4 U RNasin in a final volume of 10 µl. The reaction components were preannealed at 37° C. for 15 minutes then allowed to cool slowly to room temperature. HeLa cell nuclear extracts were used as a source of mammalian RNase H. Reactions were initiated by addition of 2 µg of nuclear extract (5 µl) and reactions were allowed to proceed for 10 minutes at 37° C. Reactions were stopped by phenol/chloroform extraction and RNA components were precipitated with ethanol. Equal CPMs were loaded on a 20% polyacrylamide gel containing 7M urea and RNA cleavage products were resolved and visualized by electrophoresis followed by autoradiography. Quantitation of cleavage products was performed using a Molecular Dynamics Densitometer.

Example 9 ras Transactivation Reporter Gene System

The expression plasmid pSV2-oli, containing an activated (codon 12, GGC→GTC) H-ras cDNA insert under control of the constitutive SV40 promoter, was a gift from Dr. Bruno Tocque (Rhone-Poulenc Sante, Vitry, France). This plasmid was used as a template to construct, by PCR, a H-ras expression plasmid under regulation of the steroid-inducible mouse mammary tumor virus (MMTV) promoter. To obtain H-ras coding sequences, the 570 bp coding region of the H-ras gene was amplified by PCR. The PCR primers were designed with unique restriction endonuclease sites in their 5'-regions to facilitate cloning. The PCR product containing the coding region of the H-ras codon 12 mutant oncogene was gel purified, digested, and gel purified once again prior to cloning. This construction was completed by cloning the insert into the expression plasmid pMAMneo (Clontech Laboratories, CA).

The ras-responsive reporter gene pRDO53 was used to detect ras expression. Owen et al., *Proc. Natl. Acad. Sci. U.S.A.* 1990, 87, 3866–3870.

Example 10

Northern Blot Analysis of ras Expression in Vivo

The human urinary bladder cancer cell line T24 was obtained from the American Type Culture Collection (Rockville Md.). Cells were grown in McCoy's 5A medium with L-glutamine (Gibco BRL, Gaithersburg Md.), supplemented with 10% heat-inactivated fetal calf serum and 50 U/ml each of penicillin and streptomycin. Cells were seeded on 100 mm plates. When they reached 70% confluency, they were treated with oligonucleotide. Plates were washed with 10 ml prewarmed PBS and 5 ml of Opti-MEM reduced-serum medium containing 2.5 µl DOTMA. Oligonucleotide was then added to the desired concentration. After 4 hours of treatment, the medium was replaced with McCoy's medium. Cells were harvested 48 hours after oligonucleotide treatment and RNA was isolated using a standard CsCl purification method. Kingston, R. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, NY.

The human epithelioid carcinoma cell line HeLa 229 was obtained from the American Type Culture Collection (Bethesda, Md.). HeLa cells were maintained as monolayers on 6-well plates in Dulbecco's Modified Eagle's medium (DMEM) supplemented with 10% fetal bovine serum and 100 U/ml penicillin. Treatment with oligonucleotide and isolation of RNA were essentially as described above for T24 cells.

Northern hybridization: 10 µg of each RNA was electrophoresed on a 1.2% agarose/formaldehyde gel and transferred overnight to GeneBind 45 nylon membrane (Pharmacia LKB, Piscataway, N.J.) using standard methods. Kingston, R. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, NY. RNA was UV-crosslinked to the membrane. Double-stranded $^{32}$P-labeled probes were synthesized using the Prime a Gene labeling kit (Promega, Madison, Wis.). The ras probe was a SalI-NheI fragment of a cDNA clone of the activated (mutant) H-ras mRNA having a GGC-to-GTC mutation at codon-12. The control probe was G3PDH. Blots were prehybridized for 15 minutes at 68° C. with the QuickHyb hybridization solution (Stratagene, La Jolla, Calif.). The heat-denatured radioactive probe (2.5×10$^6$ counts/2 ml hybridization solution) mixed with 100 µl of 10 mg/ml salmon sperm DNA was added and the membrane was hybridized for 1 hour at 68° C. The blots were washed twice for 15 minutes at room temperature in 2x SSC/0.1% SDS and once for 30 minutes at 60° C. with 0.1X SSC/0.1% SDS. Blots were autoradiographed and the intensity of signal was quantitated using an ImageQuant PhosphorImager (Molecular Dynamics, Sunnyvale, Calif.). Northern blots were first hybridized with the ras probe, then stripped by boiling for 15 minutes in 0.1x SSC/0.1% SDS and rehybridized with the control G3PDH probe to check for correct sample loading.

Example 11

Antisense Oligonucleotide Inhibition of Proliferation of Cancer Cells

Cells were cultured and treated with oligonucleotide essentially as described in Example 10. Cells were seeded on 60 mm plates and were treated with oligonucleotide in the presence of DOTMA when they reached 70% confluency. Time course experiment: On day 1, cells were treated with a single dose of oligonucleotide at a final concentration of 100 nM. The growth medium was changed once on day 3 and cells were counted every day for 5 days, using a counting chamber. Dose-response experiment: Various concentrations of oligonucleotide (10, 25, 50, 100 or 250 nM) were added to the cells and cells were harvested and counted 3 days later. Oligonucleotides 2570, 3985 and 4690 were tested for effects on T24 cancer cell proliferation.

Example 12

Synthesis of 2-(Amino)Adenine-Substituted Oligonucleotides

Oligonucleotides are synthesized as in Example 1, with the following exception: at positions at which a 2-(amino) adenine is desired, the standard phosphoramidite is replaced with a commercially available 2-aminodeoxyadenosine phosphoramidite (Chemgenes).

Example 13

Culture of A549 Cells

A549 cells (obtained from the American Type Culture Collection, Bethesda, Md.) were grown to confluence in 6-well plates (Falcon Labware, Lincoln Park, N.J.) in Dulbecco's modified Eagle's medium (DME) containing 1 g glucose/liter and 10% fetal calf serum (FCS, Irvine Scientific, Santa Ana, Calif.).

Example 14

Oligonucleotide Treatment of Human Tumor Cells in Nude Mice—Intraperitoneal Injection Human lung carcinoma A549 cells were harvested and $5 \times 10^6$ cells (200 µl) were injected subcutaneously into the inner thigh of nude mice. Palpable tumors develop in approximately one month. Phosphorothioate oligonucleotides ISIS 2503 and 1082 (unrelated control) were administered to mice intraperitoneally at a dosage of 20 mg/kg body weight, every other day for approximately ten weeks. Mice were monitored for tumor growth during this time.

Example 15

Oligonucleotide Treatment of Human Tumor Cells in Nude Mice—Subcutaneous Injection with Cationic Lipid Human lung carcinoma A549 cells were harvested and $5 \times 10^6$ cells (200 µl) were injected subcutaneously into the inner thigh of nude mice. Palpable tumors develop in approximately one month. Phosphorothioate oligonucleotides ISIS 2503 and the unrelated control oligonucleotide 1082 (dosage 5 mg/kg), prepared in a cationic lipid formulation (DMRIE/DOPE, 60 mg/kg) were administered to mice subcutaneously at the tumor site. Drug treatment began one week following tumor cell inoculation and was given twice a week for only four weeks. Mice were monitored for tumor growth for a total of nine weeks.

Example 16

Stability of 2' Modified Oligonucleotides in T24 Cells

T24 bladder cancer cells were grown as described in Example 10. Cells were treated with a single dose (1 µM) of oligonucleotide and assayed for Ha-ras mRNA expression by Northern blot analysis 24 hours later. Oligonucleotides tested were analogs of ISIS 2570 (SEQ ID NO: 3), a 17 mer targeted to Ha-ras codon 12.

Example 17

Activity of Ki-ras Oligonucleotides Against Three Colon Carcinoma Cell Lines Human colon carcinoma cell lines Calu 1, SW480 and SW620 were obtained from the American Type Culture Collection (ATCC) and cultured and maintained as described for HeLa cells in Example 10. Cells were treated with a single dose of oligonucleotide (200 mM) and Ki-ras mRNA expression was measured by Northern blot analysis 24 hours later. For proliferation studies, cells were treated with a single dose of oligonucleotide (200 nM) at day zero and cell number was monitored over a five-day period.

Example 18

Oligonucleotide Inhibition of Mutant vs. Wild-Type Ki-ras

SW480 cells were cultured as in the previous example. HeLa cells were cultured as in Example 10. Cells were treated with a single dose (100 nM) of oligonucleotide and mRNA levels were determined by Northern blot analysis 24 hours later.

Examples 19–35

General Information

Unless otherwise noted, materials were obtained from commercial suppliers and were used as provided. 2'-O-Methyl-5-methyluridine, 5'-O-(4,4'-dimethoxytriphenylmethyl)-2'-O-methyl-5-methyluridine, 5'-O-(4,4'-dimethoxytriphenylmethyl)-N-2-isobutyryl-2'-O-methylguanosine, and N-6-benzoyl-5'-O-(4,4'-dimethoxytriphenylmethyl)-2'-O-methyladenosine were purchased from RI Chemicals, CA (714-288-1548). 2'-O-Methylguanosine and 2'-O-methyladenosine were purchased from Summit Pharmaceuticals Corp., N. J. (201-585-9687).

NMR Spectroscopy. $^1$H NMR spectra for all compounds were recorded either at 399.94 MHz on a Varian Unity 400 NMR spectrometer or at 199.975 MHz on a Varian Gemini 200 NMR spectrometer. All multi-dimensional and variable temperature spectra were collected on the Unity 400 NMR. The compound 19d was studied at a concentration of 1.6 mM in 600 µl DMSO-$d_6$. One-dimensional $^1$H NMR spectra were recorded at the sample temperatures 293, 310, 333, and 353 K. All one-dimensional measurements were performed under the same conditions and processed identically: 5200 Hz sweep width, 32K time domain, zero-filling to 64K. Where possible, the data were studied unapodized, but in some instances the standard Varian VnmrS resolution enhancement method was invoked, using a line broadening of −1.01 and a gaussian filter of 0.945. All subspectra were observed to be first order. Proton resonances were assigned from two-dimensional spectra run at 310 and 353 K. TOCSY and NOESY spectra were run at 310 K with a 20 ms spin-lock and a 650 ms mixing time, respectively, with 1k by 512 complex points being collected in a phase-sensitive manner. Similar experiments were carried out at 353 K, with 2 k by 512 complex points collected in a phase-sensitive manner. In each case, the data was apodized with a squared cosine and zero-filled to 2 k×1 k complex points before fourier transformation. The $^{13}$C spectra were recorded on the same instrument, at a frequency of 100.57 MHz, using a sweep width of 30441 Hz, an acquisition time of 0.50 s, and processed by apodizing with 2 Hz line-broadening and zero-filling to 32K. The $^{13}$C spectrum was assigned with the aid of a $^{1}$H{$^{13}$C} HMQC at 293 K. For this experiment 1K complex points were collected in the directly-detected dimension over a sweep width of 3200 Hz. A total of 240 increments were collected in a phase-sensitive manner in the indirectly-detected dimension, over a sweep-width of 22 kHz. The data was apodized with a squared cosine in the $^{1}$H dimension and a gaussian in $t_1$.

One-dimensional $^{1}$H spectra for 12h, 12i, 12j, 18a, 20a, and 20b were all recorded at 293 K using identical parameters for acquisition and processing: 14336 complex points were collected over a sweep width of 7 kHz. Data was zero-filled to 64K points and apodized with 0.30 Hz line-broadening before fourier transform. Two-dimensional spectra were acquired with sweep widths adjusted to optimize resolution across the spectral range of each sample, ranging from 4 kHz to 5200 Hz in each dimension. Data sets of 1K by 256 points were acquired for 12h and 12j, 1K by 512 points for 12i and 20b. Data sets of 2K by 512 data points were collected for 18 and 20b to allow adequate resolution. Data was collected at 313 K for 20a and 20b to enhance chemical shift dispersion. All data was phase-sensitive, processed under conditions otherwise identical to the methods used in the TOCSY and NOESY work outlined above. $^{1}$H NMR data for 19b was collected at 310 K in deuterium oxide, using the same series of experiments described above. Other general experimental procedures were carried out as described previoulsy in Perbost, M.; Hoshiko, T.; Morvan, F.; Swayze, E.; Griffey, R. H.; Sanghvi, Y. S., *J. Org. Chem.* 1995, 60, 5150–5156.

Example 19

General Procedure A, Synthesis of 3'-iodo-2'-O-methyl Nucleosides (11→12)

To a solution of pyridine (4.3 eq) in dry $CH_2Cl_2$ (5 mL/mmol) at −10° C. under an inert atmosphere is added a solution of trifluoromethanesulfonic anhydride (2 eq) in $CH_2Cl_2$ (5 mL/mmol) dropwise over 0.5 h. After stirring an additional 0.25 h, a solution of appropriately protected 3'-hydroxyl nucleoside (1 eq, azeotroped with dry pyridine) in dry $CH_2Cl_2$ (5 mL/mmol) was added dropwise over 0.5 h, and the solution stirred at −10° C. for an additional 2 h. The reaction mixture was diluted with an equal volume of ice cold 10% aqueous $NaHCO_3$ with vigorous stirring, and the mixture was allowed to warm to rt. The organic phase was removed, dried ($MgSO_4$), diluted with toluene (5 mL/mmol), concentrated, and azeotroped with dry toluene (3×5 mL/mmol). To the resulting foam was added $Bu_4NI$ (2 eq) and dry toluene (30 mL/mmol), and the resulting mixture heated for 0.5 h at 80° C. in an oil bath with vigorous stirring, at which point all solid had dissolved, and a dark red oil separated. The resulting mixture was dissolved by dilution with EtOAc, then washed with water (15 mL/mmol), 1:1 5% aqueous $NaHSO_3$ and 5% aqueous $Na_2SO_3$ (2×15 mL/mmol), dried ($MgSO_4$), concentrated, and chromatographed to provide the iodide.

Example 20

3'-Deoxy-5'-O-(4,4'-dimethoxytriphenylmethyl)-3'-iodo-2'-O-methyl-5-methyluridine (12a)

From 5'-O-(4,4'-dimethoxytrityl)-2'-O-methyl-5-methyluridine (5.75 g, 10 mmol) according to general procedure A was obtained 4.41 g (64%) of 12a after chromatography (30% to 50% EtOAc/hexane): $R_f$ 0.38 (50% EtOAc/hexane); $^{1}$H NMR (CDCl$_3$) δ 9.91 (s, 1H), 7.55–7.20 (m, 10H), 6.85 (d, 4H), 5.85 (s, 1H, H-1'), 4.37 (s, 1H), 4.31 (d, 1H), 3.93 (m, 1H), 3.79 (s, 6H), 3.60–3.50 (m, 1H), 3.56 (s, 3H), 3.20 (m, 1H), 1.83 (s, 3H); $^{13}$C NMR (CDCl$_3$) δ 164.16, 158.53, 150.35, 144.23, 136.14, 135.44, 135.25, 130.06, 128.12, 127.77, 126.88, 113.06, 110.06, 92.48, 90.17, 86.55, 80.00, 68.56, 58.32, 55.09, 26.84, 12.32. Anal. Calcd for $C_{32}H_{33}N_2O_7I.0.4\ CH_2Cl_2$: C, 54.16; H, 4.74; N, 3.90. Found: C, 54.27; H, 4.58; N, 3.73.

Example 21

3'-Deoxy-5'-O-(4,4'-dimethoxytriphenylmethyl)-3'-iodo-2-N-isobutyryl-2'-O-methylguanosine (12c)

From 5 g (8.26 mmol) of 11c according to general procedure A was obtained 3.8 g (59%) of 12b after chromatography (80% EtOAc/hexane): $^{1}$H NMR (DMSO-d$_6$) δ 12.14 (s, 1H), 11.67 (s, 1H), 7.96 (s, 1H), 7.42–7.20 (m, 9H), 7.17–6.86 (m, 4H), 5.85 (d, J=2.1 Hz, 1H), 4.74 (bs, 2H), 3.87–3.86 (m, 1H), 3.73 (s, 6H), 3.32–3.08 (m, 5H), 2.85–2.70 (m, 1H), 1.12–1.03 (m, 6H); MS (FAB$^+$) m/e 780 (M+H). Anal. Calcd for $C_{36}H_{38}N_5O_7I.\ 0.25\ C_6H_{14}$: C, 56.25; H, 5.16; N, 8.75. Found: C, 56.48; H, 5.24; N, 8.68.

Example 22

6-N-Benzoyl-3'-deoxy-5'-O-(4,4'-dimethoxytriphenylmethyl)-3'-iodo-2'-O-methyladenosine (12k)

From N-6-benzoyl-5'-O-(4,4'-dimethoxytrityl)-2'-O-methyladenosine (0.69 g, 1 mmol) according to general procedure A was obtained 0.47 g (58%) of 12k after chromatography (50% to 70% EtOAc/hexane): $R_f$ 0.34 (50% EtOAc/hexane); $^{1}$H NMR (CDCl$_3$) δ 9.12 (s, 1H), 8.81 (s, 1H), 8.37 (s, 1H), 8.03 (d, 2H), 7.65–7.15 (m, 9H), 6.85 (d, 4H), 6.18 (s, 1H, H-1'), 4.68 (s, 1H), 4.39 (d, 1H), 3.94 (dd, 1H), 3.80 (s, 6H), 3.66 (dd, 1H), 3.63 (s, 3H), 3.21 (dd, 1H); $^{13}$C NMR (CDCl$_3$) δ 164.52, 158.61, 158.57, 152.71, 151.09, 149.37, 144.36, 141.46, 135.64, 135.35, 133.61, 132.72, 130.10, 130.03, 128.81, 128.10, 127.86, 127.79, 126.96, 123.38, 113.16, 92.76, 89.73, 86.61, 80.48, 68.58, 58.38, 55.20, 26.60. Anal. Calcd for $C_{39}H_{36}N_6O_6I.0.4\ CH_2Cl_2.0.5\ EtOAc$: C, 56.79; H, 4.70; N, 8.00. Found: C, 56.60; H, 4.64; N, 8.01.

Example 23

5'-O-(tert-Butyldiphenylsilyl)-3'-deoxy-3'-iodo-5-methyl-2'-O-methyluridine (12e)

A solution of 11e (7.0 g, 13.7 mmol) and dry pyridine (1.9 g, 24.6 mmol) in anhydrous $CH_2Cl_2$ (80 mL) was cooled under vigorous stirring to −10° C. in an inert atmosphere for about 20 min. A solution of triflic anhydride (5.1 g, 17.7 mmol) in $CH_2Cl_2$ (30 mL) was slowly added via a syringe (15 min.). The reaction was complete in 35 min. after the addition. To this cold solution was added MeOH (1 mL) and then saturated $NaHCO_3$ and the organic layer was separated and washed with brine (2×15 mL) followed by drying over $Na_2SO_4$. Solvent was removed under reduced pressure and the residue azeotroped with toluene (2×20 mL). The residual gum was dissolved in p-xylene (100 mL) and to this was added $Bu_4NI$ (5.6 g,15.1 mmol), and the reaction mixture heated at 140° C. in a preheated bath. The reaction was complete in 30 min. It was cooled to rt, then diluted with EtOAc (250 mL), and washed with 5% aqueous solution of sodium sulfite and sodium bisulfite (1:1). The organic layer was dried over $Na_2SO_4$ and concentrated followed by flash chromatography on silica gel using 60% EtOAc/hexane. Removal of the solvent furnished 6.8 g (80%) of 12e as a colorless foam: $^1H$ NMR (DMSO-$d_6$) δ 11.50 (s, 1H), 7.23–7.43 (m, 11H), 5.78 (d, J=4.0 Hz, 1H), 4.6 (bs,1H), 4.40–4.43 (m, 1H), 3.89 (bs, 2H), 3.42 (s, 3H), 1.59 (s, 3H), 1.04 (s, 9H); MS (FAB$^+$) m/e 621 (M+H). Anal. Calcd for $C_{27}H_{33}N_2O_5SiI$: C,52.26; H, 5.36; N, 4.51. Found: C, 52.55; H, 5.41; N, 4.48.

Example 24

5'-O-(tert-Butyldiphenylsilyl)-3'-deoxy-6-N-(dimethylamino)methylene-3'-iodo-2'-O-methyladenosine (12f)

From 11h (5.3 g, 9.2 mmol), pyridine (3.65 g, 46.1 mmol), triflic anhydride (3.0 g, 11 mmol) and $Bu_4NI$ (5.2 g, 14.0 mmol) according to the method used for 12e was obtained 3.8 g (60%) of 12f after chromatography on silica gel using 80:15:3–5% MeOH in EtOAc:hexane: $^1H$ NMR (DMSO-$d_6$) δ 8.93 (s, 1H), 8.45 (s, 1H), 8.24 (s, 1H), 7.73–7.39 (m, 10H), 6.07 (d, J=2.8 Hz, 1H), 4.89–4.87 (m, 1H), 4.76–4.74 (m, 1H), 3.98–3.93 (m, 3H), 3.46 (s, 3H), 3.21 (s, 3H), 3.14 (s, 3H), 1.03 (s, 9H); MS (FAB$^+$) m/e 685 (M+H). Anal. Calcd for $C_{30}H_{37}N_6O_3SiI$. 0.25 $C_6H_{12}$: C, 53.61; H, 5.71; N, 11.91. Found: C, 53.20; H, 5.58; N, 12.24.

Example 25

5'-O-(tert-Butyldiphenylsilyl)-3'-deoxy-2-N-(dimethylamino)methylene-3'-iodo-2'-O-methylguanosine (12g)

From 11j (5.0 g, 8.46 mmol), pyridine (3.36 g, 46 mmol), triflic anhydride (3 g, 11 mmol) and $Bu_4NI$ (5.2 g, 14.0 mmol) according to the method used for 12e was obtained 2.5 g (43%) of 12g after chromatography on silica gel using 80:15:3–5% MeOH in EtOAc:hexane: $^1HNMR$ (DMSO-$d_6$) δ 11.43 (s, 1H), 8.58 (s, 1H), 7.87 (s, 1H), 7.70–7.64 (m, 10H), 5.90 (d, J=2 Hz, 1H), 4.88 (bs, 1H), 4.70 (bs, 1H), 3.46 (s, 3H), 3.12 (s, 3H), 3.04 (s, 3H), 1.02 (s, 9H); MS (FAB$^+$) m/e 701 (M+H). Anal. Calcd for $C_{30}H_{37}N_6O_4SiI$: C, 51.43; H, 5.32; N, 11.99. Found: C, 51.56; H, 5.37; N, 11.98.

Example 26

General Procedure B, Mitsunobu Reaction of Nucleosides (10–13)

A mixture of the appropriate nucleoside (1 eq.), triphenylphosphine (1.15 eq.) and N-hydroxyphthalimide (1.15 eq.) was dried under vacuum over $P_2O_5$ for 18 h prior to use. To this mixture under an inert atmosphere is added dry THF (for T) or DMF (for A and $G^{dmf}$) (10 mL/mmol), then diethylazodicarboxylate (1.15 eq.) dropwise with stirring to the solution at rt. The rate of addition is maintained such that the resulting deep red coloration is just discharged before addition of the next drop. After the addition is complete (5–45 min., depending on starting nucleoside and scale), the reaction is stirred until shown to be complete by TLC. The solvent was evaporated in vacuo to approximately ⅓ the starting volume, and if a solid was obtained (T, $G^{dmf}$) it was collected, otherwise (A) the resulting solution was partitioned between water and ether, the resulting solid collected, washed well with ether, and dried to yield the desired product. This material was pure in some cases, but usually contained traces of triphenylphosphine oxide and/or diethyl hydrazinedicarboxylate, which could be removed by column chromatography. However, these impurities did not interfere with the subsequent reactions (general procedure C), and the crude material could therefore be carried directly to the next step.

Example 27

2'-O-Methyl-5'-O-phthalimido-5-methyluridine (13a)

2'-O-Methyl-5-methyluridine (4.08 g, 15 mmol) was reacted according to general procedure B. After the reaction was complete (by TLC), the solids were collected, washed well with ether, and dried to yield 3.06 g (49%) of pure product. The combined filtrates were concentrated, then purified by column chromatography (0 to 4% MeOH/$CH_2Cl_2$) to provide an additional 2.50 g (40%), giving a combined yield of 5.56 g (89%) of 13a: $R_f$ 0.25 (5% MeOH/$CH_2Cl_2$); $^1H$ NMR (DMSO-$d_6$) δ 11.36 (s, 1H), 7.87 (br s, 4H), 7.58 (s, 1H), 5.89 (d, J=5.7 Hz, 1H), 5.43 (d, J=5.7 Hz, 1H), 4.5–3.8 (m, 6H), 3.34 (s, 3H), 1.79 (s, 3H). Anal. Calcd for $C_{19}H_{19}N_3O_8$.0.5 $H_2O$: C, 53.52; H, 4.73; N, 9.85. Found: C, 53.51; H, 4.49; N, 9.84.

Example 28

2'-O-Methyl-5'-O-phthalimidoadenosine (13b)

From 2'-O-methyl-adenosine (50.0 g, 178 mmol) according to general procedure B was obtained 74.3 g (98%) of product after partitioning the concentrated reaction mixture between ice water (3 L) and ether (3 L), and collection and drying of the resulting solid. The product contains traces (0.125 eq by $^1H$ NMR and combustion analysis) of $Ph_3P=O$, which doesn't interfere in the silylation reaction: $R_f$ 0.38 (10% MeOH/$CH_2Cl_2$); $^1H$ NMR (DMSO-$d_6$) δ 8.36 (s, 1H), 8.12 (s, 1H), 7.81 (s, 4H), 6.02 (d, J=5.0 Hz, 1H), 5.50 (d, J=5.0 Hz, 1H), 4.6–4.3 (m, 4H), 4.3–4.2 (m, 1H), 3.33 (s, 3H); HRMS (FAB$^+$, CsI/NBA) calcd for $C_{19}H_{18}N_6O_6$+Cs$^+$ 559.0342, found 559.0355. Anal. Calcd for $C_{19}H_{18}N_6O_6$.0.125 $Ph_3P=O$ (evident in $^1H$ NMR): C, 55.34; H, 4.34; N, 18.22. Found: C, 55.07; H, 4.45; N, 17.98.

Example 29

2-N-(Dimethylamino)methylene-2'-O-methyl-5'-phthalimidoguanosine (13c)

2-N-(Dimethylamino)methylene-2'-O-methylguanosine (10f, 6.39 g, 18.2 mmol) was exhaustively dried (0.01 mm Hg, 45° C., several days over $P_2O_5$), then reacted according to general procedure B. After the reaction was complete (by TLC), it was reduced to ⅓ its original volume, and the solid was collected and dried to yield 8.85 g (93%) of hydrated 13c: $R_f$ 0.23 (10% MeOH/CH$_2$Cl$_2$);. $^1$H NMR (DMSO-d$_6$) δ 11.39 (s, 1H), 8.53 (s, 1H), 8.05 (s, 1H), 7.84 (br s, 4H), 5.92 (d, J=5.8 Hz, 1H), 5.52 (d, J=5.3 Hz, 1H), 4.5–4.1 (m, 5H), 3.14 (s, 3 H), 3.01 (s, 3H), 2.88 (s, 3 H); HRMS (FAB$^+$, CsI/NBA) calcd for C$_{22}$H$_{23}$N$_7$O$_7$+Cs$^+$ 630.0713, found 630.0725. Anal. Calcd for C$_{22}$H$_{23}$N$_7$O$_7$·1.5 H$_2$O: C, 50.38; H, 5.00; N, 18.69. Found: C, 50.57; H, 5.12; N, 18.81.

Example 30

General Procedure C, Silylation of Nucleosides (13→14)

The requisite nucleoside (1 eq, dried over P$_2$O$_5$ in vacuo) and imidazole (4.5 eq) were dissolved in dry DMF (5 mL/mmol) under an inert atmosphere, and TBDPSCl (1.5 eq) was added. The reaction was stirred at room temperature until complete by TLC (16–48 h), then poured into EtOAc (15 mL/mmol) and water (15 mL/mmol). The organic layer was washed with water (3×10 mL/mmol), dried (MgSO$_4$), and concentrated. On large scale, it proved more convenient to concentrate the crude reaction mixture to a thin syrup and partition the product between ether and water, then collect the resulting solid. This material could be purified by column chromatography, however the only impurities present were silyl by-products, which did not interfere in the subsequent conversion to the oximes via general procedure D.

Example 31

3'-tert-Butyldiphenylsilyl-2-N-(dimethylamino) methylene-2'-O-methylguanosine (14c)

From 13c (8.85 g, 16.9 mmol) according to general procedure C was obtained 10.6 g (84%) of 14c after filtration (0 to 10% MeOH/CH$_2$Cl$_2$) of the crude material through a plug of silica: $R_f$ 0.36 (10% MeOH/CH$_2$Cl$_2$);. $^1$H NMR (DMSO-d$_6$) δ 11.35 (s, 1H), 8.43 (s, 1H), 8.04 (s, 1H), 7.84 (br s, 4H), 7.5–7.7 (m, 4H), 7.3–7.4 (m, 6H), 6.02 (d, J=6.1 Hz, 1H), 4.5–4.7 (m, 1H), 4.0–4.5 (m, 4H) 3.05 (s, 3 H), 3.03 (s, 3H), 2.88 (s, 3 H), 1.06 (s, 9H); HRMS (FAB$^+$, CsI/NBA) calcd for C$_{38}$H$_{41}$N$_7$O$_7$Si+Cs$^+$ 868.1891, found 868.1899. Anal. Calcd for C$_{38}$H$_{41}$N$_7$O$_7$Si. 0.5 H$_2$O: C, 61.27; H, 5.68; N, 13.16. Found: C, 61.27; H, 5.82; N, 13.38.

Example 32

General Procedure D, Synthesis of Nucleoside 5'-Formaldoximes (14→15)

The crude material obtained from the silylation of the corresponding 5'-O-phthalimido nucleoside was dissolved in dry CH$_2$Cl$_2$ (10 mL/mmol), and methylhydrazine (1.2 eq) was added dropwise at –10 to 0° C. After 1 h, the mixture was filtered, the filtrates washed with CH$_2$Cl$_2$, and the combined organics washed with water, brine, dried (Na$_2$SO$_4$), and the solution concentrated to yield the 5'-O-amino nucleoside, which was used immediately without further purification. (The 5'-O-amino nucleosides can be purified by column chromatography, however we have observed that they tend to decompose upon standing). This residue was dissolved in 1:1 EtOAc/MeOH (15 mL/mmol), formaldehyde (20% w/w aqueous, 1.1 eq) was added, and the mixture stirred 1 h at room temperature. The solution was concentrated, then chromatographed or crystallized to provide the 3'-silyl-5'-formaldoxime.

Example 33

3'-O-tert-Butyldiphenylsilyl-2-N-(dimethylamino) methylene-2'-O-methyl-5'-O-(methyleneimino) guanosine (15e)

From 14c (10.6 g, 14.4 mmol) according to general procedure D was obtained 9.21 g of 15e in essentially quantitative yield after filtration (0 to 10% MeOH/CH$_2$Cl$_2$) of the crude material through a plug of silica: $R_f$ 0.43 (10% MeOH/CH$_2$Cl$_2$);. $^1$H NMR (DMSO-d$_6$) δ 11.19 (s, 1H), 8.47 (s, 1H), 7.94 (s, 1H), 7.5–7.7 (m, 4H), 7.4–7.5 (m, 6H), 6.96 (d, J=7.27 Hz, 1H), 6.55 (d, J=7.27 Hz, 1H), 6.02 (d, J=6.13 Hz, 1H), 4.4–4.5 (m, 1H), 4.0–4.3 (m, 4H) 3.06 (s, 3 H), 3.01 (br s, 6H), 1.06 (s, 9H) ppm. Anal. Calcd for C$_{31}$H$_{39}$N$_7$O$_5$Si. 0.5 H$_2$O: C, 59.40; H, 6.43; N, 15.64. Found: C, 59.59; H, 6.33; N, 15.61.

Example 34

General Procedure E, Radical Coupling Reaction

The appropriate 3'-deoxy-3'-iodo-nucleoside (1 eq) and 5'-formaldoxime (3 eq) were azeotroped with dry benzene (10 mL/mmol), and bis(trimethystannyl)benzopinacolate (2 eq) and dry benzene (5 mL/mmol) were added. The mixture was degassed (argon, 0.5 h), and heated to 80° C. in an oil bath for 16–24 h, at which point all iodide had been consumed (by TLC). The solution was allowed to cool, and stirred vigorously with EtOAc (50 mL/mmol) and 10% aqueous KF (20 mL/mmol) for 2 h. The organic layer was washed with 5% aqueous NaHCO$_3$ (20 mL/mmol), dried (MgSO$_4$), concentrated, dissolved in the minimum amount of CH$_2$Cl$_2$, and applied to a column of silica. Elution with 30% EtOAc/hexane (5 column volumes) provided tin by-products and benzophenone. The unreacted oxime (75–99% of unreacted material recovered), and the hydroxylamino linked dimer were then obtained by continued elution with the appropriate solvent system.

Example 35

3'-De (oxyphosphinico)-3'-(methyleneimino)-5'-O-(triphenylmethyl)thymidylyl-(3'→5')-3'-O-(tert-butyldiphenylsilyl)-2'-deoxyadenosine (9d)

From 297 mg (0.5 mmol) of 6b and 775 mg (1.5 mmol) of 7b according to general procedure F was obtained 515 mg (83% of unreacted material) of the starting oxime, and 291 mg (59%) of 9d after elution of the column with a gradient of 0% to 5% MeOH in 4:1 EtOAc/hexane: $R_f$ 0.41 (5% MeOH in 4:1 EtOAc/hexane); $^1$H NMR (CDCl$_3$) δ 12.50 (s, 1H), 8.34 (s, 1H), 8.23 (s, 1H), 7.70–7.10 (m, 26H), 6.55 (t, J=6.8 Hz, 1H), 6.45 (bs, 2H), 6.08 (t, J=5.6 Hz, 1H), 5.98 (s, 1H), 4.50 (m, 1H), 4.07 (m, 1H), 3.94 (m, 1H), 3.47 (m, 2H), 3.28 (dd, 1H), 3.20 (dd, 1H), 2.84 (m, 2H), 2.45 (m, 3H), 2.19 (t, 2H), 1.52 (s, 1H), 1.09 (s, 9H). Anal. Calcd for C$_{56}$H$_{60}$N$_8$O$_7$Si·0.5 H$_2$O: C, 67.65; H, 6.18; N, 11.27. Found: C, 67.77; H, 6.06; N, 11.35.

What is claimed is:

1. An oligonucleotide comprising from 8 to 30 nucleotide units specifically hybridizable with selected DNA or mRNA deriving from the human H-ras gene and containing a first region having at least one nucleosidic unit modified at the 2' position with a 2'-O-methoxyethyl substituent and a second region having at least one phosphorothioate linkage.

2. The oligonucleotide of claim 1 wherein said first region has at least three nucleosidic units modified at the 2' position with 2'-O-methoxyethyl substituents.

3. The oligonucleotide of claim 1 wherein said second region has at least four nucleosidic units linked together with phosphorothioate linkages.

4. The oligonucleotide of claim 2 wherein each of the nucleosidic units of said second region are 2'-deoxynucleotides.

5. The oligonucleotide of claim 4 wherein said second region is flanked by two of said first regions each of which includes at least one nucleosidic unit modified at the 2' position with a 2'-methoxyethyl substituent.

6. The oligonucleotide of claim 1 comprising SEQ ID No: 2.

7. An oligonucleotide comprising from 8 to 30 nucleotide units hybridizable with selected DNA or mRNA deriving from the human H-ras gene and containing at least one nucleosidic unit modified at the 2' position with a 2'-O-methoxyethyl substituent.

8. The oligonucleotide of claim 7 comprising SEQ ID No: 2.

* * * * *

UNITED STATES PATENT AND TRADEMARK OFFICE
CERTIFICATE OF CORRECTION

PATENT NO.    : 6,359,124 B1
DATED         : March 19, 2002
INVENTOR(S)   : Ecker et al.

It is certified that error appears in the above-identified patent and that said Letters Patent is hereby corrected as shown below:

<u>Title page,</u>
Item [56], OTHER PUBLICATIONS, "Sproat, B.S. et al." please delete "proobes" and insert therefor -- probes --;
"Inoue et al." please delete "hybrolysis" and insert therefor -- hydrolysis --;
References Cited, U.S. PATENT DOCUMENTS, "5,087,617 Smith" please delete "2/1992" and insert therefor -- 5/1992 --;
"5,149,797 Pederson et al." please delete "9/1992" and insert therefor -- 11/1992 --;

<u>Column 11,</u>
Line 28, please delete "O1'CH$_2$" and insert therefor -- O-CH$_2$ --;

Signed and Sealed this

Fifteenth Day of October, 2002

*Attest:*

*Attesting Officer*

JAMES E. ROGAN
*Director of the United States Patent and Trademark Office*